US008383117B2

(12) United States Patent
Glover et al.

(10) Patent No.: US 8,383,117 B2
(45) Date of Patent: Feb. 26, 2013

(54) CD44E TUMOR SPECIFIC ANTIBODY

(75) Inventors: Nicholas Ronald Glover, Oakville (CA); Glen Christopher MacDonald, Winnipeg (CA); Joycelyn Entwistle, Winnipeg (CA); Jeannick Cizeau, Winnipeg (CA); Denis Georges Bosc, Winnipeg (CA); Francina C. Chahal, Winnipeg (CA)

(73) Assignee: Viventia Biotechnologies Inc., Mississauga, Ontario (CA)

( * ) Notice: Subject to any disclaimer, the term of this patent is extended or adjusted under 35 U.S.C. 154(b) by 236 days.

(21) Appl. No.: 11/570,198

(22) PCT Filed: Jun. 10, 2005

(86) PCT No.: PCT/CA2005/000899
§ 371 (c)(1),
(2), (4) Date: Jun. 27, 2007

(87) PCT Pub. No.: WO2005/121341
PCT Pub. Date: Dec. 22, 2005

(65) Prior Publication Data
US 2007/0292441 A1 Dec. 20, 2007

Related U.S. Application Data

(60) Provisional application No. 60/578,291, filed on Jun. 10, 2004.

(51) Int. Cl.
*A61K 39/395* (2006.01)
*C07K 16/00* (2006.01)

(52) U.S. Cl. ............... 424/141.1; 424/155.1; 424/178.1; 424/183.1; 530/388.1; 530/388.8; 530/391.3

(58) Field of Classification Search ........................ None
See application file for complete search history.

(56) References Cited

U.S. PATENT DOCUMENTS
5,863,540 A * 1/1999 Haynes et al. ............ 424/185.1

OTHER PUBLICATIONS

Mizejewski et al, Experimental Biology and Medicine, 2001, 226:337-408.*
Hartog et al, Eur J Biochem, 2002, 269:1772-1779.*
In re Alonso, US Court of Appeals for the Federal Circuit, 2008 (p. 1-11).*
Rudikoff et al, PNAS, USA, 1982, 79: 1979.*
Rudikoff et al, PNAS, USA, 1982, 79: 1979-1983.*
Panka et al (Proc Natl Acad Sci, 1988, 85:3080-3084).*
MacCallum et al (J Mol Biology, 1996, 262:732-745).*
Chahal et al, Biochemical and Biophysical Research Communication, 2006, 348:1055-1062.*
GenBank™ Database Accession No. 70888283, immunoglobulin lambda light chain variable region [*Homo sapiens*], [NCBI GenPept: AAZ13744] Jul. 20, 2005.
GenBank™ Database Accession No. 16117104, immunoglobulin lambda chain variable region [*Homo sapiens*], [NCBI GenPept: CAC94710] Oct. 12, 2001.
GenBank™ Database Accession No. 7573146, immunoglobulin lambda light chain variable region [*Homo sapiens*], [NCBI GenPept: CAB87525] Oct. 27, 2000.
GenBank™ Database Accession No. 10637508, immunoglobulin lambda light chain variable region [*Homo sapiens*], [NCBI GenPept: CAC10905] Mar. 22, 2001.
GenBank™ Database Accession No. 563432, Ig heavy chain (VH4) V region (VDJ) [*Homo sapiens*], [NCBI GenPept: CAA63156] Dec. 19, 1994.
GenBank™ Database Accession No. 4426736, immunoglobulin heavy chain variable region [*Homo sapiens*], [NCBI GenPept: AAD20483] Jun. 1, 1999.
GenBank™ Database Accession No. 4456506, immunoglobulin heavy chain variable region [*Homo sapiens*], [NCBI GenPept: CAB37136] Feb. 22, 2000.
Codington JF et al. (Feb. 1, 2002), Immunologic quantitation of the carcinma specific human carcinoma antigen in clinical samples, *Cancer*, 94(3):803-813.
Fukasawa H, Iwamoto H, Hirata S at al. Novel human alpha-fetoprotein mRNA isoform lacking exon 1 identified in ovarian yolk sac tumor. J.Soc.Gynecol.Investig. 2005;12:456-462.
Karmali and Novo (1990), Human alfa-fetoprotein: isolation and production of monoclonal antibodies, *Biochimie*, 72:369-374.
Kim EE, DeLand FH, Nelson MO et al. Radioimmunodetection of cancer with radiolabeled antibodies to alpha-fetoprotein. Cancer Res 1980;40:3008-3012.
Konno H, Suzuki H, Tadakuma T et al. Antitumor effect of adriamycin entrapped in liposomes conjugated with anti-human alpha-fetoprotein monoclonal antibody. Cancer Res 1987;47:4471-4477.
Muramaki M, Miyake H, Kamidono S, Hara I. Over expression of CD44V8-10 in human bladder cancer cells decreases their interaction with hyaluronic acid and potentiates their malignant progression. J.Urol. 2004;171:426-430.
Sasaki JI, Tanabe KK, Takahashi K at al. Expression of CD44 splicing isoforms in lung cancers: dominant expression of CD44v8-10 in non-small cell lung carcinomas. Int.J.Oncol. 1998;12:525-533.
Winthrop MD et al. (Sep. 1, 2003), Selection and characterization of anti-MUC-1 scFvs intended for targeted therapy, *Clinical Cancer Research*, 9:3845s-3853s.
Yamaguchi A et al. (Dec. 1995), Expression of CD44 variant exons 8-10 in gastric cancer, *Jpn J. Cancer Res.*, 86:1166-1171.
Yamaguchi A et al. (Apr. 1996), Expression of a CD44 variant containing exons 8 to 10 is a useful independent factor for the prediction of prognosis in colorectal cancer patients, *Journal of Clinical Oncology*, 14(4):1122-1127.

(Continued)

*Primary Examiner* — Laura B Goddard
(74) *Attorney, Agent, or Firm* — Bereskin & Parr LLP/ S.E.N.C.R.L., s.r.l.; Micheline Gravelle

(57) ABSTRACT

The present invention provides the amino acid and nucleic acid sequences of heavy chain and light chain complementarity determining regions of a tumor specific antibody. In addition, the invention provides tumor-specific antibodies and immunoconjugates comprising the tumor-specific antibody attached to a toxin or label, and methods and uses thereof. The invention also relates to diagnostic methods and kits using the tumor-specific antibodies of the invention.

21 Claims, 27 Drawing Sheets

OTHER PUBLICATIONS

Yamaguchi A, Zhang M, Goi T et al. Expression of variant CD44 containing variant exon v8-10 in gallbladder cancer. Oncol.Rep. 2000;7:541-544.

Seki Kenichiro et all, "Inhibition of liver metastasis formation by anti-CD44 variant exon 9 monoclonal antibody", Intl J. of Oncology, vol. 11, No. 6, p. 1257-1261, 1997.

Yamaguchi, A. et al. "Clinical significance of combined immunohistochemical detection of CD44v and sialyl LeX expression for colorectal cancer patients undergoing curative resection", Oncology, vol. 55, No. 5, p. 400-404, 1998.

Sasaki, Ji-Ichiro et al., "Expression of CD44 splicing isoforms in lung cancers; Dominant expression of CD44v8-10 in non-small cell lung carcinomas", International Journal of Oncology, vol. 12, No. 3, p. 525-533, 1998.

Okamoto Isamu et al., "Molecular detection of cancer cells by competitive reverse transcription-polymerase chain reaction analysis of specific CD44 variants RNAs", J. of the National Cancer Institute (Bethesda), vol. 90, No. 4, p. 307-315, 1998.

Orteu, C.H. et al. "CD44 variant expression in cutaneous T-cell lymphoma", J. of Cutaneous Pathology, Blackwell Munksgaard, Copenhagen, Denmark, vol. 24, No. 6, p. 342-349, 1997.

Droll Armin et al. "Adhesive interactions between alternatively spliced CD44 isoforms", J. of Biological Chemistry, vol. 270, No. 19, p. 11567-11573, 1995.

Iczkowski et al. "Prostate Cancer Overexpressess CD44 variants 7-9 at the Messenger RNA and Protein Level" Anticancer Research, Intl Institute of Anticancer Research, vol. 23, No. 4, p. 3129-3140, 2003.

Naor et al. "CD44: Structure, function, and association with the malignant process", Advances in Cancer Research, Academic Press, London, GB, vol. 71, p. 241-319, 1997.

Chahal, et al. "A targeted proteomic approach for the identification of tumor-associated membrane antigens using the ProteomeLab(TM) PF-20 in tandem with mass spectrometry". Biochemical and Biophysical Research Communications, Academic Press Inc., Orlando, FL, US, vol. 348, No. 3, p. 1055-1062, 2006.

* cited by examiner

SEQ ID NO:8  TAT GAG CTG ACT CAG CCA CCC TCA GTG TCC GTG TCC CCA GGA CAG AAA GCC TTC
SEQ ID NO:7   Y   E   L   T   Q   P   P   S   V   S   V   S   P   G   Q   K   A   F

ATA ACC TGC TCT GGA GAT AAC CTG GGG AAT AAA TAT GTG TGC TGG TAT CAA CAG
 I   T   C   S   G   D   N   L   G   N   K   Y   V   C   W   Y   Q   Q
         |————————————— CDR 1 (L) —————————————|

AAG CCA GGC CAG TCC CCT GTC CTG GTC ATC TAT GAA GAT ACC AAG AGG CCC TCA
 K   P   G   Q   S   P   V   L   V   I   Y   E   D   T   K   R   P   S
                                         |————————— CDR 2 (L) —————————|

GGG ATC CCT GAG CGA TTC TCT GCC TCC AAC TCT GGG AAT ACA GCC ACT CTG ACC
 G   I   P   E   R   F   S   A   S   N   S   G   N   T   A   T   L   T

ATC AGC GGG ACG CAG CCT ATA GAT GAG GCT GAC TAC TAC TGT CAG GCG TGG GAC
 I   S   G   T   Q   P   I   D   E   A   D   Y   Y   C   Q   A   W   D
                                                         |—————————————

AGC CGC ACT GAA ATC TTC GGA ACT GGG ACC AAG GTC ACC GTC CTA AGT
 S   R   T   E   I   F   G   T   G   T   K   V   T   V   L   S
 CDR 3 (L) —————————|

Figure 2

VB1-008
V<sub>H</sub>

SEQ ID NO:10  CAG GTG CAG CTG CAG GAG TTG GGT CCA AGG CTG GTG AGG CCT TCA CAG ACC CTG
SEQ ID NO:9   Q   V   Q   L   Q   E   L   G   P   R   L   V   R   P   S   Q   T   L

ATC CTC ACC TGC ACT GTC TCT GGA GGC TCC GTC AGC GGC GAT GAG TAT TAC TGG
 I   L   T   C   T   V   S   G   G   S   V   S   G   D   E   Y   Y   W
                                                     |—————— CDR 1 (H) ——

AGT TGG CTC CGT CAG ACC CCA GGG AAG GGC CTG GAG TGG ATT GGG TAC ATG TCT
 S   W   L   R   Q   T   P   G   K   G   L   E   W   I   G   Y   M   S
—|                                                               |——————

TAC AGA GGG AGC AGT TAT TAC AGT CCG TCC CTC AGT CGA GTT ACC ATT GCA
 Y   R   G   S   S   Y   Y   S   P   S   L   Q   S   R   V   T   I   A
 ——— CDR 2 (H) ————————————————————————————|

GTG GAC AGG TCC AAG AAC GAA TTT TCC CTG AAG CTG ACG TCT GTG ACT GCC GCA
 V   D   R   S   K   N   E   F   S   L   K   L   T   S   V   T   A   A

GAC GCG GCC GTA TAT TTC TGT GCC AGA AAA TAT TGT GGT GGC GAT TGC AGG AGT
 D   A   A   V   Y   F   C   A   R   K   Y   C   G   G   D   C   R   S
                                     |——————————————————— CDR 3(H) ———

GGT TTT GAT ATC TGG GGC CGA GGG ACA ATG GTC ACC GTC GCT TCA
 G   F   D   I   W   G   R   G   T   M   V   T   V   A   S
————————————|

Figure 8
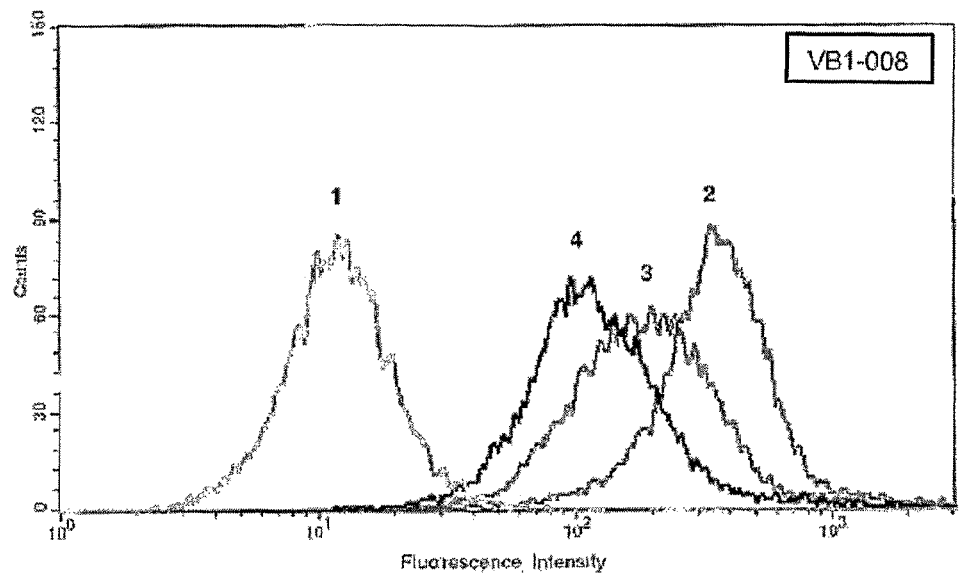
Figure 9
A            B
 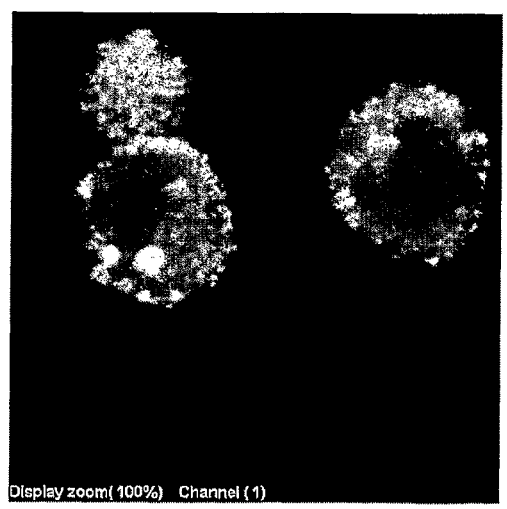

Figure 11A         Figure 11B

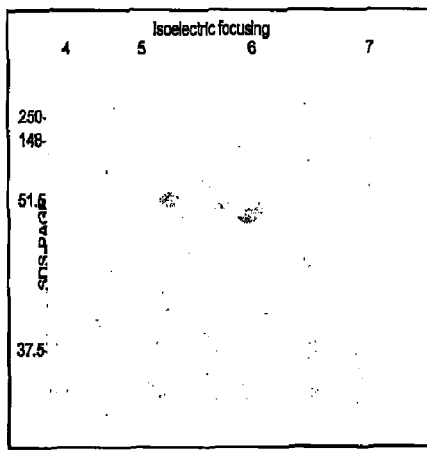
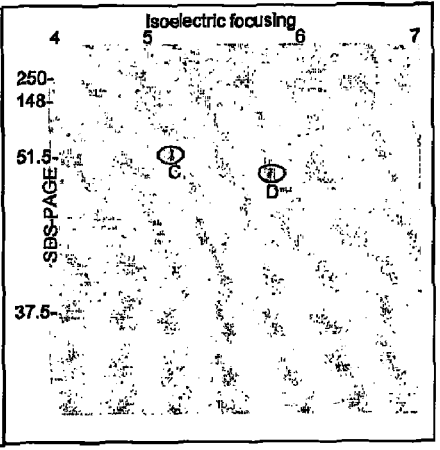

Figure 12A

```
      MKWVESIFLI FLLNFTESRT LHRNEYGIAS ILDSYQCTAE ISLADLATIF
 51  FAQFVQEATY KEVSKMVKDA LTAIEKPTGD EQSSGCLENQ LPAFLEELCH
101  EKEILEKYGH SDCCSQSEEG RHNCFLAHKK PTPASIPLFQ VPEPVTSCEA
151  YEEDRETFMN KFIYEIARRH PFLYAPTILL WAARYDKIIP SCCKAENAVE
201  CFQTKAATVT KELRESSLLN QHACAVMKNF GTRTFQAITV TKLSQKFTKV
251  NFTEIQKLVL DVAHVHEHCC RGDVLDCLQD GEKIMSYICS QQDTLSNKIT
301  ECCKLTTLER GQCIIHAEND EKPEGLSPNL NRFLGDRDFN QFSSGEKNIF
351  LASFVHEYSR RHPQLAVSVI LRVAKGYQEL LEKCFQTENP LECQDKGEEE
401  LQKYIQESQA LAKRSCGLFQ KLGEYYLQNA FLVAYTKKAP QLTSSELMAI
451  TRKMAATAAT CCQLSEDKLL ACGEGAADII IGHLCIRHEM TPVNPGVGQC
501  CTSSYANRRP CFSSLVVDET YVPPAFSDDK FIFHKDLCQA QGVALQTMKQ
551  EFLINLVKQK PQITEEQLEA VIADFSGLLE KCCQGQEQEV CFAEEGQKLI
601  SKTRAALGV
```

Alpha-fetoprotein sequence coverage

Figure 12B

```
      MKWVESIFLI FLLNFTESRT LHRNEYGIAS ILDSYQCTAE ISLADLATIF
 51  FAQFVQEATY KEVSKMVKDA LTAIEKPTGD EQSSGCLENQ LPAFLEELCH
101  EKEILEKYGH SDCCSQSEEG RHNCFLAHKK PTPASIPLFQ VPEPVTSCEA
151  YEEDRETFMN KFIYEIARRH PFLYAPTILL WAARYDKIIP SCCKAENAVE
201  CFQTKAATVT KELRESSLLN QHACAVMKNF GTRTFQAITV TKLSQKFTKV
251  NFTEIQKLVL DVAHVHEHCC RGDVLDCLQD GEKIMSYICS QQDTLSNKIT
301  ECCKLTTLER GQCIIHAEND EKPEGLSPNL NRFLGDRDFN QFSSGEKNIF
351  LASFVHEYSR RHPQLAVSVI LRVAKGYQEL LEKCFQTENP LECQDKGEEE
401  LQKYIQESQA LAKRSCGLFQ KLGEYYLQNA FLVAYTKKAP QLTSSELMAI
451  TRKMAATAAT CCQLSEDKLL ACGEGAADII IGHLCIRHEM TPVNPGVGQC
501  CTSSYANRRP CFSSLVVDET YVPPAFSDDK FIFHKDLCQA QGVALQTMKQ
551  EFLINLVKQK PQITEEQLEA VIADFSGLLE KCCQGQEQEV CFAEEGQKLI
601  SKTRAALGV
```

AFP truncated – 54% sequence homology to human AFP –100% sequence homology

Figure 13

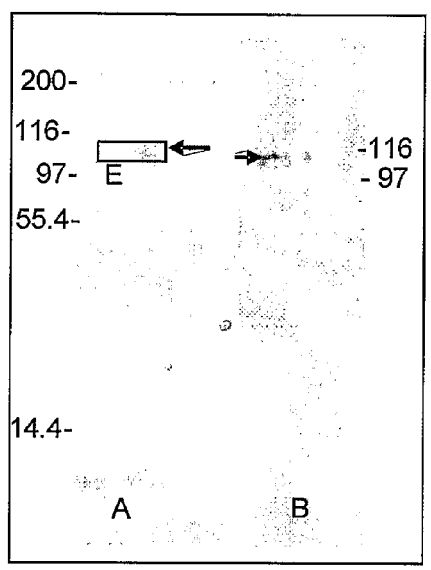

SDS-PAGE/Western profile of 100 kDa band subsequent to VB1-008 IP

Figure 14

```
MDKFWWHAAW GLCLVPLSLA QIDLNITCRF AGVFHVEKNG RYSISRTEAA DLCKAFNSTL
PTMAQMEKAL SIGFETCRYG FIEGHVVIPR IHPNSICAAN NTGVYILTSN TSQYDTYCFN
ASAPPEEDCT SVTDLPNAFD GPITITIVNR DGTRYVQKGE YRTNPEDIYP SNPTDDDVSS
GSSSERSSTS GGYIFYTFST VHPIPDEDSP WITDSTDRIP ATNMDSSHSI TLQPTANPNT
GLVEDLDRTG PLSMTTQQSN SQSFSTSHEG LEEDKDHPTT STLTSSNRND VTGGRRDPNH
SEGSTTLLEG YTSHYPHTKE SRTFIPVTSA KTGSFGVTAV TVGDSNSNVN RSLSGDQDTF
HPSGGSHTTH GSESDGHSHG SQEGGANTTS GPIRTPQIPE WLIILASLLA LALILAVCIA
VNSRRRCGQK KKLVINSGNG AVEDRKPSGL NGEASKSQEM VHLVNKESSE TPDQFMTADE
TRNLQNVDMKIGV
```

CD44-isoform 3 sequence coverage

Validation of AFP as a part of the antigen complex

Confirmation of the 2D-PAGE using anti-AFP and anti CD44

Cross-reactivity of AFP to CD44

Schematic representation of CD44 isomers in humans

Figure 18A

```
CD44E/ CD44-isoform-3
MDKFWWHAAW GLCLVPLSLA QIDLNITCRF AGVFHVEKNG RYSISRTEAA DLCKAFNSTL
PTMAQMEKAL SIGFETCRYG FIEGHVVIPR IHPNSICAAN NTGVYILTSN TSQYDTYCFN
ASAPPEEDCT SVTDLPNAFD GPITITIVNR DGTRYVQKGE YRTNPEDIYP SNPTDDDVSS
GSSSERSSTS GGYIFYTFST VHPIPDEDSP WITDSTDRIP ATNMDSSHSI TLQPTANPNT
GLVEDLDRTG PLSMTTQQSN SQSFSTSHEG LEEDKDHPTT STLTSSNRND VTGGRRDPNH
SEGSTTLLEG YTSHYPHTKE SRTFIPVTSA KTGSFGVTAV TVGDSNSNVN RSLSGDQDTF
HPSGGSHTTH GSESDGHSHG SQEGGANTTS GPIRTPQIPE WLIILASLLA LALILAVCIA
VNSRRRCGQK KKLVINSGNG AVEDRKPSGL NGEASKSQEM VHLVNKESSE TPDQFMTADE
TRNLQNVDMKIGV
```

Exon5-V8 = STDRIPATNMDSSHSIT - 17a

Figure 18B

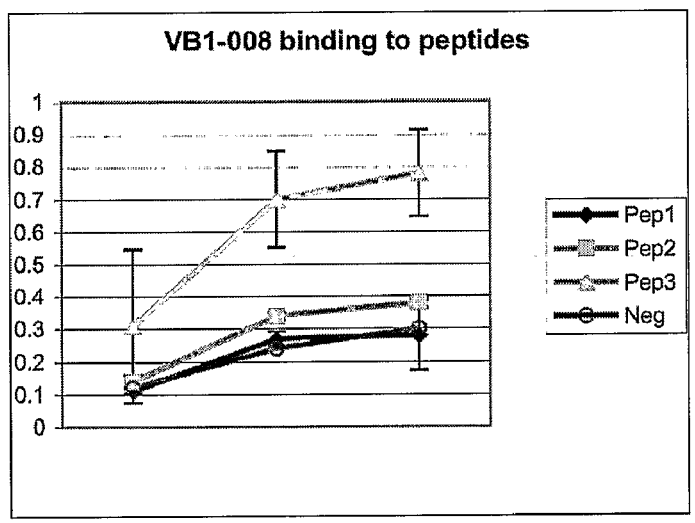

Figure 20

VB6-008 nucleotide sequence (SEQ ID NO:11)

GAATTCCTGCAGGTCTATGGAACGATAAATGCCCATGAAAATTCTATTTCAAGGAGACAGTCATAatgaaatacc
tattgcctacggcagccgctggattgttattactcgctgcccaaccagcgatggcgCAGGTGCAGCTGCAGGAGT
TGGGTCCAAGGCTGGTGAGGCCTTCACAGACCCTGATCCTCACCTGCACTGTCTCTGGAGGCTCCGTCAGCGGCG
ATGAGTATTACTGGAGTTGGCTCCGTCAGACCCCAGGGAAGGGCCTGGAGTGGATTGGGTACATGTCTTACAGAG
GGAGCAGTTATTACAGTCCGTCCCTCCAGAGTCGAGTTACCATTGCAGTGGACAGGTCCAAGAACGAATTTTCCC
TGAAGCTGACGTCTGTGACTGCCGCAGACGCGGCCGTATATTTCTGTGCCAGAAAATATTGTGGTGGCGATTGCA
GGAGTGGTTTTGATATCTGGGGCCGAGGGACAATGGTCACTGTCGCTAGCGCCTCCACCAAGGGCCCATCGGTCT
TCCCCCTGGCACCCTCCTCCAAGGCACCTCTGGGGCACAGCGGCCCTGGGCTGCCTGGTCAAGGACTACTTCCC
CGAACCGGTGACGGTGTCGTGGAACTCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTTGGGCACCCAGACCTACATCTGCAA
CGTGAATCACAAGCCCAGCAACACCAAGGTGGACAAGAAAGTTGAGCCCAAATCTTGTACCAGGCACAGGCAGCC
CAGAGGCTGGGAGCAGCTCTACAACACTGTGTCATTTAACCTTGGAGAAGCTTATGAGTACCCCACTTTTATACA
AGATTTGCGCAATGAATTGGCTAAGGGCACACCAGTATGTCAACTTCCAGTGACACTACAAACCATAGCCGATGA
CAAGCGATTTGTTCTAGTTGATATCACTACGACCTCGAAGAAAACAGTTAAGGTTGCTATAGATGTGACAGATGT
GTATGTTGTGGGTTATCAAGACAAATGGGATGGCAAAGATCGAGCTGTTTTCCTTGACAAGGTTCCTACTGTTGC
AACTAGTAAACTTTTCCCAGGGGTGACTAATCGTGTAACGTTAACATTTGATGGCAGCTATCAGAAACTTGTGAA
TGCTGCCAAAGCTGATAGAAAGGCTCTCGAACTGGGGGTTAACAAATTGGAATTTTCCATTGAAGCAATCCATGG
TAAAACGATAAATGGTCAAGAGGCAGCCAAGTTCTTTCTTATTGTCATCCAAATGGTTTCAGAGGCAGCTCGGTT
CAAATATATTGAGACTGAGGTGGTTGATAGAGGATTATATGGATCATTCAAACCTAATTTTAAAGTATTGAACTT
GGAGAACAATTGGGGCGACATCTCTGATGCCATTCACAAATCATCCCCACAATGTACCACTATTAATCCGGCACT
TCAGTTGATAAGCCCCTCAAATGACCCATGGGTTGTAAATAAAGTGAGTCAAATTAGTCCCGATATGGGTATCCT
TAAGTTTAAAAGCTCCAAATAGTGAGTCGACTCTAGACTGCAGGTCTATGGAACGATAAATGCCCATGAAAATTC
TATTTCAAGGAGACAGTCATAatgaaatacctattgcctacggcagccgctggattgttattactcgctgcccaa
ccagcgatggcgCATCACCATCACCATCACTATGAGCTGACTCAGCCACCCTCAGTGTCCGTGTCCCCAGGACAG
AAAGCCTTCATAACCTGCTCTGGAGATAACCTGGGGAATAAATATGTGTGCTGGTATCAACAGAAGCCAGGCCAG
TCCCCTGTCCTGGTCATCTATGAAGATACCAAGAGGCCCTCAGGGATCCCTGAGCGATTCTCTGCCTCCAACTCT
GGGAATACAGCCACTCTGACCATCAGCGGGACGCAGCCTATAGATGAGGCTGACTACTACTGTCAGGCGTGGGAC
AGCCGCACTGAAATCTTCGGAACTGGGACCAAGGTCACCGTCCTAAGTCAGCCCAAGGCCAACCCCACTGTCACT
CTGTTCCCGCCCTCCTCTGAGGAGCTCCAAGCCAACAAGGCCACACTAGTGTGTCTGATCAGTGACTTCTACCCG
GGAGCTGTGACAGTGGCCTGGAAGGCAGATGGCAGCCCCGTCAAGGCGGGAGTGGAGACCACCAAACCCTCCAAA
CAGAGCAACAACAAGTACGCGGCCAGCAGCTACCTGAGCCTGACGCCCGAGCAGTGGAAGTCCCACAGAAGCTAC
AGCTGCCAGGTCACGCATGAAGGGAGCACCGTGGAGAAGACAGTGGCCCCTACAGAATGTTCATAGTGACTCGAG

PelB-V$_{H008}$-C$_H$-F-de-bouganin (SEQ ID NO:12)
MKYLLPTAAAGLLLLAAQPAMAQVQLQELGPRLVRPSQTLILTCTVSGGSVSGDEYYWSWLRQTPGKGLEWIGYM
SYRGSSYYSPSLQSRVTIAVDRSKNEFSLKLTSVTAADAAVYFCARKYCGGDCRSGFDIWGRGTMVTVASASTKG
PSVFPLAPSSKSTSGGTAALGCLVKDYFPEPVTVSWNSGALTSGVHTFPAVLQSSGLYSLSSVVTVPSSSLGTQT
YICNVNHKPSNTKVDKKVEPKSCTRHRQPRGWEQLYNTVSFNLGEAYEYPTFIQDLRNELAKGTPVCQLPVTLQT
IADDKRFVLVDITTTSKKTVKVAIDVTDVYVVGYQDKWDGKDRAVFLDKVPTVATSKLFPGVTNRVTLTFDGSYQ
KLVNAAKADRKALELGVNKLEFSIEAIHGKTINGQEAAKFFLIVIQMVSEAARFKYIETEVVDRGLYGSFKPNFK
VLNLENNWGDISDAIHKSSPQCTTINPALQLISPSNDPWVVNKVSQISPDMGILKFKSSK

PelB-V$_{L008}$-C$_L$ (SEQ ID NO: 13)
MKYLLPTAAAGLLLLAAQPAMAHHHHHHYELTQPPSVSVSPGQKAFITCSGDNLGNKYVCWYQQKPGQSPVLVIY
EDTKRPSGIPERFSASNSGNTATLTISGTQPIDEADYYCQAWDSRTEIFGTGTKVTVLSQPKANPTVTLFPPSSE
ELQANKATLVCLISDFYPGAVTVAWKADGSPVKAGVETTKPSKQSNNKYAASSYLSLTPEQWKSHRSYSCQVTHE
GSTVEKTVAPTECS

Figure 22 (cont'd)

```
          CTTCCCCGAACCGGTGACGGTGTCGTGGAACTCAGGCGCCCTGACCAGCGGCGTGCACACCTTCCCGGCTGTCCTACAGTCCTCA
          |----|----|----|----|----|----|----|----|----|----|----|----|----|----|----|----|----| 680
          GAAGGGGCTTGGCCACTGCCACAGCACCTTGAGTCCGCGGGACTGGTCGCCGCACGTGTGGAAGGGCCGACAGGATGTCAGGAGT

F    P    E    P    V    T    V    S    W    N    S    G    A    L    T    S    G    V    H    T    F    P    A    V    L    Q    S    S

GGACTCTACTCCCTCAGCAGCGTGGTGACCGTGCCCTCCAGCAGCTTGGGCACCCAGACCTACATCTGCAACGTGAATCACAAGC
          |----|----|----|----|----|----|----|----|----|----|----|----|----|----|----|----|----| 765
          CCTGAGATGAGGGAGTCGTCGCACCACTGGCACGGGAGGTCGTCGAACCCGTGGGTCTGGATGTAGACGTTGCACTTAGTGTTCG

G    L    Y    S    L    S    S    V    V    T    V    P    S    S    S    L    G    T    Q    T    Y    I    C    N    V    N    H    K

CCAGCAACACCAAGGTGGACAAGAAAGTTGAGCCCAAATCTTGTACCAGGCACAGGCAGCCCAGAGGCTGGGAGCAGCTCTACAA
          |----|----|----|----|----|----|----|----|----|----|----|----|----|----|----|----|----| 850
          GGTCGTTGTGGTTCCACCTGTTCTTTCAACTCGGGTTTAGAACATGGTCCGTGTCCGTCGGGTCTCCGACCCTCGTCGAGATGTT
                                           |━━━━━━━━━ Furin Linker ━━━━━━━━━|  ▪ start ▪

P    S    N    T    K    V    D    K    K    V    E    P    K    S    C    T    R    H    R    Q    P    R    G    W    E    Q    L    Y    N

CACTGTGTCATTTAACCTTGGAGAAGCTTATGAGTACCCCACTTTTATACAAGATTTGCGCAATGAATTGGCTAAGGGCACACCA
          |----|----|----|----|----|----|----|----|----|----|----|----|----|----|----|----|----| 935
          GTGACACAGTAAATTGGAACCTCTTCGAATACTCATGGGGTGAAAATATGTTCTAAACGCGTTACTTAACCGATTCCCGTGTGGT
          |━━━━━━━ start of De-Bouganin156 ━━━━━━▶

T    V    S    F    N    L    G    E    A    Y    E    Y    P    T    F    I    Q    D    L    R    N    E    L    A    K    G    T    P

GTATGTCAACTTCCAGTGACACTACAAACCATAGCCGATGACAAGCGATTTGTTCTAGTTGATATCACTACGACCTCGAAGAAAA
          |----|----|----|----|----|----|----|----|----|----|----|----|----|----|----|----|----| 1020
          CATACAGTTGAAGGTCACTGTGATGTTTGGTATCGGCTACTGTTCGCTAAACAAGATCAACTATAGTGATGCTGGAGCTTCTTTT

V    C    Q    L    P    V    T    L    Q    T    I    A    D    D    K    R    F    V    L    V    D    I    T    T    T    S    K    K

CAGTTAAGGTTGCTATAGATGTGACAGATGTGTATGTTGTGGGTTATCAAGACAAATGGGATGGCAAAGATCGAGCTGTTTTCCT
          |----|----|----|----|----|----|----|----|----|----|----|----|----|----|----|----|----| 1105
          GTCAATTCCAACGATATCTACACTGTCTACACATACAACACCCAATAGTTCTGTTTACCCTACCGTTTCTAGCTCGACAAAAGGA

T    V    K    V    A    I    D    V    T    D    V    Y    V    V    G    Y    Q    D    K    W    D    G    K    D    R    A    V    F    L

TGACAAGGTTCCTACTGTTGCAACTAGTAAACTTTTCCCAGGGGTGACTAATCGTGTAACGTTAACATTTGATGGCAGCTATCAG
          |----|----|----|----|----|----|----|----|----|----|----|----|----|----|----|----|----| 1190
          ACTGTTCCAAGGATGACAACGTTGATCATTTGAAAAGGGTCCCCACTGATTAGCACATTGCAATTGTAAACTACCGTCGATAGTC

D    K    V    P    T    V    A    T    S    K    L    F    P    G    V    T    N    R    V    T    L    T    F    D    G    S    Y    Q

AAACTTGTGAATGCTGCCAAAGCTGATAGAAAGGCTCTCGAACTGGGGGTTAACAAATTGGAATTTTCCATTGAAGCAATCCATG
          |----|----|----|----|----|----|----|----|----|----|----|----|----|----|----|----|----| 1275
          TTTGAACACTTACGACGGTTTCGACTATCTTTCCGAGAGCTTGACCCCCAATTGTTTAACCTTAAAAGGTAACTTCGTTAGGTAC

```
GTAAAACGATAAATGGTCAAGAGGCAGCCAAGTTCTTTCTTATTGTCATCCAAATGGTTTCAGAGGCAGCTCGGTTCAAATATAT
----+----|----+----|----+----|----+----|----+----|----+----|----+----|----+----|----+ 1360
CATTTTGCTATTTACCAGTTCTCCGTCGGTTCAAGAAAGAATAACAGTAGGTTTACCAAAGTCTCCGTCGAGCCAAGTTTATATA

G  K  T  I  N  G  Q  E  A  A  K  F  F  L  I  V  I  Q  M  V  S  E  A  A  R  F  K  Y  I
TGAGACTGAGGTGGTTGATAGAGGATTATATGGATCATTCAAACCTAATTTTAAAGTATTGAACTTGGAGAACAATTGGGGCGAC
----+----|----+----|----+----|----+----|----+----|----+----|----+----|----+----|----+ 1445
ACTCTGACTCCACCAACTATCTCCTAATATACCTAGTAAGTTTGGATTAAAATTTCATAACTTGAACCTCTTGTTAACCCCGCTG

E  T  E  V  V  D  R  G  L  Y  G  S  F  K  P  N  F  K  V  L  N  L  E  N  N  W  G  D
ATCTCTGATGCCATTCACAAATCATCCCCACAATGTACCACTATTAATCCGGCACTTCAGTTGATAAGCCCCTCAAATGACCCAT
----+----|----+----|----+----|----+----|----+----|----+----|----+----|----+----|----+ 1530
TAGAGACTACGGTAAGTGTTTAGTAGGGGTGTTACATGGTGATAATTAGGCCGTGAAGTCAACTATTCGGGGAGTTTACTGGGTA

I  S  D  A  I  H  K  S  S  P  Q  C  T  T  I  N  P  A  L  Q  L  I  S  P  S  N  D  P
GGGTTGTAAATAAAGTGAGTCAAATTAGTCCCGATATGGGTATCCTTAAGTTTAAAAGCTCCAAATAGTGACTCGAGGAATTCCT
----+----|----+----|----+----|----+----|----+----|----+----|----+----|----+----|----+ 1615
CCCAACATTTATTTCACTCAGTTTAATCAGGGCTATACCCATAGGAATTCAAATTTTCGAGGTTTATCACTGAGCTCCTTAAGGA
                                     |━━━━ end of De-Bouganin156 ━━━━|

W  V  V  N  K  V  S  Q  I  S  P  D  M  G  I  L  K  F  K  S  S  K
GCAGGTCTATGGAACGATAAATGCCCATGAAAATTCTATTTCAAGGAGACAGTCATAATGAAATACCTATTGCCTACGGCAGCCG
----+----|----+----|----+----|----+----|----+----|----+----|----+----|----+----|----+ 1700
CGTCCAGATACCTTGCTATTTACGGGTACTTTTAAGATAAAGTTCCTCTGTCAGTATTACTTTATGGATAACGGATGCCGTCGGC
                                                          |━━━━ PelB ━━━━
                                                         M  K  Y  L  L  P  T  A  A

CTGGATTGTTATTACTCGCTGCCCAACCAGCGATGGCGCATCACCATCACCATCACTATGAGCTGACTCAGCCACCCTCAGTGTC
----+----|----+----|----+----|----+----|----+----|----+----|----+----|----+----|----+ 1785
GACCTAACAATAATGAGCGACGGGTTGGTCGCTACCGCGTAGTGGTAGTGGTAGTGATACTCGACTGAGTCGGTGGGAGTCACAG
━━━━ PelB ━━━━|         | 6xHis |           ━━━ start of VL ━━━▶
  A  G  L  L  L  L  A  A  Q  P  A  M  A  H  H  H  H  H  H  Y  E  L  T  Q  P  P  S  V  S CGTGTCCCCAGGACAGAAAGCCTTCATAACCTGCTCTGGAGATAACCTGGGGAATAAATATGTGTGCTGGTATCAACAGAAGCCA
----+----|----+----|----+----|----+----|----+----|----+----|----+----|----+----|----+ 1870
GCACAGGGGTCCTGTCTTTCGGAAGTATTGGACGAGACCTCTATTGGACCCCTTATTTATACACACGACCATAGTTGTCTTCGGT V  S  P  G  Q  K  A  F  I  T  C  S  G  D  N  L  G  N  K  Y  V  C  W  Y  Q  Q  K  P
GGCCAGTCCCCTGTCCTGGTCATCTATGAAGATACCAAGAGGCCCTCAGGGATCCCTGAGCGATTCTCTGCCTCCAACTCTGGGA
----+----|----+----|----+----|----+----|----+----|----+----|----+----|----+----|----+ 1955
CCGGTCAGGGGACAGGACCAGTAGATACTTCTATGGTTCTCCGGGAGTCCCTAGGGACTCGCTAAGAGACGGAGGTTGAGACCCT G  Q  S  P  V  L  V  I  Y  E  D  T  K  R  P  S  G  I  P  E  R  F  S  A  S  N  S  G
```

Figure 22 (cont'd)

```
ATACAGCCACTCTGACCATCAGCGGGACGCAGCCTATAGATGAGGCTGACTACTACTGTCAGGCGTGGGACAGCCGCACTGAAAT
                                                                                      2040
TATGTCGGTGAGACTGGTAGTCGCCCTGCGTCGGATATCTACTCCGACTGATGATGACAGTCCGCACCCTGTCGGCGTGACTTTA

N  T  A  T  L  T  I  S  G  T  Q  P  I  D  E  A  D  Y  Y  C  Q  A  W  D  S  R  T  E  I

CTTCGGAACTGGGACCAAGGTCACCGTCCTAAGTCAGCCCAAGGCCAACCCCACTGTCACTCTGTTCCCGCCCTCCTCTGAGGAG
                                                                                      2125
GAAGCCTTGACCCTGGTTCCAGTGGCAGGATTCAGTCGGGTTCCGGTTGGGGTGACAGTGAGACAAGGGCGGGAGGAGACTCCTC

▬▬ end of VL ▬▬▬       ▬▬ start of CL ▬▬▬▶
 F  G  T  G  T  K  V  T  V  L  S  Q  P  K  A  N  P  T  V  T  L  F  P  P  S  S  E  E CTCCAAGCCAACAAGGCCACACTAGTGTGTCTGATCAGTGACTTCTACCCGGGAGCTGTGACAGTGGCCTGGAAGGCAGATGGCA
                                                                                      2210
GAGGTTCGGTTGTTCCGGTGTGATCACACAGACTAGTCACTGAAGATGGGCCCTCGACACTGTCACCGGACCTTCCGTCTACCGT L  Q  A  N  K  A  T  L  V  C  L  I  S  D  F  Y  P  G  A  V  T  V  A  W  K  A  D  G GCCCCGTCAAGGCGGGAGTGGAGACCACCAAACCCTCCAAACAGAGCAACAACAAGTACGCGGCCAGCAGCTACCTGAGCCTGAC
                                                                                      2295
CGGGGCAGTTCCGCCCTCACCTCTGGTGGTTTGGGAGGTTTGTCTCGTTGTTGTTCATGCGCCGGTCGTCGATGGACTCGGACTG S  P  V  K  A  G  V  E  T  T  K  P  S  K  Q  S  N  N  K  Y  A  A  S  S  Y  L  S  L  T GCCCGAGCAGTGGAAGTCCCACAGAAGCTACAGCTGCCAGGTCACGCATGAAGGGAGCACCGTGGAGAAGACAGTGGCCCCTACA
                                                                                      2380
CGGGCTCGTCACCTTCAGGGTGTCTTCGATGTCGACGGTCCAGTGCGTACTTCCCTCGTGGCACCTCTTCTGTCACCGGGGATGT P  E  Q  W  K  S  H  R  S  Y  S  C  Q  V  T  H  E  G  S  T  V  E  K  T  V  A  P  T

GAATGTTCATAGTGACTCGAG
                      2401
CTTACAAGTATCACTGAGCTC

▬ end of CL ▬
  E  C  S
```

Figure 23

```
GAATTCCTGCAGGTCTATGGAACGATAAATGCCCATGAAAATTCTATTTCAAGGAGACAGTCATAATGAAATACCTATTGCCTAC
|---+---+---+---+---+---+---+---+---+---+---+---+---+---+---+---+---| 85
CTTAAGGACGTCCAGATACCTTGCTATTTACGGGTACTTTTAAGATAAAGTTCCTCTGTCAGTATTACTTTATGGATAACGGATG
                                                              ▬▬▬▬ PelB ▬▬▬▬
                                                                M  K  Y  L  L  P  T
```

```
GGCAGCCGCTGGATTGTTATTACTCGCTGCCCAACCAGCGATGGCGCAGGTGCAGCTGCAGGAGTTGGGTCCAACGCTGGTGAGG
|---+---+---+---+---+---+---+---+---+---+---+---+---+---+---+---+---| 170
CCGTCGGCGACCTAACAATAATGAGCGACGGGTTGGTCGCTACCGCGTCCACGTCGACGTCCTCAACCCAGGTTCCGACCACTCC
▬▬▬▬▬▬▬▬▬▬ PelB ▬▬▬▬▬▬▬▬▬▬▬▬■▬▬▬▬ start of VH ▬▬▬▬▶
  A  A  A  G  L  L  L  L  A  A  Q  P  A  M  A  Q  V  Q  L  Q  E  L  G  P  R  L  V  R
```

```
CCTTCACAGACCCTGATCCTCACCTGCACTGTCTCTGGAGGCTCCGTCAGCGGCGATGAGTATTACTGGAGTTGGCTCCGTCAGA
|---+---+---+---+---+---+---+---+---+---+---+---+---+---+---+---+---| 255
GGAAGTGTCTGGGACTAGGAGTGGACGTGACAGAGACCTCCGAGGCAGTCGCCGCTACTCATAATGACCTCAACCGAGGCAGTCT

P  S  Q  T  L  I  L  T  C  T  V  S  G  G  S  V  S  G  D  E  Y  Y  W  S  W  L  R  Q
```

```
CCCCAGGGAAGGGCCTGGAGTGGATTGGGTACATGTCTTACAGAGGGAGCAGTTATTACAGTCCGTCCCTCCAGAGTCGAGTTAC
|---+---+---+---+---+---+---+---+---+---+---+---+---+---+---+---+---| 340
GGGGTCCCTTCCCGGACCTCACCTAACCCATGTACAGAATGTCTCCCTCGTCAATAATGTCAGGCAGGGAGGTCTCAGCTCAATG

T  P  G  K  G  L  E  W  I  G  Y  M  S  Y  R  G  S  S  Y  Y  S  P  S  L  Q  S  R  V  T
```

```
CATTGCAGTGGACAGGTCCAAGAACGAATTTTCCCTGAAGCTGACGTCTGTGACTGCCGCAGACGCGGCCGTATATTTCTGTGCC
|---+---+---+---+---+---+---+---+---+---+---+---+---+---+---+---+---| 425
GTAACGTCACCTGTCCAGGTTCTTGCTTAAAAGGGACTTCGACTGCAGACACTGACGGCGTCTGCGCCGGCATATAAAGACACGG

I  A  V  D  R  S  K  N  E  F  S  L  K  L  T  S  V  T  A  A  D  A  A  V  Y  F  C  A
```

```
AGAAAATATTGTGGTGGCGATTGCAGGAGTGGTTTTGATATCTGGGGCCGAGGGACAATGGTCACTGTCGCTAGCGCCTCCACCA
|---+---+---+---+---+---+---+---+---+---+---+---+---+---+---+---+---| 510
TCTTTTATAACACCACCGCTAACGTCCTCACCAAAACTATAGACCCCGGCTCCCTGTTACCAGTGACAGCGATCGCGGAGGTGGT
                                                ▬▬▬ end of VH ▬▬▬■ start of CH ▬
  R  K  Y  C  G  G  D  C  R  S  G  F  D  I  W  G  R  G  T  M  V  T  V  A  S  A  S  T
```

```
AGGGCCCATCGGTCTTCCCCCTGGCACCCTCCTCCAAGAGCACCTCTGGGGGCACAGCGGCCCTGGGCTGCCTGGTCAAGGACTA
|---+---+---+---+---+---+---+---+---+---+---+---+---+---+---+---+---| 595
TCCCGGGTAGCCAGAAGGGGGACCGTGGGAGGAGGTTCTCGTGGAGACCCCCGTGTCGCCGGGACCCGACGGACCAGTTCCTGAT
▬▬▬▬ start of CH ▬▬▬▬▶
  K  G  P  S  V  F  P  L  A  P  S  S  K  S  T  S  G  G  T  A  A  L  G  C  L  V  K  D  Y
```

```
CTTCCCCGAACCGGTGACGGTGTCGTGGAACTCAGGCGCCCTGACCAGCGGCGTGCACACCTTCCCGGCTGTCCTACAGTCCTCA
|---+---+---+---+---+---+---+---+---+---+---+---+---+---+---+---+---| 680
GAAGGGGCTTGGCCACTGCCACAGCACCTTGAGTCCGCGGGACTGGTCGCCGCACGTGTGGAAGGGCCGACAGGATGTCAGGAGT

F  P  E  P  V  T  V  S  W  N  S  G  A  L  T  S  G  V  H  T  F  P  A  V  L  Q  S  S
```

```
GGACTCTACTCCCTCAGCAGCGTGGTGACCGTGCCCTCCAGCAGCTTGGGCACCCAGACCTACATCTGCAACGTGAATCACAAGC
|---+---+---+---+---+---+---+---+---+---+---+---+---+---+---+---+---| 765
CCTGAGATGAGGGAGTCGTCGCACCACTGGCACGGGAGGTCGTCGAACCCGTGGGTCTGGATGTAGACGTTGCACTTAGTGTTCG

```
CCAGCAACACCAAGGTGGACAAGAAAGTTGAGCCCAAATCTTGTACCAGGCACAGGCAGCCCAGAGGCTGGGAGCAGCTCTACAA
                                                                                    850
GGTCGTTGTGGTTCCACCTGTTCTTTCAACTCGGGTTTAGAACATGGTCCGTGTCCGTCGGGTCTCCGACCCTCGTCGAGATGTT
                                        ■━━━━━━━━ Furin Linker ━━━━━━━■ start ■
 P  S  N  T  K  V  D  K  K  V  E  P  K  S  C  T  R  H  R  Q  P  R  G  W  E  Q  L  Y  N CACTGTGTCATTTAACCTTGGAGAAGCTTATGAGTACCCCACTTTTATACAAGATTTGCGCAATGAATTGGCTAAGGGCACACCA
                                                                                    935
GTGACACAGTAAATTGGAACCTCTTCGAATACTCATGGGGTGAAAATATGTTCTAAACGCGTTACTTAACCGATTCCCGTGTGGT ■━━━━━━ start of De-Bouganin156 ━━━━━▶
   T  V  S  F  N  L  G  E  A  Y  E  Y  P  T  F  I  Q  D  L  R  N  E  L  A  K  G  T  P

GTATGTCAACTTCCAGTGACACT

Figure 23 (cont'd)

```
GGGTTGTAAATAAAGTGAGTCAAATTAGTCCCGATATGGGTATCCTTAAGTTTAAAAGCTCCAAATAGTGA
                                                                      1601
CCCAACATTTATTTCACTCAGTTTAATCAGGGCTATACCCATAGGAATTCAAATTTTCGAGGTTTATCACT
```

⊢━━━ end of De-Bouganin156 ━━━⊣

```
CTAGAGTCGACCTGCAGGTCTATGGAACGATAAATGCCCATGAAAATTCTATTTCAAGGAGACAGTCATAATGAAATACCTATTG
|----+----|----+----|----+----|----+----|----+----|----+----|----+----|----+----|----+  85
GATCTCAGCTGGACGTCCAGATACCTTGCTATTTACGGGTACTTTTAAGATAAAGTTCCTCTGTCAGTATTACTTTATGGATAAC
                                                                    |———— PelB ————
                                                                     M  K  Y  L  L

CCTACGGCAGCCGCTGGATTGTTATTACTCGCTGCCCAACCAGCGATGGCGCATCACCATCACCATCACTATGAGCTGACTCAGC
|----+----|----+----|----+----|----+----|----+----|----+----|----+----|----+----|----+ 170
GGATGCCGTCGGCGACCTAACAATAATGAGCGACGGGTTGGTCGCTACCGCGTAGTGGTAGTGGTAGTGATACTCGACTGAGTCG
————————————— PelB ——————————————|—— 6xHis ——|—— start of VL ——
  P  T  A  A  A  G  L  L  L  L  A  A  Q  P  A  M  A  H  H  H  H  H  H  Y  E  L  T  Q CACCCTCAGTGTCCGTGTCCCCAGGACAGAAAGCCTTCATAACCTGCTCTGGAGATAACCTGGGGAATAAATATGTGTGCTGGTA
|----+----|----+----|----+----|----+----|----+----|----+----|----+----|----+----|----+ 255
GTGGGAGTCACAGGCACAGGGGTCCTGTCTTTCGGAAGTATTGGACGAGACCTCTATTGGACCCCTTATTTATACACACGACCAT
———————— start of VL ——————
  P  P  S  V  S  V  S  P  G  Q  K  A  F  I  T  C  S  G  D  N  L  G  N  K  Y  V  C  W  Y TCAACAGAAGCCAGGCCAGTCCCCTGTCCTGGTCATCTATGAAGATACCAAGAGGCCCTCAGGGATCCCTGAGCGATTCTCTGCC
|----+----|----+----|----+----|----+----|----+----|----+----|----+----|----+----|----+ 340
AGTTGTCTTCGGTCCGGTCAGGGGACAGGACCAGTAGATACTTCTATGGTTCTCCGGGAGTCCCTAGGGACTCGCTAAGAGACGG Q  Q  K  P  G  Q  S  P  V  L  V  I  Y  E  D  T  K  R  P  S  G  I  P  E  R  F  S  A TCCAACTCTGGGAATACAGCCACTCTGACCATCAGCGGGACGCAGCCTATAGATGAGGCTGACTACTACTGTCAGGCGTGGGACA
|----+----|----+----|----+----|----+----|----+----|----+----|----+----|----+----|----+ 425
AGGTTGAGACCCTTATGTCGGTGAGACTGGTAGTCGCCCTGCGTCGGATATCTACTCCGACTGATGATGACAGTCCGCACCCTGT S  N  S  G  N  T  A  T  L  T  I  S  G  T  Q  P  I  D  E  A  D  Y  Y  C  Q  A  W  D GCCGCACTGAAATCTTCGGAACTGGGACCAAGGTCACCGTCCTAAGTCAGCCCAAGGCCAACCCCACTGTCACTCTGTTCCCGCC
|----+----|----+----|----+----|----+----|----+----|----+----|----+----|----+----|----+ 510
CGGCGTGACTTTAGAAGCCTTGACCCTGGTTCCAGTGGCAGGATTCAGTCGGGTTCCGGTTGGGGTGACAGTGAGACAAGGGCGG
                 |——— end of VL ———|——— start of CL ———
  S  R  T  E  I  F  G  T  G  T  K  V  T  V  L  S  Q  P  K  A  N  P  T  V  T  L  F  P  P CTCCTCTGAGGAGCTCCAAGCCAACAAGGCCACACTAGTGTGTCTGATCAGTGACTTCTACCCGGGAGCTGTGACAGTGGCCTGG
|----+----|----+----|----+----|----+----|----+----|----+----|----+----|----+----|----+ 595
GAGGAGACTCCTCGAGGTTCGGTTGTTCCGGTGTGATCACACAGACTAGTCACTGAAGATGGGCCCTCGACACTGTCACCGGACC S  S  E  E  L  Q  A  N  K  A  T  L  V  C  L  I  S  D  F  Y  P  G  A  V  T  V  A  W AAGGCAGATGGCAGCCCCGTCAAGGCGGGAGTGGAGACCACCAAACCCTCCAAACAGAGCAACAACAAGTACGCGGCCAGCAGCT
|----+----|----+----|----+----|----+----|----+----|----+----|----+----|----+----|----+ 680
TTCCGTCTACCGTCGGGGCAGTTCCGCCCTCACCTCTGGTGGTTTGGGAGGTTTGTCTCGTTGTTGTTCATGCGCCGGTCGTCGA K  A  D  G  S  P  V  K  A  G  V  E  T  T  K  P  S  K  Q  S  N  N  K  Y  A  A  S  S ACCTGAGCCTGACGCCCGAGCAGTGGAAGTCCCACAGAAGCTACAGCTGCCAGGTCACGCATGAAGGGAGCACCGTGGAGAAGAC
|----+----|----+----|----+----|----+----|----+----|----+----|----+----|----+----|----+ 765
TGGACTCGGACTGCGGGCTCGTCACCTTCAGGGTGTCTTCGATGTCGACGGTCCAGTGCGTACTTCCCTCGTGGCACCTCTTCTG Y  L  S  L  T  P  E  Q  W  K  S  H  R  S  Y  S  C  Q  V  T  H  E  G  S  T  V  E  K  T
```

Figure 24 (cont'd)

```
AGTGGCCCCTACAGAATGTTCATAGTGACTCGAG
                                    → 799
TCACCGGGGATGTCTTACAAGTATCACTGAGCTC
        ┣━━━━end of CL━━━━┫
   V  A  P  T  E  C  S
```

Figure 25

VB6-008-modified bouganin

CD44E TUMOR SPECIFIC ANTIBODY

FIELD OF THE INVENTION

The invention relates to human tumor-specific binding proteins and all uses thereof. In particular, the invention relates to antibodies or antibody fragments specific for antigens or molecules on cancer cells and to immunoconjugates comprising the binding proteins of the invention, and methods of use thereof.

BACKGROUND OF THE INVENTION

In the year 2000, an estimated 22 million people were suffering from cancer worldwide and 6.2 millions deaths were attributed to this class of diseases. Every year, there are over 10 million new cases and this estimate is expected to grow by 50% over the next 15 years (WHO, World Cancer Report. Bernard W. Stewart and Paul Kleihues, eds. IARC Press, Lyon, 2003). Current cancer treatments are limited to invasive surgery, radiation therapy and chemotherapy, all of which cause either potentially severe side-effects, non-specific toxicity and/or traumatizing changes to ones body image and/or quality of life. Cancer can become refractory to chemotherapy reducing further treatment options and likelihood of success. The prognosis for some cancer is worse than for others and some, like lung or pancreatic cancer are almost always fatal. In addition, some cancers with a relatively high treatment success rate, such as breast cancer, also have a very high incidence rate and, thus, remain major killers.

For instance, there are over 1 million new cases of breast cancer, worldwide, each year. Treatments consist of minimal to radical surgical removal of breast tissue and lymph nodes with radiation and chemotherapy for metastatic disease. Prognosis for localized disease is relatively good with a 5 years survival rate of around 50% but once the cancer has metastasized, it is incurable with an average survival of around 2 years. Despite improving treatment success rates, nearly 400,000 women die of breast cancer each year, the highest number of deaths to cancer in woman, ahead of deaths to lung cancer. Among the short and long term survivors, most will suffer the life-long trauma of the invasive and disfiguring surgical treatment.

Another example is liver cancer, with more than half a million new cases each year and nearly the same number of deaths due to poor treatment efficacy. Hepatocellular carcinomas represent around 80% of all liver cancers and are rarely curable. Five-year survival rate is only about 10% and survival after diagnosis often less than 6 months. Although surgical resection of diseased tissue can be effective, it is not an option for the majority of cases because of the presence of cirrhosis of the liver. Hepatocellular carcinomas are largely radiation resistant and response to chemotherapy is poor.

Yet another example is that of pancreatic cancer with around 200,000 new cases per year and a very poor prognosis. In fact, the majority of patients die within a year of diagnosis and only a few percent of patients survive five years. Surgery is the only available treatment but is associated with high morbidity and complication rates because it involves not only the resection of at least part of the pancreas, but also of all of the duodenum, part of the jejunum, bile duct and gallbladder and a distal gastrectomy. In some cases, the spleen and lymph nodes are also removed.

Bladder cancer is the 9th most common cancer worldwide with an estimated 330,000 new cases and 130,000 deaths each year. In Europe, this disease is the cause of death for approximately 50,000 people each year. Current treatment includes the intravesicular delivery of chemotherapy and immunotherapy with the bacille Calmette-Guerin (BCG) vaccine that involves the additional risk of systemic infection with the tuberculosis bacterium. Despite this aggressive treatment regime, 70% of these superficial papillary tumors will recur over a prolonged clinical course some will progress into invasive carcinomas. The high rate of recurrence of this disease and associated repeated course of treatment makes this form of cancer one of the most expensive to treat over a patient's lifetime. For patients with recurring disease, the only options are to undergo multiple anesthetic-requiring cystoscopy surgery or major, radical, life-altering surgery (usually cystectomy). Radical cystectomy consists of excision of the bladder, prostate and seminal vesicle in males and of the ovaries, uterus, urethra and part of the vagina in females.

There are many more examples of cancer where current treatments do not meet the needs of patients either due to their lack of efficacy and/or because they have high morbidity rates and severe side-effects. Those selected statistics and facts however, illustrate well the need for cancer treatments with better safety and efficacy profiles.

One of the causes for the inadequacy of current cancer treatments is their lack of selectivity for affected tissues and cells. Surgical resection always involves the removal of apparently normal tissue as a "safety margin" which can increase morbidity and risk of complications. It also always removes some of the healthy tissue that may be interspersed with tumor cells and that could potentially maintain or restore the function of the affected organ or tissue. Radiation and chemotherapy will kill or damage many normal cells due to their non-specific mode of action. This can result in serious side-effects such as severe nausea, weight loss and reduced stamina, loss of hair etc., as well as increasing the risk of developing secondary cancer later in life. Treatment with greater selectivity for cancer cells would leave normal cells unharmed thus improving outcome, side-effect profile and quality of life.

The selectivity of cancer treatment can be improved by using antibodies that are specific for molecules present only or mostly on cancer cells. Such antibodies can be used to modulate the immune system and enhance the recognition and destruction of the cancer by the patient's own immune system. They can also block or alter the function of the target molecule and, thus, of the cancer cells. They can also be used to target drugs, genes, toxins or other medically relevant molecules to the cancer cells. Such antibody-drug complexes are usually referred to as immunotoxins or immunoconjugates and a number of such compounds have been tested in recent year [Kreitman R J (1999) Immunotoxins in cancer therapy. Curr Opin Immunol 11:570-578; Kreitman R J (2000) Immunotoxins. Expert Opin Pharmacother 1:1117-1129; Wahl R L (1994) Experimental radioimmunotherapy. A brief overview. Cancer 73:989-992; Grossbard M L, Fidias P (1995) Prospects for immunotoxin therapy of non-Hodgkin's lymphoma. Clin Immunol Immunopathol 76:107-114; Jurcic J G, Caron P C, Scheinberg D A (1995) Monoclonal antibody therapy of leukemia and lymphoma. Adv Pharmacol 33:287-314; Lewis J P, DeNardo G L, DeNardo S J (1995) Radioimmunotherapy of lymphoma: a UC Davis experience. Hybridoma 14:115-120; Uckun F M, Reaman G H (1995) Immunotoxins for treatment of leukemia and lymphoma. Leuk Lymphoma 18:195-201; Kreitman R J, Wilson W H, Bergeron K, Raggio M, Stetler-Stevenson M, FitzGerald D J, Pastan I (2001) Efficacy of the anti-CD22 recombinant immunotoxin BL22 in chemotherapy-resistant hairy-cell leukemia. N Engl J Med 345:241-247]. Most antibodies tested to date have been raised against known cancer markers in the form of mouse monoclonal antibodies, sometimes "humanized" through molecular engineering. Unfortunately, their targets can also be present in significant quantities on a subset of normal cells thus raising the risk of non-specific toxic effects. Furthermore, these antibodies are basically mouse proteins that are being seen by the human patient's immune system as foreign proteins. The ensuing immune reaction and antibody response can result in a loss of efficacy or in side-effects.

The inventors have used a different approach in their development of antibodies for cancer treatment. Instead of immunizing experimental animals with cancer cells or isolated cancer cell markers, they have sought out only those markers that are recognized by the patient's own immune system or, in other words, that are seen by the immune system as a foreign molecule. This implies that the markers or antigens are usually substantially absent on normal cells and, thus, the risk of non-specific toxicity is further reduced. Hybridoma libraries are generated from cancer patient-derived lymphocytes and the antibodies they secrete are tested for binding to normal and tumor cells. Only antibodies showing high selectivity for cancer cells are retained for further evaluation and development as a cancer therapeutic or diagnostic agent. One such highly selective antibody is the subject of this patent application. In addition to being selective, this antibody is fully compatible with the patient's immune system by virtue of being a fully-human protein. The antibody of the invention can be used for diagnostic or therapeutic uses or as a basis for engineering other binding molecules for the target antigen.

The basic structure of an antibody molecule consists of four protein chains, two heavy chains and two light chains. These chains are inter-connected by disulfide bonds. Each light chain is comprised of a light chain variable region and a light chain constant region. Each heavy chain is comprised of a heavy chain variable region and a heavy chain constant region. The light chain and heavy chain variable regions can be further subdivided into framework regions and regions of hypervariability, termed complementarity determining regions (CDR). Each light chain and heavy chain variable region is composed of three CDRs and four framework regions.

CD44 represents a family of cell surface glycoproteins encoded by a single gene comprising a total of 20 exons. Exons 19 and 20 are expressed together as the cytoplasmic tail and therefore grouped as "exon 19" by most research groups (Liao et al. J. Immunol 151:6490-99, 1993). The term exon 19 will be used henceforth to designate genomic exons 19 and 20. Structural and functional diversity is achieved by alternative splicing of the messenger RNA involving 10 "variant" exons identified as exons 6-15 or, most often, as "variant exons" 1-10 (v1-v10). In human, variant exon 1 contains a stop codon and is not usually expressed. The longest potential CD44 variant is therefore CD44v2-10 (see Naor et al. Adv Cancer Res 71:241-319, 1997 for review of CD44).

Exons 1-5 and all variant exons are part of the extracellular domain and contain many potential sites for post-translational modifications. The transmembrane domain is highly conserved across species but the intracellular tail can be truncated leading to another type of variant. One such variant comprises variant exons 8-10 but lacks part of exon 19. Changes to the intracellular domain has been shown to change the function of CD44, in part with respect to binding and internalization of hyaluronic acid (HA). CD44 is not only involved in binding to the extracellular molecules but it also has cell signaling properties (see Turley et al. J Biol Chem 277(7):4589-4592, 2002 for review).

The "standard" CD44 (CD44s), the most commonly expressed form of CD44, contains exons 1-5 and 16-19 and none of the variant exons. The molecular weight for the core protein is 37-38 kDa but posttranslational modification can result in a molecule of 85-95 kDa or more (Drillenburg et al., Blood 95(6):1900, 2000). It binds hyaluronic acid (HA), an extracellular glycosaminoglycan, constitutively and CD44 is often referred to as the HA receptor. It is interesting that the presence of variant exons can reduce the binding of HA by CD44 such that CD44 variants cannot be said to constitutively bind HA but such binding can be inducible (reviewed in Naor et al. Adv Cancer Res 71:241-319, 1997). See FIG. 17 for some examples of variants.

CD44E, also called CD44v8-10, contains variant exons 8-10 in addition to the exons 1-5 and 16-19. Other variants include CD44v3-10, CD44v6, CD44v7-8 and many others. The variant exons are part of the extracellular domain of the CD44.

CD44E can be present on certain normal epithelial cells, particularly by generative cells of the basal cell of stratified squamous epithelium and of glandular epithelium (Mackay et al. J Cell Biol 124(1-2):71-82, 1994) and in the fetus at certain stages development. But importantly, it has been shown to be overexpressed on various types of cancer cells. Using RT-PCR, Iida & Bourguignon (J Cell Physiol 162(1):127-133, 1995) and Kalish et al. (Frontiers Bioscience 4(a):1-8, 1999) have shown that CD44E is present in normal breast tissue and is more abundant than CD44s. They have also shown that CD44, including CD44E and CD44s are overexpressed, and preferentially located in metastatic breast cancer tissues. Miyake et al. (J Urol 167(3):1282-87, 2002) reported that CD44v8-10 mRNA is strongly expressed in urothelial cancer and can even be detected in urinary exfoliated cells of patients with invasive vs superficial urothelial cancer. The ratio of CD44v8-10 to CD44v10 mRNA increases in cancer and was shown to have diagnostic value in breast, lung, laryngeal and bladder. The presence of CD44v8-10 was also confirmed by immunohistochemistry with a polyclonal antibody (Okamoto et al. J Natl Cancer Inst 90(4): 307-15, 1997). CD44v8-10 can also be overexpressed in gallbladder cancer (Yamaguchi et al. Oncol Rep 7(3):541-4, 2000), renal cell carcinoma (Hara et al. Urology 54(3):562-6, 1999), testicular germ cell tumors (Miyake et al. Am J Pathol 152(5):1157-60, 1998), non-small cell lung carcinomas (Sasaki et al. Int J Oncol 12(3):525-33, 1998), colorectal cancer (Yamaguchi et al. J Clin Oncol 14(4):1122-27, 1996) and gastric cancer (Yamaguchi et al. Jpn J Cancer Res 86(12): 1166-71, 1995). Overexpression of CD44v8-10 was also shown to have diagnostic value for prostate cancer (Martegani et al. Amer J Pathol 154(1): 291-300, 1999).

Alpha-fetoprotein (AFP) is a major serum protein synthesized during fetal life. Its presence in adults is usually indicative of carcinomas, particularly those of the liver and teratocarcinomas. It is part of the albuminoid gene family that also comprises serum and alpha albumins and vitamin D-binding protein. AFP comprises 590 amino acids for a molecular weight of about 69-70 kDa and has one site for glycosylation. (Morinaga et al., Proc Natl Acad Sci 80:4604-08, 1983; Mizejewski Exp Biol Med 226(5):377-408, 2002). Molecular variants have been studied and identified in rodents, but in humans there are no reports of variant proteins being detected. A recent report has identified a variant mRNA that, if expressed, would code for a 65 kDa protein. This protein is expected to remain in the cytoplasm (Fukusawa et al. J Soc Gynecol Investig May 20, e-publication, 2005).

SUMMARY OF THE INVENTION

The present inventors have prepared human tumor-specific antibodies that bind to several types of tumor cells including bladder, breast, ovary, prostate and uterus. Importantly, the antibodies do not significantly bind to normal tissue making them suitable candidates for tumor therapy. The inventors have cloned and sequenced the antibodies and determined the sequence of the antibody light and heavy chain variable regions and complementarity determining regions 1, 2 and 3. Accordingly, the invention provides isolated light chain complementarity determining regions 1, 2 and 3, comprising the amino acid sequences SGDNLGNKYVC (SEQ ID NO:1), EDTKRPS (SEQ ID NO:2) and QAWDSRTEI (SEQ ID NO:3), respectively; and isolated heavy chain complementarity determining regions 1, 2 and 3, comprising the amino acid sequences GDEYYWS (SEQ ID NO:4), YMSYRGSSYYSPSLQS (SEQ ID NO:5) and KYCGGD-CRSGFDI (SEQ ID NO:6), respectively.

The invention also provides isolated nucleic acid sequences encoding light chain complementarity determining regions 1, 2 and/or 3, comprising the amino acid sequences SGDNLGNKYVC (SEQ ID NO:1), EDTKRPS (SEQ ID NO:2) and QAWDSRTEI (SEQ ID NO:3), respectively; and isolated nucleic acid sequences encoding heavy chain complementarity determining regions 1, 2 and/or 3, comprising the amino acid sequences GDEYYWS (SEQ ID NO:4), YMSYRGSSYYSPSLQS (SEQ ID NO:5) and KYCGGDCRSGFDI (SEQ ID NO:6), respectively.

Additional aspects of the invention are isolated light chain variable regions comprising light chain complementarity determining regions 1, 2 and/or 3 of the invention (SEQ ID NOS:1-3), and isolated heavy chain variable regions comprising heavy chain complementarity determining regions 1, 2 and/or 3 of the invention (SEQ ID NOS:4-6). In one embodiment, the light chain variable region comprises the amino acid sequence shown in FIG. 1 (SEQ ID NO:7). In another embodiment, the heavy chain variable region comprises the amino acid sequence shown in FIG. 2 (SEQ ID NO:9).

The invention also provides an isolated nucleic acid sequence encoding the light chain variable region of the invention, and an isolated nucleic acid sequence encoding the heavy chain variable region of the invention. In one embodiment, the light chain variable region comprises the nucleic acid sequence shown in FIG. 1 (SEQ ID NO: 8). In another embodiment, the heavy chain variable region comprises the nucleic acid sequence shown in FIG. 2 (SEQ ID NO:10).

Another aspect of the invention is a binding protein, preferably an antibody or antibody fragment, that comprises at least one light chain complementarity determining region of the invention (i.e. one or more of the SEQ ID NOS:1-3) and/or at least one heavy chain complementarity determining region of the invention (i.e. one or more of SEQ ID NO:4-6). The invention also provides a binding protein, preferably an antibody or antibody fragment that comprises the light chain variable regions of the invention and/or the heavy chain variable regions of the invention.

The inventors have also identified the antigen that binds to the binding proteins of the invention. Accordingly, the invention provides the binding protein of the invention that binds to a protein comprising the 5-v8 interface of CD44E, the v8 exon of CD44 or amino acid sequence ATNMDSSHSIT. The invention also provides a binding protein of the invention that binds to CD44E; alpha-fetoprotein; a protein having a molecular weight between 47-53 kDa and an isoelectric point between 5.2-5.5, preferably 5.4; a protein having a molecular weight between 48-54 kDa and an isoelectric point between 5.1-5.4, preferably 5.2; or a protein comprising the amino acid sequence 107 to 487 of AFP (SEQ ID NO:14), 107 to 590 of AFP (SEQ ID NO: 15) or 107 to 609 of AFP (SEQ ID NO:16).

In addition, the invention provides compositions comprising the binding proteins of the invention, such as antibodies and antibody fragments, with a pharmaceutically acceptable excipient, carrier, buffer or stabilizer.

Another aspect of the invention is an immunoconjugate comprising (1) binding protein of the invention, preferably an antibody or antibody fragment that binds to an antigen or molecule on or in a cancer cell, attached to (2) an effector molecule. A further aspect of the invention is an immunoconjugate comprising (1) binding protein of the invention, preferably an antibody or antibody fragment that binds to an antigen or molecule that is internalized by a cancer cell, attached to (2) an effector molecule. In a preferred embodiment, the effector molecule is (i) a label, which can generate a detectable signal, directly or indirectly, or (ii) a cancer therapeutic agent, which is either cytotoxic, cytostatic or otherwise prevents or reduces the ability of the cancer cells to divide and/or metastasize. Preferably, the cancer therapeutic agent is a toxin.

The invention also provides compositions comprising the immunoconjugate of the invention and uses of the immunoconjugate for the manufacture of a medicament for treating or preventing cancer, and diagnostic purposes. In addition, the invention provides methods of treating or preventing cancer using the immunoconjugate of the invention and related kits.

A further aspect of the invention is a method of diagnosing cancer in a mammal comprising the steps of:
(1) contacting a test sample taken from said mammal with a binding protein of the invention that binds to an antigen on or in the cancer cell under conditions that permit the formulation of a binding protein-antigen complex;
(2) measuring the amount of binding protein-antigen complex in the test sample; and
(3) comparing the amount of binding protein-antigen complex in the test sample to a control.

The invention also includes a method of diagnosing cancer in a mammal comprising the steps of:
(1) contacting a test sample taken from said mammal with a binding protein of the invention that binds specifically to alpha-fetoprotein or a variant thereof under conditions that permit the formulation of a binding protein-alpha-fetoprotein complex;
(2) measuring the amount of binding protein-alpha-fetoprotein complex in the test sample; and
(3) comparing the amount of binding protein-alpha-fetoprotein complex in the test sample to a control.

Another aspect of the invention is a diagnostic agent comprising the immunoconjugate of the invention, wherein the effector molecule is a label, which can generate a detectable signal, directly or indirectly.

The invention also includes an isolated protein that can specifically bind with one of the binding proteins of the invention, nucleic acid sequences and uses thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 is the nucleic acid and amino acid sequence of the light chain variable region of VB1-008.

FIG. 2 is the nucleic acid and amino acid sequence of the heavy chain variable region of VB1-008.

FIG. 8 is a demonstration of antibody cell surface binding after incubation of A-375 cells at different temperatures as determined by flow cytometry. Fluorescence labeling of A-375 cells after incubation of cell suspensions at 4° C.: 4B5 (1) and VB1-008 (2) Fluorescence labeling of A-375 cells after warming antibody-bound cells to 37° C.: VB1-008 for 60 min (3), for 120 min (4).

FIG. 9 shows confocal microscopy assessment of VB1-008 internalization. A-375 cells were incubated with antibody at 4° C., washed and warmed to 37° C. for 60 min. Cells were fixed, permeabilized and labeled with fluorescent-labeled second antibody. Fluorescence labeling of A-375 cells after incubation of VB1-008 at 4° C. for 60 min, displaying circumferential surface distribution of labeling, (60××4) magnification (A). Following incubation of antibody-bound cells at 37° C. for 60 min the cells show strong intracellular staining by internalized antibody, (60××4) magnification (B).

FIG. 10A shows the results of the experiment under non-reducing conditions, while FIGS. 10B and C show the results of the experiment under reducing conditions.

FIGS. 11A and B show the presence of two distinct protein spots in the purified antigen complex, very close in molecular weight. The proteins were probably not perceived as two bands in 1D-PAGE due to protein stacking. FIG. 11A represents the western blot profile of the 2D-gel and FIG. 11B represents the Coomassie stained counterpart.

FIGS. 12A and B show the mapping of the peptides obtained and the sequence coverage of the original AFP molecule, Accession #GI|4501989. FIG. 12A shows the mapping of peptides obtained from the 2D gel (SEQ ID NO: 76). The amino acids in bolded font represent the sequences of amino acids identified from MS analysis. The shaded regions represent the homology of peptide sequences and thereby depict the sequence coverage. FIG. 12B shows the complete mapping of the peptides obtained from the 1D and 2D gels (SEQ ID NO: 77). The amino acids in bolded font represent the sequences of amino acids from MS analysis. The shaded regions represent the homology of peptide sequences and thereby detect the sequence coverage. The underlined amino acids were not detected.

FIG. 13 shows immunopurification of the VB1-008 antigen using 1000 μg of MDA-MB-435S membranes as the source. The purified antigen(s) was resolved on SDS-PAGE under non-reducing sample conditions. Reducing agents such as DTT or β-mercaptoethanol were avoided so as to preserve the native conformation of the binding antigen(s). The sample was resolved on two lanes of the gel. One lane (A), was stained for protein; the other (B) was subjected to western blotting and probed with VB1-008, to ensure the presence of the specific antigen. Band "E" from the coomassie stained portion of the gel was excised and sent for MS analysis.

FIG. 14 shows the complete mapping of the peptides obtained and the sequence coverage of CD44 molecule, Accession #GI|105583 (SEQ ID NO: 78). The amino acids in red font represent the sequences of amino acids identified from MS analysis. The shaded regions represent the homology of peptide sequences and thereby depict the sequence coverage. The amino acids in underlined area constitute the variable region (v8-v10) characteristic of the isoform3 or CD44E.

FIG. 18A depicts the amino acid sequence of CD44E (SEQ ID NOS: 79 & 80). The highlighted portion represents the stretch of 17 amino acids used to generate peptides 1-3. The negative control peptide is highlighted in the C-terminal region of the protein. FIG. 18B shows the results of a binding experiment with VB1-008 to peptides 1-3.

FIG. 20 shows the nucleotide sequence of the immunoconjugate VB6-008 (SEQ ID NO:11). The sequence of the PelB leader sequence is in lower case with the initiation codon bolded. The stop codes are in uppercase and bolded.

FIG. 21 shows the amino acid sequences of the heavy chain and light chain of the immunoconjugate VB6-0008 (SEQ ID NO:12 and 13).

FIG. 23 shows the VB6-008 unit #1, which includes the PeIB-VH-CH-Furin-De-Bouganin (SEQ ID NOS: 8284 and 85).

FIG. 24 shows the VB6-008 #2 unit which consists of PeIB-VL-CL (SEQ ID NOS: 86 and 87).

FIG. 25 shows the results of an in vitro cytotoxicity experiment using VB6-008.

Figure 3:
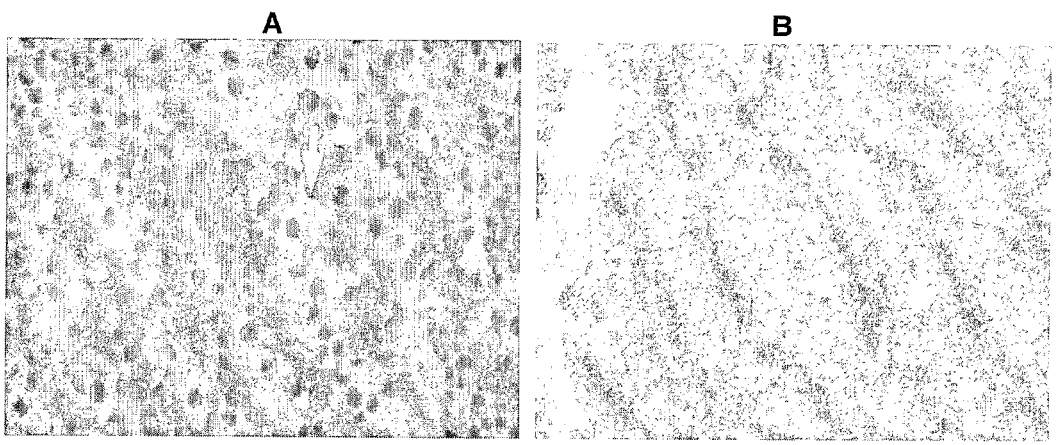
FIG. 3 is SKBR-3 (400× mag) fixed-cell pellet stained with VB1-008 (A) and the isotype control antibody 4B5 (B). Notice prominent membrane staining (arrow).

DETAILED DESCRIPTION OF THE INVENTION (A) Definitions

The term "administered systemically" as used herein means that the immunoconjugate and/or other cancer therapeutic may be administered systemically in a convenient manner such as by injection (subcutaneous, intravenous, intramuscular, etc.), oral administration, inhalation, transdermal administration or topical application (such as topical cream or ointment, etc.), suppository applications, or means of an implant. An implant can be of a porous, non-porous, or gelatinous material, including membranes, such as sialastic membranes, or fibers. Suppositories generally contain active ingredients in the range of 0.5% to 10% by weight.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', $F(ab')_2$, scFv, dsFv, ds-scFv, dimers, minibodies, diabodies, and multimers thereof and bispecific antibody fragments. Antibodies can be fragmented using conventional techniques. For example, $F(ab')_2$ fragments can be generated by treating the antibody with pepsin. The resulting $F(ab')_2$ fragment can be treated to reduce disulfide bridges to produce Fab' fragments. Papain digestion can lead to the formation of Fab fragments. Fab, Fab' and $F(ab')_2$, scFv, dsFv, ds-scFv, dimers, minibodies, diabodies, bispecific antibody fragments and other fragments can also be synthesized by recombinant techniques.

The term "antibody or antibody fragment of the invention" as used herein comprises at least one light chain complementarity determining region of the invention (i.e. one or more of SEQ ID NOS:1-3) and/or at least one heavy chain complementarity determining region of the invention (i.e. one or more of SEQ ID NOS:4-6). Preferably, the antibody or antibody fragment comprises the light chain CDR sequences (SEQ ID NOS:1-3) and/or the heavy chain CDR sequences (SEQ ID NOS:4-6) or functional variants of the sequences so that the antibody or antibody fragment can bind to the tumor cell without substantially binding to normal cells. Antibodies or antibody fragments of the invention also include antibodies or antibody fragments that bind to CD44E; alpha-fetoprotein; a protein having a molecular weight between 47-53 kDa and an isoelectric point between 5.2-5.5, preferably 5.4; a protein having a molecular weight between 48-54 kDa and an isoelectric point between 5.1-5.4, preferably 5.2; or a protein comprising the amino acid sequence 107 to 487 of AFP (SEQ ID NO:14), 107 to 590 of AFP (SEQ ID NO: 15) or 107 to 609 of AFP (SEQ ID NO:16). In addition, antibodies or antibody fragments of the invention include antibodies or antibody fragments that bind to a protein comprising the 5-v8 interface of CD44E, the v8 exon of CD44 or amino acid sequence ATNMDSSHSIT.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6(Log 10[Na+])+0.41(%(G+C)−600/1), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5× Denhardt's solution/1.0% SDS at Tm—5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

The term "binding protein" as used herein refers to proteins that specifically bind to another substance. In an embodiment, binding proteins are antibodies or antibody fragments.

The term "binding proteins of the invention" as used herein includes antibodies or antibody fragments of the invention.

By "biologically compatible form suitable for administration in vivo" is meant a form of the substance to be administered in which any toxic effects are outweighed by the therapeutic effects.

The term "cancer" as used herein includes any cancer that can be bound by a binding protein of the invention, preferably an antibody or antibody fragment of the invention.

Figure 17:
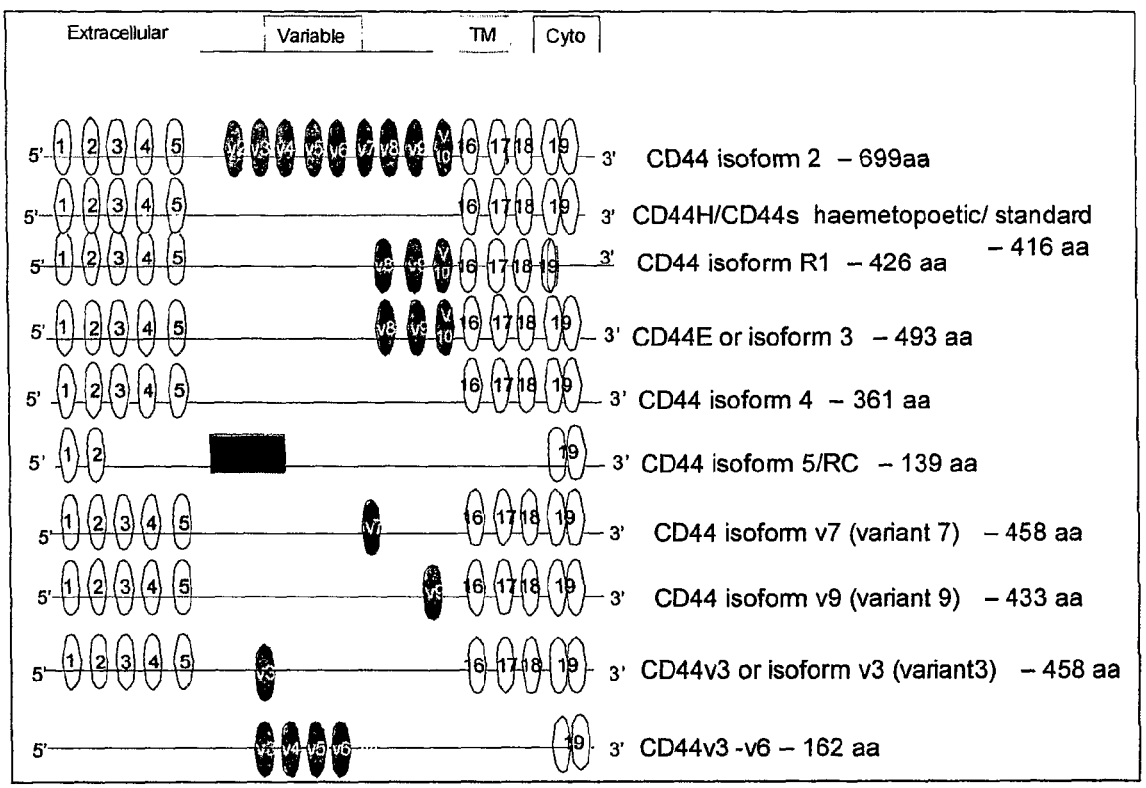
FIG. 17 is a schematic representation of the distribution of different exons in the CD44 gene in humans. Alternative splicing in the variable region results in the creation of a number of isoforms, a few of the reported isoforms are represented schematically in the corresponding figure.

The term "CD44" as used herein refers to the family of CD44 molecules encoded by a single gene comprising a total of 19 exons. There are 10 variable exons. Alternative splicing in the variable regions results in the creation of a number of different CD44 variants (See FIG. 17). The term "CD44E", also known as CD44v8-10, refers to the epithelial variant of CD44. CD44E contains variant exons 8-10 in addition to exons 1-5 and 16-19. The term "v8 exon of CD44" refers to variable exon 8 of CD44. The term "5-v8 interface of CD44E" refers to the region where exon 5 connects with variable exon 8 in CD44E. It is a continuous sequence that includes part of the region of exon 5 and part of the variable exon 8 of CD44E.

A "conservative amino acid substitution", as used herein, is one in which one amino acid residue is replaced with another amino acid residue without abolishing the protein's desired properties.

The term "controlled release system" as used means the immunoconjugate and/or other cancer therapeutic of the invention can be administered in a controlled fashion. For example, a micropump may deliver controlled doses directly into the area of the tumor, thereby finely regulating the timing and concentration of the pharmaceutical composition (see, e.g., Goodson, 1984, in Medical Applications of Controlled Release, vol. 2, pp. 115-138).

The term "direct administration" as used herein means the immunoconjugate and/or other cancer therapeutic may be administered, without limitation, intratumorally, intravascularly, and peritumorally. For example, the immunoconjugate may be administered by one or more direct injections into the tumor, by continuous or discontinuous perfusion into the tumor, by introduction of a reservoir of the immunoconjugate, by introduction of a slow-release apparatus into the tumor, by introduction of a slow-release formulation into the tumor, and/or by direct application onto the tumor. By the mode of administration "into the tumor," introduction of the immunoconjugate and/or other cancer therapeutic to the area of the tumor, or into a blood vessel or lymphatic vessel that substantially directly flows into the area of the tumor, is included.

As used herein, the phrase "effective amount" means an amount effective, at dosages and for periods of time necessary to achieve the desired result. Effective amounts of an immunoconjugate may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

The term "heavy chain complementarity determining region" as used herein refers to regions of hypervariability within the heavy chain variable region of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus.

The term "heavy chain variable region" as used herein refers to the variable region of a heavy chain.

The term "immunoconjugate of the invention" is used herein comprises (1) a binding protein, preferably an antibody or antibody fragment, of the invention attached to (2) an effector molecule. The effector molecule can be any molecule that one wishes to deliver to the cancer cell, including, but not limited to (i) a label, which can generate a detectable signal, directly or indirectly, or (ii) a cancer therapeutic agent, such as a toxin that is either cytotoxic, cytostatic or otherwise prevents or reduces the ability of the cancer cells to divide and/or metastasize.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

The term "isolated proteins", such as light chain complementarity regions 1, 2 and 3, heavy chain complementarity regions 1, 2 and 3, light chain variable regions, heavy chain variable regions, and binding proteins of the invention, refers to a protein substantially free of cellular material or culture medium when produced by recombinant DNA techniques, or chemical precursors or other chemicals when chemically synthesized.

The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable region of a light chain.

The term "modified bouganin" as used here means a modified bouganin that has a reduced propensity to activate an immune response as described in PCT/CA2005/000410 and U.S. patent application Ser. No. 11,084,080. In one example, the modified bouganin has the amino acid sequence (SEQ ID NO: 17):

```
YNTVSFNLGEAYEYPTFIQDLRNELAKGTPVCQLPVTLQTIADDKRFVLV

DITTTSKKTVKVAIDVTDVYVVGYQDKWDGKDRAVFLDKVPTVATSKLFP

GVTNRVTLTFDGSYQKLVNAAKADRKALELGVNKLEFSIEAIHGKTINGQ

EAAKFFLIVIQMVSEAARFKYIETEVVDRGLYGSFKPNFKVLNLENNWGD

ISDAIHKSSPQCTTINPALQLISPSNDPWVVNKVSQISPDMGILKFKSS

K.
```

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S. and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215: 403).

As used herein, the phrase "treating cancer" refers to inhibition of cancer cell replication, inhibition of cancer spread (metastasis), inhibition of tumor growth, reduction of cancer cell number or tumor growth, decrease in the malignant grade of a cancer (e.g., increased differentiation), or improved cancer-related symptoms.

The term "variant" as used herein includes modifications or chemical equivalents of the amino acid and nucleotide sequences of the present invention that perform substantially the same function as the proteins or nucleic acid molecules of the invention in substantially the same way. For example, variants of proteins of the invention include, without limitation, conservative amino acid substitutions. Variants of proteins of the invention also include additions and deletions to the proteins of the invention.

The term "variant of alpha-fetoprotein" includes variants of alpha-fetoprotein, such as a protein comprising the amino acid sequence of SEQ ID NO:14, 15 or 16; or a protein that is a truncated version of alpha-fetoprotein and has the molecular weight of 48-54 kDa and an isoelectric point between 5.1-5.4.

(B) Proteins and Nucleic Acids of the Invention (i) Light and Heavy Chain Complementarity Determining Regions And Light and Heavy Chain Variable Regions The invention provides isolated light chain complementarity determining region 1 comprising the amino acid sequence SGDNLGNKYVC (SEQ ID NO:1). The invention also provides isolated light chain complementarity determining region 2 comprising the amino acid sequence EDTKRPS (SEQ ID NO:2). In addition, the invention provides isolated light chain complementarity determining region 3 comprising the amino acid sequence QAWDSRTEI (SEQ ID NO:3).

The invention provides isolated light chain complementarity determining region 1 comprising the amino acid sequence GDEYYWS (SEQ ID NO:4). The invention also provides isolated light chain complementarity determining region 2 comprising the amino acid sequence YMSYRGSSYYSPSLQS (SEQ ID NO:5). In addition, the invention provides isolated light chain complementarity determining region 3 comprising the amino acid sequence KYCGGDCRSGFDI (SEQ ID NO:6).

The invention provides isolated light chain complementarity determining regions 1, 2 and 3, comprising the amino acid sequences SGDNLGNKYVC (SEQ ID NO:1), EDTKRPS (SEQ ID NO:2) and QAWDSRTEI (SEQ ID NO:3), respectively; and isolated heavy chain complementarity determining regions 1, 2 and 3, comprising the amino acid sequences GDEYYWS (SEQ ID NO:4), YMSYRGSSYYSPSLQS (SEQ ID NO:5) and KYCGGDCRSGFDI (SEQ ID NO:6), respectively.

The invention also includes variants of the CDR sequences that can bind to the same epitope or antigen recognized by the CDR sequences disclosed above.

Additional aspects of the invention are isolated light chain variable regions comprising light chain complementarity determining regions 1, 2 and/or 3 of the invention (SEQ ID NOS:1-3); and heavy chain variable regions comprising the heavy chain complementarity determining regions 1, 2 and/or 3 of the invention (SEQ ID NOS:4-6). In one embodiment, the light chain variable region comprises the amino acid sequence shown in FIG. 1 (SEQ ID NO:7), and the heavy chain variable region comprises the amino acid sequence shown in FIG. 2 (SEQ ID NO:9).

The invention also includes variants of the isolated light chain variable regions and heavy chain variable regions that can bind to the same epitope or antigen recognized by the isolated light chain variable regions and isolated heavy chain variable regions disclosed above.

A person skilled in the art will appreciate that the invention includes variants to the amino acid sequences of SEQ ID NOS:1-6, 7 and 9, including chemical equivalents to the sequences disclosed by the present invention. Such equivalents include proteins that perform substantially the same function as the specific proteins disclosed herein in substantially the same way. A functional variant of a CDR sequence will be able to bind to the antigen or epitope recognized by the native CDR sequence. For example, equivalents include, without limitation, conservative amino acid substitutions.

In one embodiment, the variant amino acid sequences of the light chain complementarity determining regions 1, 2 and 3, and the heavy chain complementarity determining regions 1, 2 and 3 have at least 50%, preferably at least 60%, more preferably at least 70%, most preferably at least 80%, and even more preferably at least 90% sequence identity to SEQ ID NOS:1-6, respectively.

In another embodiment, the variant amino acid sequences of the light chain variable region and the heavy chain variable region have at least 50%, preferably at least 60%, more preferably at least 70%, most preferably at least 80%, and even more preferably at least 90% sequence identity to SEQ ID NOS:7 and 9, respectively.

The invention also provides an isolated nucleic acid sequence encoding the light chain variable region of the invention, and an isolated nucleic acid sequence encoding the heavy chain variable region of the invention. In one embodiment, the light chain variable region comprises the nucleic acid sequence shown in FIG. 1 (SEQ ID NO: 8). In another embodiment, the heavy chain variable region comprises the nucleic acid sequence shown in FIG. 2 (SEQ ID NO:10). The invention also includes variants to the nucleic acid sequences that encode for the light chain variable region and heavy chain variable region of the invention. For example, the variants include nucleotide sequences that hybridize to the nucleic acid sequences encoding the light chain variable region and heavy chain variable region of the invention under at least moderately stringent hybridization conditions.

The invention also provides isolated nucleic acid sequences encoding light chain complementarity determining regions 1, 2 and/or 3, comprising the amino acid sequences SGDNLGNKYVC (SEQ ID NO:1), EDTKRPS (SEQ ID NO:2) and QAWDSRTEI (SEQ ID NO:3), respectively; and isolated nucleic acid sequences encoding heavy chain complementarity determining regions 1, 2 and/or 3, comprising the amino acid sequences GDEYYWS (SEQ ID NO:4), YMSYRGSSYYSPSLQS (SEQ ID NO:5) and KYCGGDCRSGFDI (SEQ ID NO:6), respectively. The invention also includes isolated nucleic acid sequences encoding variants of the CDR sequences discussed above. Nucleic acid sequences encoding variants of the CDR sequences of the invention include nucleic acid sequences that hybridize to the CDR sequences encoding the amino acid sequences shown in SEQ ID NOS:1-6 under at least moderately stringent hybridization conditions.

(ii) Binding Proteins

Another aspect of the invention is a binding protein, preferably an antibody or antibody fragment, that comprises at least one light chain complementarity determining region of the invention (i.e. one or more of SEQ ID NOS:1-3) and/or at least one heavy chain complementarity determining region of the invention (i.e. one or more of SEQ ID NOS:4-6). Such a binding protein can be generally referred to herein as "a binding protein of the invention", or preferably "an antibody or antibody fragment of the invention".

In one embodiment, the binding protein, preferably an antibody or antibody fragment, comprises the light chain complementarity determining regions 1, 2 and 3, comprising the amino acid sequences SGDNLGNKYVC (SEQ ID NO:1), EDTKRPS (SEQ ID NO:2) and QAWDSRTEI (SQ ID NO:3), respectively; and heavy chain complementarity determining regions 1, 2 and 3, comprising the amino acid sequences GDEYYWS (SEQ ID NO:4), YMSYRGSSYYSPSLQS (SEQ ID NO:5) and KYCGGD-CRSGFDI (SEQ ID NO:6), respectively. The invention also provides a binding protein, preferably an antibody or antibody fragment, that comprises the light chain variable region of the invention and/or the heavy chain variable region of the invention.

A person skilled in the art will appreciate that the invention includes variants to the specific binding proteins disclosed above, including chemical equivalents to the sequences disclosed above that perform substantially the same function as the binding proteins disclosed above in substantially the same way. A functional variant of a binding protein will be able to bind to a protein comprising 5-v8 interface of CD44E, the v8 exon of CD44, the amino acid sequence ATNMDSSHSIT, amino acid SEQ ID NOS:14, 15 or 16, or to a protein having a molecular weight between 47-53 kDa and an isoelectric point between 5.2-5.5; a protein having a molecular weight between 48-54 kDa and an isoelectric point between 5.1-5.4, CD44E, or alpha-fetoprotein or a variant thereof.

As stated above, the inventors have identified the antigen that binds to the binding protein of the invention. In particular, the inventors have shown that the binding proteins of the invention bind to the extracellular domain of CD44E. In addition, the inventors have shown that the binding proteins of the invention bind to AFP or a variant thereof.

It is important to recognize that CD44 molecules have a high potential for N- and O-glycosylation and for the addition of chondroitin sulfate and heparan sulfate. However, the pattern of these post-translational modifications is variable, and appears to be cell-specific and can potentially affect the ability of CD44 to bind HA or other extracellular molecules. The variable pattern of post-translational modifications is particularly relevant to the preparation of anti-CD44 monoclonal antibodies since antibody binding has been shown to be affected by the presence of these modifications, despite the primary structure of the molecule being the same as that of the antigen used to raise the antibody (Matzuki et al. Cancer Res 63:8278-83, 2003; Martegani et al. Amer J Pathol 154(1): 291-300, 1999). This also limits the usefulness of recombinant CD44 as an immunogen since its glycosylation pattern would likely differ from that of tumor cells. The binding proteins of the invention is, therefore, particularly unique since it recognizes a form of the CD44 that is present on human tumor cells.

Accordingly, the invention provides a binding protein of the invention that binds to a protein comprising the 5-v8 interface of CD44E, the v8 exon of CD44 or amino acid sequence ATNMDSSHSIT. The invention also provides a binding protein of the invention that binds to CD44E; alpha-fetoprotein; a protein having a molecular weight between 47-53 kDa and an isoelectric point between 5.2-5.5, preferably 5.4; a protein having a molecular weight between 48-54 kDa and an isoelectric point between 5.1-5.4, preferably 5.2; or a protein comprising the amino acid sequence 107 to 487 of AFP (SEQ ID NO:14), 107 to 590 of AFP (SEQ ID NO: 15) or 107 to 609 of AFP (SEQ ID NO:16). The invention also provides a binding protein of the invention that binds to a protein comprising SEQ ID NOS: 38, 39, 40, 41, 42, 43, 44 or 45 and having a molecular weight between 47-53 kDa and an isoelectric point between 5.2-5.5; or a protein comprising SEQ ID NOS: 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 and having a molecular weight between 48-54 kDa and an isoelectric point between 5.1-5.4.

The invention also includes binding proteins that bind to the amino acid sequence ATNMDSSHSIT.

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. Preferably, the light chain constant region is a lambda light chain constant region.

To produce monoclonal antibodies derived from humans, antibody producing cells (lymphocytes) can be harvested from a human having cancer and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., *Methods Enzymol,* 121: 140-67 (1986)), and screening of combinatorial antibody libraries (Huse et al., *Science* 246:1275 (1989)). Another example of making human monoclonal antibodies is described in WO/9947929. In another example, a myeloma-like fusion partner, as described in Dan et al. (J Neurosurgery 76:660-69, 1992) can be used. Hybridoma cells can be screened immunochemically for production of antibodies specifically reactive with cancer cells and the monoclonal antibodies can be isolated.

Specific antibodies, or antibody fragments, reactive against particular antigens or molecules, such as antigens or molecules on a cancer cell, may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., *Nature* 341:544-546 (1989); Huse et al., *Science* 246:1275-1281 (1989); and McCafferty et al., *Nature* 348:552-554 (1990)).

The present invention includes all antibodies and antibody fragments that bind to the same antigen as the antibodies or antibody fragments of the invention. A person skilled in the art will appreciate that binding assays can be used to find other antibodies and antibody fragments with the same binding specificities as the antibodies and antibody fragments of the invention. As exemplified, below, a competition binding assay can be used to find such other antibodies.

Before a competition assay is performed using flow cytometry, the minimal concentration of antibody of the invention (Ab1) that gives maximal binding against a fixed number of tumor cells (for example, A-375 cells for VB1-008) is determined. A total of $10^6$ cells are harvested from exponentially growing cultures and incubated with various antibody concentrations for 1 hr at 4° C. The cells are washed and incubated with a suitable detection antibody for an additional hour at 4° C. After washing, the cells are analyzed by flow cytometry. For each test antibody, a saturation curve is generated from the data by plotting median fluorescence against the antibody concentration.

For the competition assay, tumor cells are prepared as above and treated in duplicate with a fixed concentration of antibody (Ab1). The fixed concentration is the minimal concentration of antibody that generates maximal binding against a fixed number of tumor cells as determined above. Immediately following the addition of the Ab1, varying concentrations of the potential inhibitory antibody (Ab2) is added to each tube and the mixture incubated for 1 hr at 4° C. Both the percent inhibition and change over maximum median fluorescence are calculated by subtracting the background fluorescence (PBS-5% FCS) from the median fluorescence reading for each test sample (Ab1+Ab2). The result is then divided by the median fluorescence of Ab1 alone (maximal binding) minus the background (see below). The percent of inhibition result is obtained by multiplying by 100. The mean of the replicates along with their respective standard error is plotted against antibody concentration. The following formula is used to calculate the percent inhibition:

$$PI=[(MF_{(Ab1+Ab2)}-MF_{Bgd})/(MF_{Ab1}-MF_{Bgd})]\times 100$$

where PI=percent inhibition; $MF_{(Ab1+Ab2)}$=median fluorescence measured for Ab1+Ab2 mixture; and $MF_{Bgd}$=background median fluorescence with PBS-5% FCS.

Accordingly, the invention provides a binding protein capable of binding an antigen on a tumor cell wherein the binding protein can be identified by a method comprising:
(1) incubating a fixed number of tumor cells with a minimal concentration of a binding protein of the invention, preferably an antibody or antibody fragment (Ab1) that generates maximal binding against the fixed number of tumor cells and measuring median fluorescence of Ab1 ($MF_{Ab1}$);
(2) testing two or more concentrations of a test binding protein (Ab2) by adding Ab2 to the Ab1 and tumor cells, and measuring median fluorescence ($MF_{(Ab1+Ab2)}$);
(3) measuring background median fluorescence ($MF_{bgd}$);
(4) calculating PI, wherein $$PI=[(MF_{(Ab1+Ab2)}-MF_{Bgd})/(MF_{Ab1}-MF_{Bgd})]\times 100;$$
and (5) comparing the PI to a control PI value;
wherein, a PI that has a statistically significant difference from the control PI indicates that the test binding protein is capable of binding the antigen on the tumor cell.

The competition binding assay can also be done with peptides, preferably the peptide defined by SEQ ID NO:28. Similar to the method described above, before the competition assay is performed, the minimal concentration of test binding protein (Ab2) that gives maximal binding against a fixed number of tumor cells is determined.

Accordingly, an embodiment of the invention provides a binding protein capable of binding an antigen on a tumor cell wherein the binding protein can be identified by a method comprising:
(1) incubating a fixed number of tumor cells with a minimal concentration of a test binding protein (Ab2) that generates maximal binding against the fixed number of tumor cells and measuring median fluorescence of Ab2 ($MF_{Ab2}$);
(2) preparing a peptide and Ab2 mixture by incubating a molar excess of a peptide defined by SEQ ID NO:28 with said minimal concentration of the test binding protein (Ab2);
(3) adding said mixture to tumor cells and measuring median fluorescence ($MF_{(Ab2+peptide)}$);
(4) measuring background median fluorescence ($MF_{bgd}$);
(5) calculating PI, wherein $$PI=[(MF_{(Ab2+peptide)}-MF_{Bgd})/(MF_{Ab2}-MF_{Bgd})]\times 100;$$
and (6) comparing the PI to a control PI value;
wherein, a PI that has a statistically significant difference from the control PI indicates that the test binding protein is capable of binding the antigen on the tumor cell.

A person skilled in the art will appreciate that affinity maturation techniques could be used modify the binding proteins or immunoconjugates of the invention either by increasing its affinity for both CD44E and AFP or by selecting out the binding to one antigen. The latter can lead to the development of 2 separate antibodies or immunoconjugates with preferential binding to either AFP or to CD44E.

Two strategies are routinely used to enhance the binding affinity of an antibody. One approach utilizes the resolution of the crystal structure of the Ab-Ag complex to identify the key residues involved in the antigen binding (Davies D. R., Cohen G. H. 1996. Interactions of protein antigens with antibodies. Proc Natl. Acad. Sci. U.S.A. 93, 7-12). Subsequently, those residues can be mutated to enhance the interaction. The other approach mimics an in vivo antigen stimulation that drives the affinity maturation of immunoglobulin produced by B cells. During the maturation of the immune response, the variable regions of the immunoglobulins are subjected to somatic mutations (Mc Heyzer-Williams M. 2003. B-cell signaling mechanism and activation. Fundamental Immunology, Fifth edition, 195-225). This process, highly specific for the immune system, is characterized by the introduction of point mutations at a very high rate. It occurs only within the DNA fragments encoding the variable regions and excludes the conserved domains. The B cells expressing the somatically mutated variant antibody are then subjected to an antigen-mediated selection resulting in the selection of higher affinity immunoglobulin. In order to replicate this phenomenon in vitro, several approaches have been used to introduce mutations either by random or targeted processes. The random mutations can be introduced using error-prone PCR, chain shuffling or mutator E. coli strains (Clackson T. Hoogenboom N. R., Griffiths A. D. and Winter G. 1991 Making antibody fragments using phage display libraries. Nature 352, 624-628, Hawkins R. E., Russell S. J. and Winter G. 1992. Selection of phage antibodies by binding affinity. Mimicking affinity maturation. J. Mol. Biol. 226, 889-896, Low N., Holliger P. and Winter G. 1996. Mimicking somatic hypermutation: affinity maturation of antibodies displayed on bacteriophage using a bacterial mutator strain. J Mol. Biol. 260, 359-368). This strategy leads to the creation of large libraries in which reactive clones are selected with a display technology such as ribosome, phage or yeast (Min L. (2000). Applications of display technology in protein analysis. Nat. Biotechnol. 18, 1251-1256).

The targeted mutations of the CDRs, especially CDR3 of the light and heavy chains, have been shown to be an effective technique for increasing antibody affinity. Blocks of 3 to 4 amino acids of the CDR3 or specific regions called "hotspots" are targeted for mutagenesis. Yang et al reported an increase of 420 fold of an anti-HIV gp120 Fab fragment by mutating four CDR residues (Yang W. P., Green K., Pinz-Sweeney S., Briones A. T., Burton D. R. and Barbas C. F. III. 1995. CDR walking mutagenesis for the affinity maturation of a potent human anti-HIV-1 antibody into picomolar range. J. Mol. Biol., 254, 392-403). One mutation in the VL CDR3 combined with three mutations in the VH CDR3 of the C6.5 scFv yielded a 1230 fold increased affinity (Schier R., McCall A., Adams G. P., Marshall K. W., Merrit H., Yin M., Crawford R. S. Weiner L. M., Marks C. and Marks J. D. 1996. Isolation of picomolar affinity anti-c-erbB-2 single-chain Fv by molecular evolution of the complementary determining regions in the center of the antibody binding site. J. Mol. Biol., 263, 551-567).

"Hot spots" are the sequences where somatic hypermutation takes place in vivo (Neuberger M. S and Milstein C. 1995. Somatic hypermutation. Curr. Opin. Immunol. 7, 248-254). The hotspot sequences can be defined as consensus nucleotide sequences in certain codons. The consensus sequence is the tetranucleotide, RGYW, in which R can be either A or G, Y can be C or T and W can be either A or T (Neuberger M. S and Milstein C. 1995. Somatic hypermutation. Curr. Opin. Immunol. 7, 248-254). In addition, the serine residues encoded by the nucleotides AGY are predominantly present in the CDRs regions of the variable domain over those encoded by TCN corresponding to a potential hot-spot sequences (Wagner S. D., Milstein C. and Neuberger M. S. 1995. Codon bias targets mutation. Nature, 376, 732). The structural analysis has shown that the CDR loops contribute the most to the antigen binding, especially the CDR3 loops (Giudicelli V., Chaume D. and Lefranc M. P. 2004. IMGT/V-QUEST, an integrated software program for immunoglobulin and T cell receptor V-J and V-D-J rearrangement analysis. Nucleis Acids Res. 32, 435-440). Therefore, the nucleotide sequence of the CDRs of the heavy and light chains of each antibody of the invention is scanned for the presence of the hot-spot sequences and AGY codons. The identified hot-spots of the CDR regions of the light and heavy chain are compared to the germinal sequences of the heavy and light chains using the International ImMunoGen Tics database (IMGT, imgt-.cines.fr/textes/vquest/) (Davies D. R., Padlan E. A. and Sheriff S. 1990. Antibody-antigen complexes. Annu. Rev. Biochem. 59, 439-473). A sequence, identical to the germ line, suggest that somatic mutation has not occurred; therefore the random mutations are introduced mimicking the somatic events occurring in vivo. In contrast, a different sequence shows that some somatic mutations have already occurred. It will remain to be determined if the in vivo somatic mutation was optimal. The hot-spots that code for buried or conserved amino acids within the CDRs are not mutagenized. These residues are usually critical for the overall structure and are unlikely to interact with the antigen since they are buried. In addition, the sequences can be compared to the predicted locations in the germ line sequences where somatic mutations occurred predominantly (Tomlinson I. M., Cox J. P. L., Gherardi E., Lesk A. M. and Chotia C. 1995. The structural repertoire of the human Vl domain. EMBO J. 14, 4628-4638, Tomlinson I. M., Walter G., Jones P. T., Dear P. H., Sonnhammer E. L. L. and Winter G. 1996. The imprint of somatic hypermutation on the repertoire of human germline V genes. J. Mol. Biol. 256, 813-817). A similar strategy was applied for the affinity maturation of BL22 scFv. A point mutation introduced in the CDR3 of the heavy resulted in 5 to 10 fold increase in binding activity on various CD22-positive cell lines (Salvatore G., Beers R., Margulies I., Kreitman R. J. and Pastan I. 2002, Improved cytotoxic activity toward cell lines and fresh leukemia cells of a mutant anti-CD22 immunotoxin obtained by antibody phage display. Clinical Cancer research, 8, 995-1002). Also, the mutation of various amino acids in the CDR1 and CDR2 loops also produced mutant with increase affinity ranging from 3 fold to 7 fold (Ho M., Kreitman J., Onda M. and Pastan I. 2005. In vitro antibody evolution targeting germline hot spots to increase activity of an anti-CD22 immunotoxin. J. Biol. Chem., 280, 607-617).

After mutations are introduced, either by random or targeted processes, the antibodies are expressed and assessed for function. For instance, functional screening can be based on binding. Once function is assessed, then DNA sequencing of the chosen antibodies can be carried out using known methods.

In another embodiment, the anchored periplasmic expression (APEx) method described by Harvey, B et al (PNAS 2004 Jun. 22; 101(25): 9193-8) is used for affinity maturation of the binding proteins or immunoconjugates of the invention.

Accordingly, the invention includes binding proteins of the invention that have been affinity maturized to increase the affinity of the binding protein to CD44E and AFP or a variant thereof, or to select a binding protein that has affinity to CD44E or AFP or a variant thereof.

The invention also provides compositions comprising the binding proteins of the invention, preferably antibodies and antibody fragments, with a pharmaceutically acceptable excipient, carrier, buffer or stabilizer.

(C) Immunoconjugates

The invention also includes an immunoconjugate comprising (1) a binding protein of the invention, preferably an antibody or antibody fragment, that has been attached to (2) an effector molecule. In one embodiment, the binding protein of the invention binds to an antigen or molecule on or in a cancer cell.

The antigen can be a protein comprising the 5-v8 interface of CD44E; a protein comprising the v8 exon of CD44; CD44E; a protein comprising amino acid sequence ATNMDSSHSIT; alpha-fetoprotein or a variant thereof; a protein having a molecular weight between 47-53 kDa and an isoelectric point between 5.2-5.5, preferably 5.4; a protein having a molecular weight between 48-54 kDa and an isoelectric point between 5.1-5.4, preferably 5.2; or a protein comprising the amino acid sequence 107 to 487 of AFP (SEQ ID NO:14), 107 to 590 of AFP (SEQ ID NO: 15) or 107 to 609 of AFP (SEQ ID NO:16). In another example the antigen is a protein comprising amino acid SEQ ID NOS: 38, 39, 40, 41, 42, 43, 44 or 45 and having a molecular weight between 47-53 kDa and an isoelectric point between 5.2-5.5; or a protein comprising amino acid SEQ ID NOS: 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 and having a molecular weight between 48-54 kDa and an isoelectric point between 5.1-5.4.

In a preferred, embodiment the effector molecule is (i) a label, which can generate a detectable signal, directly or indirectly, or (ii) a cancer therapeutic agent, which is either cytotoxic, cytostatic or otherwise prevents or reduces the ability of the cancer cells to divide and/or metastasize. Such an immunoconjugate can be generally referred to as "the immunoconjugate of the invention" herein.

In the embodiment of the invention the effector molecule is a cancer therapeutic agent. The cancer therapeutic agent is preferably a toxin that is either cytotoxic, cytostatic or otherwise prevents or reduces the ability of the cancer cells to divide and/or metastasize. Accordingly, one aspect of the invention is an immunoconjugate comprising (1) a binding protein of the invention, preferably an antibody or antibody fragment, attached to (2) a cancer therapeutic agent, such as a toxin.

In another embodiment, the immunoconjugate is internalized and the cancer therapeutic agent is a toxin that blocks the protein synthesis of the cell, therein leading to cell death. Importantly, since most normal cells do not widely express the antigen present on the cancer cells, they cannot bind and internalize the immunoconjugate, and are protected from the killing effect of the toxin or other cancer therapeutic agents.

A variety of effector molecules may be used in the immunoconjugates of the invention and a number of such effector molecules are intracellularly active molecules. Accordingly, in an embodiment of the invention, the immunoconjugate is internalized by the cancer cell.

In preferred embodiments, the effector molecule is a cancer therapeutic agent, more preferably a toxin that comprises a polypeptide having ribosome-inactivating activity including, without limitation, gelonin, bouganin, saporin, ricin, ricin A chain, bryodin, diphtheria toxin, restrictocin, *Pseudomonas* exotoxin A and variants thereof. When the protein is a ribosome-inactivating protein, the immunoconjugate must be internalized upon binding to the cancer cell in order for the toxin to be cytotoxic to the cells. Accordingly, in an embodiment of the invention, the effector molecule is a toxin and the immunoconjugate is internalized by the cancer cell.

In one embodiment of the invention, the toxin is bouganin or *Pseudomonas* exotoxin A, and variants thereof. In another embodiment, the toxin is modified bouganin or a truncated form of *Pseudomonas* exotoxin A that consists of amino acids 252-608.

The invention includes an immunoconjugate comprising a protein encoded by nucleic acid sequence of SEQ ID NO:11 (FIG. 20). The invention also includes an immunoconjugate comprising the amino acid sequences of SEQ ID NO: 12 and 13 (FIG. 21).

In other nonlimiting embodiments, the cancer therapeutic agent comprises an agent that acts to disrupt DNA. Thus, the cancer therapeutic agents may be selected, without limitation, from enediynes (e.g., calicheamicin and esperamicin) and non-enediyne small molecule agents (e.g., bleomycin, methidiumpropyl-EDTA-Fe(II)). Other cancer therapeutic agents useful in accordance with the invention include, without limitation, daunorubicin, doxorubicin, distamycin A, cisplatin, mitomycin C, ecteinascidins, duocarmycin/CC-1065, and bleomycin/pepleomycin.

In other nonlimiting embodiments, the cancer therapeutic agent comprises an agent that acts to disrupt tubulin. Such agents may comprise, without limitation, rhizoxin/maytansine, paclitaxel, vincristine and vinblastine, colchicine, auristatin dolastatin 10 MMAE, and peloruside A.

In other nonlimiting embodiments, the cancer therapeutic portion of an immunoconjugate of the invention may comprise an alkylating agent including, without limitation, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In other nonlimiting embodiments, the cancer therapeutic agent portion of the immunoconjugate of the invention may comprise an antimitotic agent including, without limitation, allocolchicine NSC 406042, Halichondrin B NSC 609395, colchicine NSC 757, colchicine derivative NSC 33410, dolastatin 10 NSC 376128 (NG—auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In other nonlimiting embodiments, the cancer therapeutic agent portion of the immunoconjugate of the invention may comprise an topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In other nonlimiting embodiments, cancer therapeutic agent portion of the immunoconjugate of the invention may comprise an topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In other nonlimiting embodiments, the cancer therapeutic agent portion of the immunoconjugate of the invention may comprise an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5- fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

The present invention further provides immunoconjugates comprising (i) a binding protein of the invention, preferably an antibody or antibody fragment, attached to (2) an effector molecule, wherein the effector molecule is a label, which can generate a detectable signal, indirectly or directly. These immunoconjugates can be used for research or diagnostic applications, such as for the in vivo detection of cancer. The label is preferably capable of producing, either directly or indirectly, a detectable signal. For example, the label may be radio-opaque or a radioisotope, such as $^3H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the immunoconjugate is detectable indirectly. For example, a secondary antibody that is specific for the immunoconjugate and contains a detectable label can be used to detect the immunoconjugate.

The binding protein of the invention, preferably an antibody of antibody fragment, may be "attached to" the effector molecule by any means by which the binding protein can be associated with, or linked to, the effector molecule. For example, the binding protein may be attached to the effector molecule by chemical or recombinant means. Chemical means for preparing fusions or conjugates are known in the art and can be used to prepare the immunoconjugate. The method used to conjugate the binding protein and effector molecule must be capable of joining the binding protein with the effector molecule without interfering with the ability of the binding protein to bind to the antigen on the cancer cell.

In one embodiment, the binding protein, preferably an antibody or antibody fragment, and effector molecule are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the binding protein, preferably an antibody or antibody fragment, and/or effector molecule. In addition, if there are no reactive groups, a photoactivatible crosslinker can be used. In certain instances, it may be desirable to include a spacer between the binding protein, preferably an antibody or antibody fragment, and effector molecule. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

A binding protein-effector molecule protein fusion may also be prepared using recombinant DNA techniques. In such a case a DNA sequence encoding the binding protein is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Examples of attaching an effector molecule, which is a label, to the binding protein include the methods described in Hunter, et al., Nature 144:945 (1962); David, et al., Biochemistry 13:1014 (1974); Pain, et al., J. Immunol. Meth. 40:219 (1981); Nygren, J. Histochem. and Cytochem. 30:407 (1982); Wensel and Meares, Radioimmunoimaging And Radioimmunotherapy, Elsevier, N.Y. (1983); and Colcher et al., "Use Of Monoclonal Antibodies As Radiopharmaceuticals For The Localization Of Human Carcinoma Xenografts In Athymic Mice", Meth. Enzymol., 121:802-16 (1986).

(D) Preparation of Proteins of the Invention

A person skilled in the art will appreciate that the proteins of the invention, such as the light and heavy complementarity determining regions, the light and heavy chain variable regions, antibodies and antibody fragments, and immunoconjugates, may be prepared in any of several ways, but is most preferably prepared using recombinant methods.

Accordingly, the nucleic acid molecules of the present invention may be incorporated in a known manner into an appropriate expression vector which ensures good expression of the proteins of the invention. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1991). In addition, the proteins of the invention may be expressed in prokaryotic cells, such as Escherichia coli (Zhang et al., Science 303(5656): 371-3 (2004)).

Yeast and fungi host cells suitable for carrying out the present invention include, but are not limited to Saccharomyces cerevisiae, the genera Pichia or Kluyveromyces and various species of the genus Aspergillus. Examples of vectors for expression in yeast S. cerevisiae include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153:163 (1983), and Cullen et al. (Bio/Technology 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47-58 (1987), which reviews the use of Agrobacterium rhizogenes vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034)

Insect cells suitable for carrying out the present invention include cells and cell lines from Bombyx, Trichoplusia or Spodoptera species. Baculovirus vectors available for expression of proteins in cultured insect cells (SF 9 cells) include the pAc series (Smith et al., Mol. Cell Biol. 3:2156-2165 (1983)) and the pVL series (Lucklow, V. A., and Summers, M. D., Virology 170:31-39 (1989)). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The proteins of the invention may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

N-terminal or C-terminal fusion proteins comprising the proteins of the invention conjugated with other molecules, such as proteins may be prepared by fusing, through recombinant techniques. The resultant fusion proteins contain a protein of the invention fused to the selected protein or marker protein as described herein. The recombinant protein of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Accordingly, the invention provides a recombinant expression vector comprising the nucleic acid sequences that encode the proteins of the invention, such as the light and heavy chain complementarity determining regions, the light and heavy chain variable regions, the binding proteins, such as antibodies and antibody fragments, and immunoconjugates of the invention. Further, the invention provides a host cell comprising the recombinant expression vector of the invention.

(E) Therapeutic Methods and Pharmaceutical Compositions

The inventors have shown that binding proteins of the invention bind to the extracellular domain of CD44E and that binding proteins of the invention are internalized. Thus, the binding proteins of invention can be used for the targeted delivery of bioactive or medically relevant agents, such as imaging, radioactive or cytotoxic agents.

The inventors have also shown that the binding proteins of the invention bind to AFP or a variant thereof. Full length AFP can be found in free form in circulation and it is internalized upon binding to its receptor. Targeting circulating AFP with the binding proteins of the invention can thus also be used for targeted drug delivery.

In one embodiment, the invention provides a method of treating or preventing cancer, comprising administering to a patient suspected of having cancer an effective amount of the immunoconjugate of the invention, wherein the effector molecule is a cancer therapeutic agent. In another embodiment, the invention provides the use of an effective amount of the immunoconjugate of the invention, wherein the effector molecule is a cancer therapeutic agent, for the manufacture of a medicament for treating or preventing cancer. Furthermore, the invention provides the use of an effective amount of the immunoconjugate of the invention, wherein the effector molecule is a cancer therapeutic agent, comprising the use of an additional cancer therapeutic for the manufacture of a medicament for simultaneous, separate or sequential treatment or prevention of cancer.

In one embodiment of the invention, cancer includes, without limitation, cervical cancer, uterine cancer, ovarian cancer, pancreatic cancer, kidney cancer, gallbladder cancer, liver cancer, head and neck cancer, squamous cell carcinoma, gastrointestinal cancer, breast cancer (such as carcinoma, ductal, lobular, and nipple), prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, colon cancer, rectum cancer, stomach cancer, bladder cancer, pancreatic cancer, endometrial cancer, plasmacytoma, lymphoma, and melanoma. In a preferred embodiment, the cancer includes, without limitation, bladder cancer, breast cancer, cervical cancer, colon cancer, kidney cancer, liver cancer, lung cancer, ovarian cancer, pancreatic cancer, prostate cancer, rectal cancer, skin cancer, stomach cancer, uterine cancer, and head and neck cancer.

The ability of the immunoconjugate of the invention to selectively inhibit or destroy cancerous cells may be readily tested in vitro using cancer cell lines. The selective inhibitory effect of the immunoconjugates of the invention may be determined, for example by demonstrating the selective inhibition of cellular proliferation of the cancer cells.

Toxicity may also be measured based on cell viability, for example, the viability of cancer and normal cell cultures exposed to the immunoconjugate may be compared. Cell viability may be assessed by known techniques, such as trypan blue exclusion assays.

In another example, a number of models may be used to test the effectiveness of the immunoconjugates of the invention. Thompson, E. W. et al. (Breast Cancer Res. Treatment 31:357-370 (1994)) has described a model for the determination of invasiveness of human breast cancer cells in vitro by measuring tumor cell-mediated proteolysis of extracellular matrix and tumor cell invasion of reconstituted basement membrane (collagen, laminin, fibronectin, Matrigel or gelatin). Other applicable cancer cell models include cultured ovarian adenocarcinoma cells (Young, T. N. et al. Gynecol. Oncol. 62:89-99 (1996); Moore, D. H. et al. Gynecol. Oncol. 65:78-82 (1997)), human follicular thyroid cancer cells (Demeure, M. J. et al., World J. Surg. 16:770-776 (1992)), human melanoma (A-2058) and fibrosarcoma (HT-1080) cell lines (Mackay, A. R. et al. Lab. Invest. 70:781 783 (1994)), and lung squamous (HS-24) and adenocarcinoma (SB-3) cell lines (Spiess, E. et al. J. Histochem. Cytochem. 42:917-929 (1994)). An in vivo test system involving the implantation of tumors and measurement of tumor growth and metastasis in athymic nude mice has also been described (Thompson, E. W. et al., Breast Cancer Res. Treatment 31:357-370 (1994); Shi, Y. E. et al., Cancer Res. 53:1409-1415 (1993)).

The immunoconjugates of the invention may be formulated into pharmaceutical compositions for administration to subjects in a biologically compatible form suitable for administration in vivo. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the recombinant protein of the invention to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present invention provides a pharmaceutical composition for treating or preventing cancer comprising the immunoconjugates of the invention, and a pharmaceutically acceptable carrier, diluent or excipient. In a preferred embodiment, the effector molecule of the immunoconjugate in the pharmaceutical composition is a cancer therapeutic agent, more preferably a toxin.

The pharmaceutical preparation comprising the immunoconjugate of the invention may be administered systemically. The pharmaceutical preparation may be administered directly to the cancer site. Depending on the route of administration, the immunoconjugate may be coated in a material to protect the compound from the action of enzymes, acids and other natural conditions that may inactivate the compound.

In accordance with one aspect of the present invention, the immunoconjugate is delivered to the patient by direct administration. The invention contemplates the pharmaceutical composition being administered in at least an amount sufficient to achieve the endpoint, and if necessary, comprises a pharmaceutically acceptable carrier.

The invention also provides methods for reducing the risk of post-surgical complications comprising administering an effective amount of the immunoconjugate of the invention before, during, or after surgery to treat cancer.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, alcohols, polyols, glycerin and vegetable oils, for example. Extemporaneous injection solutions and suspensions may be prepared from sterile powders, granules, tablets, or concentrated solutions or suspensions. Immunoconjugate may be supplied, for example but not by way of limitation, as a lyophilized powder which is reconstituted with sterile water or saline prior to administration to the patient.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In various embodiments of the invention, the pharmaceutical composition is directly administered systemically or directly to the area of the tumor(s).

The pharmaceutical compositions may be used in methods for treating animals, including mammals, preferably humans, with cancer. The dosage and type of immunoconjugate to be administered will depend on a variety of factors which may be readily monitored in human subjects. Such factors include the etiology and severity (grade and stage) of the cancer.

Clinical outcomes of cancer treatments using the immunoconjugates of the invention are readily discernable by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the immunoconjugate and another cancer therapeutic may be determined by comparative studies with patients undergoing monotherapy.

Another embodiment of the invention is a kit for treating or preventing cancer comprising an effective amount of the immunoconjugate of the invention, and directions for the use thereof to treat the cancer.

In the majority of approved anticancer therapies, the anticancer therapy is used in combination with other anticancer therapies. Accordingly, the invention provides a method of preventing or treating cancer using the immunoconjugate of the invention in combination with at least one additional anticancer therapy. The other cancer therapy may be administered prior to, overlapping with, concurrently, and/or after administration of the immunoconjugate. When administered concurrently, the immunoconjugate and the other cancer therapeutic may be administered in a single formulation or in separate formulations, and if separately, then optionally, by different modes of administration. The combination of one or more immunoconjugates and one or more other cancer therapies may synergistically act to combat the tumor or cancer. The other cancer therapies include, without limitation, radiation and other anticancer therapeutic agents. These other cancer therapeutics may include, without limitation, 2,2', 2"trichlorotriethylamine, 6-azauridine, 6-diazo-5-oxo-L-norleucine, 6-mercaptopurine, aceglarone, aclacinomycins actinomycin, altretamine, aminoglutethimide, aminoglutethimide, amsacrine, anastrozole, ancitabine, angiogenin antisense oligonucleotide, anthramycin, azacitidine, azaserine, aziridine, batimastar, bcl-2 antisense oligonucleotide, benzodepa, bicalutamide, bisantrene, bleomycin, buserelin, busulfan, cactinomycin, calusterone, carboplatin, carboquone, caminomycin, carmofur, carmustine, carubicin, carzinophilin, chlorambucil, chlornaphazine, chlormadinone acetate, chlorozotocin, chromomycins, cisplatin, cladribine, cyclophosphamide, cytarabine, dacarbazine, dactinomycin, daunorubicin, defosfamide, demecolcine, denopterin, detorubicin, diaziquone, docetaxel, doxifluridine, doxorubicin, droloxifene, dromostanolone, edatrexate, eflomithine, elliptinium acetate, emitefur, enocitabune, epirubicin, epitiostanol, esorubicin, estramustine, etoglucid, etoposide, fadrozole, fenretinide, floxuridine, fludarabine, fluorouracil, flutamide, folinic acid, formestane, fosfestrol, fotemustine, gallium nitrate, gemcitabine, goserelin, hexestrol, hydroxyurea, idarubicin, ifosfamide, improsulfan, interferon-alpha, interferon-beta, interferon-gamma, interleukin-2, L-asparaginase, lentinan, letrozole, leuprolide, lomustine, lonidamine, mannomustine, marcellomycin, mechlorethamine, mechlorethamine oxide hydrochloride, medroxyprogesterone, megestrol acetate, melengestrol, melphalan, menogaril, mepitiostane, methotrexate, meturedepa, miboplatin, miltefosine, mitobronitol, mitoguazone, mitolactol, mitomycins, mitotane, mitoxantrone, mopidamol, mycophenolic acid, nilutamide, nimustine, nitracine, nogalamycin, novembichin, olivomycins, oxaliplatin, paclitaxel, pentostatin, peplomycin, perfosfamide, phenamet, phenesterine, pipobroman, piposulfan, pirarubicin, piritrexim, plicamycin, podophyllinic acid 2-ethyl-hydrazide, polyestradiol phosphate, porfimer sodium, porfiromycin, prednimustine, procabazine, propagermanium, PSK, pteropterin, puromycin, quelamycin, ranimustine, razoxane, rodorubicin, roquinimex, sizofican, sobuzoxane, spirogermanium, streptonigrin, streptozocin, tamoxifen, taxotere, tegafur, temozolomide, teniposide, tenuzonic acid, testolacone, thiamiprine, thioguanine, thiotepa, Tomudex, topotecan, toremifene, triaziquone, triethylenemelamine, triethylenephosphoramide, triethylenethiophosphoramide, trilostane, trimetrexate, triptorelin, trofosfamide, trontecan, tubercidin, ubenimex, uracil mustard, uredepa, urethan, vinblastine, vincristine, zinostatin, and zorubicin, cytosine arabinoside, gemtuzumab, thioepa, cyclophosphamide, antimetabolites (e.g., methotrexate, 6-mercaptopurine, 6-thioguanine, cytarabine, 5-fluorouracil, fludarabine, gemcitabine, dacarbazine, temozoamide), hexamethylmelamine, LYSODREN, nucleoside analogues, plant alkaloids (e.g., Taxol, paclitaxel, camptothecin, topotecan, irinotecan (CAMPTOSAR, CPT-11), vincristine, vinca alkyloids such as vinblastine.) podophyllotoxin, epipodophyllotoxin, VP-16 (etoposide), cytochalasin B, gramicidin D, ethidium bromide, emetine, anthracyclines (e.g., daunorubicin), doxorubicin liposomal, dihydroxyanthracindione, mithramycin, actinomycin D, aldesleukin, allutamine, biaomycin, capecitabine, carboplain, chlorabusin, cyclarabine, daclinomycin, floxuridhe, lauprolide acetate, levamisole, lomusline, mercaptopurino, mesna, mitolanc, pegaspergase, pentoslatin, picamycin, riuxlmab, campath-1, straplozocin, tretinoin, VEGF antisense oligonucleotide, vindesine, and vinorelbine. Compositions comprising one or more cancer therapeutics (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone. For a full listing of cancer therapeutics known in the art, see, e.g., the latest editions of The Merck Index and the Physician's Desk Reference.

Pharmaceutical compositions for combination therapy may also include, without limitation, antibiotics (e.g., dactinomycin, bleomycin, mithramycin, anthramycin), asparaginase, *Bacillus* and Guerin, diphtheria toxin, procaine, tetracaine, lidocaine, propranolol, anti-mitotic agents, abrin, ricinA, *Pseudomonas exotoxin*, nerve growth factor, platelet derived growth factor, tissue plasminogen activator, antihistaminic agents, anti-nausea agents, etc.

Indeed, administration of an effective amount of an immunoconjugate to a patient in need of such treatment may result in reduced doses of another cancer therapeutic having clinically significant efficacy. Such efficacy of the reduced dose of the other cancer therapeutic may not be observed absent administration with an immunoconjugate. Accordingly, the present invention provides methods for treating a tumor or cancer comprising administering a reduced dose of one or more other cancer therapeutics.

Moreover, combination therapy comprising an immunoconjugate to a patient in need of such treatment may permit relatively short treatment times when compared to the duration or number of cycles of standard treatment regimens. Accordingly, the present invention provides methods for treating a tumor or cancer comprising administering one or more other cancer therapeutics for relatively short duration and/or in fewer treatment cycles.

Thus, in accordance with the present invention, combination therapies comprising an immunoconjugate and another cancer therapeutic may reduce toxicity (i.e., side effects) of the overall cancer treatment. For example, reduced toxicity, when compared to a monotherapy or another combination therapy, may be observed when delivering a reduced dose of immunoconjugate and/or other cancer therapeutic, and/or when reducing the duration of a cycle (i.e., the period of a single administration or the period of a series of such administrations), and/or when reducing the number of cycles.

Accordingly, the invention provides a pharmaceutical composition comprising an immunoconjugate and one or more additional anticancer therapeutic, optionally in a pharmaceutically acceptable carrier.

The present invention also provides a kit comprising an effective amount of an immunoconjugate, optionally, in combination with one or more other cancer therapeutic, together with instructions for the use thereof to treat cancer.

As stated above, combination therapy with an immunoconjugate may sensitize the cancer or tumor to administration of an additional cancer therapeutic. Accordingly, the present invention contemplates combination therapies for preventing, treating, and/or preventing recurrence of cancer comprising administering an effective amount of an immunoconjugate prior to, subsequently, or concurrently with a reduced dose of a cancer therapeutic. For example, initial treatment with an immunoconjugate may increase the sensitivity of a cancer or tumor to subsequent challenge with a dose of cancer therapeutic. This dose is near, or below, the low range of standard dosages when the cancer therapeutic is administered alone, or in the absence of an immunoconjugate. When concurrently administered, the immunoconjugate may be administered separately from the cancer therapeutic, and optionally, via a different mode of administration.

Accordingly, in one embodiment, the additional cancer therapeutic comprises cisplatin, e.g., PLATINOL or PLATINOL-AQ (Bristol Myers), at a dose ranging from approximately 5 to 10, 11 to 20, 21 to 40, or 41 to 75 $mg/m^2$/cycle.

In another embodiment, the additional cancer therapeutic comprises carboplatin, e.g., PARAPLATIN (Bristol Myers), at a dose ranging from approximately 2 to 3, 4 to 8, 9 to 16, 17 to 35, or 36 to 75 $mg/m^2$/cycle.

In another embodiment, the additional cancer therapeutic comprises cyclophosphamide, e.g., CYTOXAN (Bristol Myers Squibb), at a dose ranging from approximately 0.25 to 0.5, 0.6 to 0.9, 1 to 2, 3 to 5, 6 to 10, 11 to 20, or 21 to 40 mg/kg/cycle.

In another embodiment, the additional cancer therapeutic comprises cytarabine, e.g., CYTOSAR-U (Pharmacia & Upjohn), at a dose ranging from approximately 0.5 to 1, 2 to 4, 5 to 10, 11 to 25, 26 to 50, or 51 to 100 $mg/m^2$/cycle. In another embodiment, the additional cancer therapeutic comprises cytarabine liposome, e.g., DEPOCYT (Chiron Corp.), at a dose ranging from approximately 5 to 50 $mg/m^2$/cycle.

In another embodiment, the additional cancer therapeutic comprises dacarbazine, e.g., DTIC or DTICDOME (Bayer Corp.), at a dose ranging from approximately 15 to 250 $mg/m^2$/cycle or ranging from approximately 0.2 to 2 mg/kg/cycle.

In another embodiment, the additional cancer therapeutic comprises topotecan, e.g., HYCAMTIN (SmithKline Beecham), at a dose ranging from approximately 0.1 to 0.2, 0.3 to 0.4, 0.5 to 0.8, or 0.9 to 1.5 $mg/m^2$/Cycle.

In another embodiment, the additional cancer therapeutic comprises irinotecan, e.g., CAMPTOSAR (Pharmacia & Upjohn), at a dose ranging from approximately 5 to 9, 10 to 25, or 26 to 50 $mg/m^2$/cycle.

In another embodiment, the additional cancer therapeutic comprises fludarabine, e.g., FLUDARA (Berlex Laboratories), at a dose ranging from approximately 2.5 to 5, 6 to 10, 11 to 15, or 16 to 25 $mg/m^2$/cycle.

In another embodiment, the additional cancer therapeutic comprises cytosine arabinoside (Ara-C) at a dose ranging from approximately 200 to 2000 $mg/m^2$/cycle, 300 to 1000 $mg/m^2$/cycle, 400 to 800 $mg/m^2$/cycle, or 500 to 700 $mg/m^2$/cycle.

In another embodiment, the additional cancer therapeutic comprises docetaxel, e.g., TAXOTERE (Rhone Poulenc Rorer) at a dose ranging from approximately 6 to 10, 11 to 30, or 31 to 60 $mg/m^2$/cycle.

In another embodiment, the additional cancer therapeutic comprises paclitaxel, e.g., TAXOL (Bristol Myers Squibb), at a dose ranging from approximately 10 to 20, 21 to 40, 41 to 70, or 71 to 135 mg/kg/cycle.

In another embodiment, the additional cancer therapeutic comprises 5-fluorouracil at a dose ranging from approximately 0.5 to 5 mg/kg/cycle, 1 to 4 mg/kg/cycle, or 2-3 mg/kg/cycle.

In another embodiment, the additional cancer therapeutic comprises doxorubicin, e.g., ADRIAMYCIN (Pharmacia & Upjohn), DOXIL (Alza), RUBEX (Bristol Myers Squibb), at a dose ranging from approximately 2 to 4, 5 to 8, 9 to 15, 16 to 30, or 31 to 60 mg/kg/cycle.

In another embodiment, the additional cancer therapeutic comprises etoposide, e.g., VEPESID (Pharmacia & Upjohn), at a dose ranging from approximately 3.5 to 7, 8 to 15, 16 to 25, or 26 to 50 mg/m$^2$/cycle.

In another embodiment, the additional cancer therapeutic comprises vinblastine, e.g., VELBAN (Eli Lilly), at a dose ranging from approximately 0.3 to 0.5, 0.6 to 0.9, 1 to 2, or 3 to 3.6 mg/m$^2$/cycle.

In another embodiment, the additional cancer therapeutic comprises vincristine, e.g., ONCOVIN (Eli Lilly), at a dose ranging from approximately 0.1, 0.2, 0.3, 0.4, 0.5, 0.6 or 0.7 mg/m$^2$/cycle.

In another embodiment, the additional cancer therapeutic comprises methotrexate at a dose ranging from approximately 0.2 to 0.9, 1 to 5, 6 to 10, or 11 to 20 mg/m$^2$/cycle.

In another embodiment, an immunoconjugate is administered in combination with at least one other immunotherapeutic which includes, without limitation, rituxan, rituximab, campath-1, gemtuzumab, and trastuzutmab.

In another embodiment, an immunoconjugate is administered in combination with one or more anti-angiogenic agents which include, without limitation, angiostatin, thalidomide, kringle 5, endostatin, Serpin (Serine Protease Inhibitor), anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13 amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122: 497-511), a 19 amino acid peptide corresponding to a fragment of Thrombospondin I (Tolsma et al., 1993, J. Cell Biol. 122:497-511), a 20-amino acid peptide corresponding to a fragment of SPARC (Sage et al., 1995, J. Cell. Biochem. 57:1329-1334), and a variant thereof, including a pharmaceutically acceptable salt thereof.

In another embodiment, an immunoconjugate is administered in combination with a regimen of radiation therapy. The therapy may also comprise surgery and/or chemotherapy. For example, the immunoconjugate may be administered in combination with radiation therapy and cisplatin (Platinol), fluorouracil (5-FU, Adrucil), carboplatin (Paraplatin), and/or paclitaxel (Taxol). Treatment with the immunoconjugate may allow use of lower doses of radiation and/or less frequent radiation treatments, which may for example, reduce the incidence of severe sore throat that impedes swallowing function potentially resulting in undesired weight loss or dehydration.

In another embodiment, an immunoconjugate is administered in combination with one or more cytokines which include, without limitation, a lymphokine, tumor necrosis factors, tumor necrosis factor-like cytokine, lymphotoxin, interferon, macrophage inflammatory protein, granulocyte monocyte colony stimulating factor, interleukin (including, without limitation, interleukin-1, interleukin-2, interleukin-6, interleukin-12, interleukin-15, interleukin-18), and a variant thereof, including a pharmaceutically acceptable salt thereof.

In yet another embodiment, an immunoconjugate is administered in combination with a cancer vaccine or biological agents including, without limitation, autologous cells or tissues, non-autologous cells or tissues, carcinoembryonic antigen, alpha-fetoprotein, human chorionic gonadotropin, BCG live vaccine, Mycobacterial cell wall-DNA complexes, melanocyte lineage proteins, and mutated, tumor-specific antigens.

In yet another embodiment, an immunoconjugate is administered in association with hormonal therapy. Hormonal therapeutics include, without limitation, a hormonal agonist, hormonal antagonist (e.g., flutamide, tamoxifen, leuprolide acetate (LUPRON)), and steroid (e.g., dexamethasone, retinoid, betamethasone, cortisol, cortisone, prednisone, dehydrotestosterone, glucocorticoid, mineralocorticoid, estrogen, testosterone, progestin).

In yet another embodiment, an immunoconjugate is administered in association with a gene therapy program to treat or prevent cancer.

Combination therapy may thus increase the sensitivity of the cancer or tumor to the administered immunoconjugate and/or additional cancer therapeutic. In this manner, shorter treatment cycles may be possible thereby reducing toxic events. The cycle duration may vary according to the specific cancer therapeutic in use. The invention also contemplates continuous or discontinuous administration, or daily doses divided into several partial administrations. An appropriate cycle duration for a specific cancer therapeutic will be appreciated by the skilled artisan, and the invention contemplates the continued assessment of optimal treatment schedules for each cancer therapeutic. Specific guidelines for the skilled artisan are known in the art. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2; 92(3):205-16.

It is contemplated that the immunoconjugate may be administered by any suitable method such as injection, oral administration, inhalation, transdermal or intratumorally, whereas any other cancer therapeutic may be delivered to the patient by the same or by another mode of administration. Additionally, where multiple cancer therapeutics are intended to be delivered to a patient, the immunoconjugate and one or more of the other cancer therapeutics may be delivered by one method, whereas other cancer therapeutics may be delivered by another mode of administration.

(F) Diagnostic Methods and Agents

The binding proteins of the invention bind selectively to cancer cells or molecules internalized by cancer cells, and not significantly to normal cells. Therefore the binding proteins can be used in the diagnosis of cancer. As stated above, the inventors have shown that the binding proteins of the invention binds to the extracellular domain of CD44E. The inventors have also shown that the binding proteins of the invention bind to AFP or a variant thereof. AFP is associated with abnormal growth, cell transformation and cancer. Thus, the specificity of the binding proteins for tumor antigens makes it useful in the diagnosis of cancer.

In a preferred embodiment, the binding proteins are antibodies or antibody fragments of the invention. In addition, cancer cells may be evaluated to determine their susceptibility to the treatment methods of the invention by, for example, obtaining a sample of the cancer cells and determining the ability of the sample to bind to the binding proteins of the invention, preferably antibodies or antibody fragments.

Accordingly, the present invention includes diagnostic methods, agents, and kits that can be used by themselves or prior to, during or subsequent to the therapeutic method of the invention in order to determine whether or not cancer cells are present that express the antigen and can bind to the binding proteins of the invention, preferably antibodies and antibody fragments.

In one embodiment, the invention provides a method of diagnosing cancer in a mammal comprising the steps of
(1) contacting a test sample taken from said mammal with the binding proteins of the invention that binds to an antigen on or in the cancer cell under conditions that permit the formation of a binding protein-antigen complex;
(2) measuring the amount of binding protein-antigen complex in the test sample; and
(3) comparing the amount of binding protein-antigen complex in the test sample to a control.

In one embodiment, the antigen is CD44E; a protein having a molecular weight between 47-53 kDa and an isoelectric point between 5.2-5.5, preferably 5.4; or a protein comprising the 5-v8 interface of CD44E, v8 exon of CD44 or the amino acid sequence ATNMDSSHSIT. In another embodiment, the antigen is alpha-fetoprotein or a variant thereof; a protein having a molecular weight between 48-54 kDa and an isoelectric point between 5.1-5.4, preferably 5.2; or a protein comprising amino acid SEQ ID NOS: 14, 15 or 16. In another example, the antigen is a protein comprising amino acid SEQ ID NOS: 38, 39, 40, 41, 42, 43, 44 or 45 and has a molecular weight between 47-53 kDa and an isoelectric point between 5.2-5.5; or a protein comprising amino acid SEQ ID NOS: 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 and has a molecular weight between 48-54 kDa and an isoelectric point between 5.1-5.4.

Another embodiment of the invention is a method of diagnosing cancer in a mammal comprising the steps:
(1) contacting a test sample from said mammal with an antibody that binds to alpha-fetoprotein or a variant thereof under conditions that permit the formation of an antibody-alpha-fetoprotein complex and an antibody that binds to CD44E under conditions that permit the formation of an antibody-CD44E complex;
(2) measuring the amount of antibody-alpha-fetoprotein complex and antibody-CD44E complex in the test sample; and
(3) comparing the amount of antibody-alpha-fetoprotein complex and antibody-CD44E complex in the test sample to a control.

The invention further includes a kit for diagnosing cancer comprising any one of the binding proteins of the invention and instructions for the use thereof to diagnose the cancer. The invention also includes a kit for diagnosing cancer comprising an antibody that binds to alpha-fetoprotein and an antibody that binds to CD44E and instructions for the use thereof to diagnose cancer.

For use in the diagnostic applications, the binding proteins of the invention, preferably antibodies or antibody fragments, may be labeled with a detectable marker such as a radio-opaque or radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. As described above, methods of attaching a label to a binding protein, such as an antibody or antibody fragment, are known in the art.

Another aspect of the invention is a method of diagnosing cancer in a mammal comprising the steps of
(1) measuring the amount of antibodies of the invention in a test sample taken from said mammal; and
(2) comparing the amount of antibodies of the invention in the test sample to a control.

In one embodiment, the amount of antibodies of the invention is measured by measuring the amount of antibodies of the invention in the test sample, for example by ELISA. In another embodiment, the amount of antibodies of the invention is measured by measuring the expression levels of nucleic acids encoding the antibodies of the invention in the test sample, for example by RT-PCR.

(G) Antigens

As mentioned above, the inventors have identified the antigen of the binding proteins of the invention. Accordingly, the invention includes an isolated protein that can specifically bind with one of the binding proteins of the invention, and nucleic acid sequences and uses thereof.

In one example, the isolated protein has a molecular weight between 47-53 kDa and an isoelectric point between 5.2-5.5, preferably 5.4; a protein having a molecular weight between 48-54 kDa and an isoelectric point between 5.1-5.4, preferably 5.2; or a protein comprising the amino acid sequence 107 to 487 of AFP (SEQ ID NO:14), 107 to 590 of AFP (SEQ ID NO: 15) or 107 to 609 of AFP (SEQ ID NO:16). In another example, the isolated protein comprises amino acid SEQ ID NOS: 38, 39, 40, 41, 42, 43, 44 or 45 and has a molecular weight between 47-53 kDa and an isoelectric point between 5.2-5.5; or comprises SEQ ID NOS: 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 and has a molecular weight between 48-54 kDa and an isoelectric point between 5.1-5.4, preferably 5.2.

(H) Other Uses of the Binding Proteins of the Invention

Antibodies to CD44 have been shown to block the PMA-induced binding of CD44H (the standard form, also called CD44s) and CD44E to hyaluronic acid (HA) (Liao et al. J Immunol 151(11):6490-99, 1993). Clustering of CD44 variants, particularly those that contain variant exon 9 appears to be important for binding to HA and can be induced by PMA. Down stream intracellular signaling is related to this clustering and interfering with it can affect cell function (Suzuki et al., JBC 277(10):8022-32, 2002). It is possible that the blocking effect of antibodies on HA binding is mediated by interference with clustering. Regardless of the mechanism, the binding proteins of the invention could be used to modulate the binding of CD44 to the extracellular molecules and the downstream cell signaling resulting from clustering, or the binding to HA or/and other extracellular molecules.

Accordingly, the invention includes the use of the binding proteins of the invention to modulate the activity of CD44E. For example, the binding proteins of the invention can be used to interfere with the binding of CD44E to HA. The binding proteins of the invention may also be used to enhance CD44E activity.

The following non-limiting examples are illustrative of the present invention:

EXAMPLES

Example 1

Generation of VB1-008 Monoclonal Antibody

The VB1-008 monoclonal antibody was generated from the peripheral blood lymphocytes of a breast cancer patient. TM-SH-P2 was used as the fusion partner to generate the monoclonal antibody. VB1-008 is an IgG1, lambda monoclonal antibody.

Messenger RNA (mRNA) was isolated from hybridoma cells and first strand complement DNA (cDNA) was synthesized. The cDNA was then used to isolate antibody H and L chain genes by PCR. PCR primers were designed (see note) according to the consensus framework regions of the H (Gamma) and L (Lambda) chain isotypes. The PCR products were individually cloned into the TOPO-pCR 2.1 vector and transformed into E. coli cells. Individual clones containing the inserts in TOPO-PCR 2.1 were isolated and grown. Plasmid DNA was purified and sequenced.

```
Gamma Primers:
                                           (SEQ ID NO: 18)
1)    5' TCT AAA GAA GCC CCT GGG AGC ACA GCT CAT
CAC CAT G 3'

(SEQ ID NO: 19)
2)    5' GCC CGG GGA GCG GGG GCT TGC CGG CCG TCG
CAC TCA 3'

(SEQ ID NO: 20)
3)    5: ACC ATG AGT GAG AAA AAC TGG ATT TGT GTG
GCA 3'

(SEQ ID NO: 21)
4)    5' GGA GCC GGT GAC CAG GGT TCC CTG GCC
CCA 3'

(SEQ ID NO: 22)
5)    5' CTC ACC ATG GAG TTT GGG CTG AGC TGG
GTT 3'

(SEQ ID NO: 23)
6)    5' GGA GGC TGA GGA GAC GGT GAC CAG GGT TCC
CTG GCC 3'

Lambda Primers:
                                           (SEQ ID NO: 24)
7)    5' GGC TCG AGA TGR CCT GSW CYC CTC TCY TYC
TSW YC 3'

(SEQ ID NO: 25)
8)    5' CCC GTC GAC GAA GCT CCT TCA GAG GAG
GG 3' *
```

Note: In order to isolate as many varieties as possible using a single primer, mixed bases are used for certain consensus primers: R=A+G, D=A+T+G, Y=C+T, H=A+C+T, V=A+C+G, K=T+G, S=C+G, W=A+T.

Each PCR reaction comprised the following components in a 50 µL reaction volume.

| | |
|---|---|
| 10× PCR buffer | 5 µL |
| 2 mM dNTPs | 5 µL |
| 50 mM MgCl2 | 2 µL |
| 5' Primer | 20 pmoL |
| 3' Primer | 20 pmoL |
| Taq DNA Polymerase | 2.5 U |
| DNA template | 50 ng |

The PCR cycling conditions were: 94° C. for 1 min., 62° C. for 1 min., 72° C. for 1.5 min. for 30 cycles and a final extension for 10 min. at 72° C. Amplified PCR products were electrophoretically separated on a 1% agarose gel, excised, purified using a Qiaquick gel extraction kit, cloned into the TOPO pCR 2.1 cloning vector and then DNA sequenced using the 373 DNA sequencer stretch (Griffin G. H. and Griffin M. A.: PCR technology, Current innovations. CRC Press, Boca. Raton. Fla. 3431. USA; Cloning vector pCR 2.1, Catalogue #205184. Invitrogen, Carlsbad, Calif.; Qiagen, Qiaquick gel extraction kit, Catalogue #28706. Qiagen Inc., Mississauga, ON; and 373 DNA Stretch. PE Applied Biosystems, Mississauga ON.).

The CDR sequences for VB1-008 are shown in Table 1.

The light chain variable region and the heavy chain variable region are shown in FIGS. 1 and 2, respectively.

Example 2

Antibody Profiling by Measuring Tumor Cell Reactivity

VB1-008 was tested by flow cytometry for tumor cell reactivity against two panels of cell lines. The first panel comprises fifteen different types of epithelial cancers while a second panel consists of five types of normal cells. The VB1-008 results are summarized in Table 2. VB1-008 had an MF>2.0 for all cancer types tested. MF values indicate the mean calculated from the sum of the mean fold increase in median fluorescence over the control antibody from all cell lines in each indication. The strongest indications were, but not limited to, breast, lung, melanoma and prostate. In comparison, VB1-008 was more reactive with most of the tumor cell lines than with the normal cell lines. The two exceptions were the kidney and lung cell lines; however, they were still lower than the corresponding tumor cell type. See Table 2. The fold-increase in VB1-008 reactivity of tumor: normal varied from ~2 to 7.

Example 3

Normal Tissue Microarray

VB1-008 was tested against the flow positive tumor cell line SKBR-3 to assess the appropriate tissue format to demonstrate membrane staining and to define the optimal conditions for staining. This antibody demonstrated cytoplasmic and cell membrane staining in all the experimental groups, including fixed embedded cells. In fixed cell pellets incubated overnight with VB1-008, 80% of the cells showed cytoplasmic staining, and 10% of them showed cell membrane staining. Representative pictures of cell membrane staining of formalin-fixed cell pellet cores are shown in FIG. 3.

Figure 4:
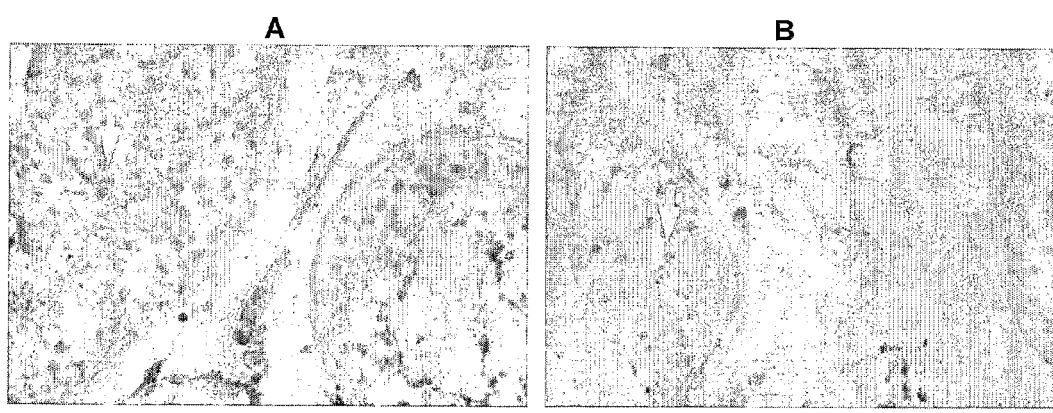
FIG. 4 are representative photographs of immunohistochemical staining of normal testis with VB1-008 and the isotype control antibody 4B5. (A) Sample 925 testes tissue (400× mag) stained with VB1-008. Membrane staining in mature sperm cells is indicated by an arrow. (B) Sample 925 testes tissue (400× mag) stained with IgG isotype control 4B5. Notice absence of staining. Arrow points to mature sperm cell for contrast to staining with VB1-008 in (A).

Once the optimal staining conditions were identified, the antibody was tested in comparison with an isotype control (4B5) on a low density (LD) array of critical normal for normal tissue reactivity. The results for VB1-008 are summarized in Table 3. No significant membrane staining of any of the normal critical tissues was observed. High density (HD) array staining of non-critical normal tissue showed that cell surface staining was limited to epithelial cells associated with reproduction-related tissues (testis and fallopian tubes, FIG. 4, Table 4). Otherwise, no significant staining was observed of any of the tissues was observed.

Example 4

Tumor Tissue Microarray

Figure 5:
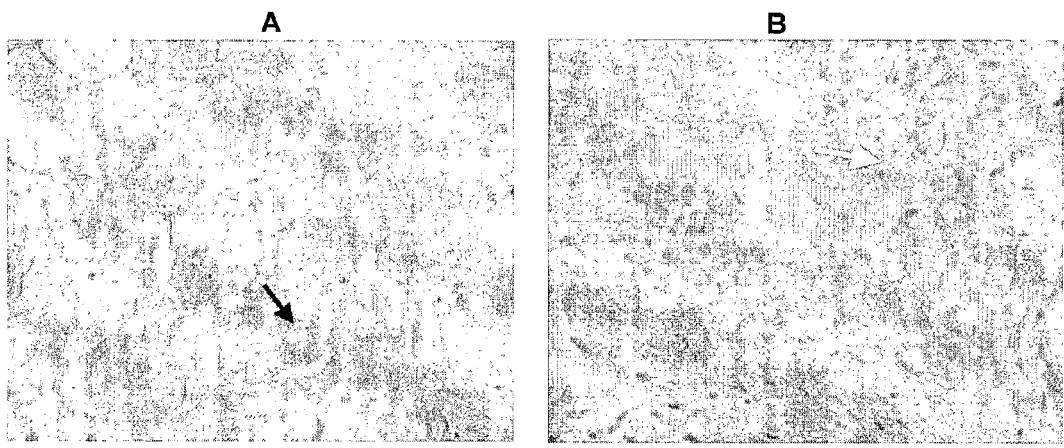
FIG. 5 shows Sample 3427A1 breast adenocarcinoma (400×) stained with VB1-008 and IgG isotype control 4B5. Notice staining of cell membrane of tumor cells, especially of cells in contact with the extracellular matrix (white arrow). Cells close to the center of the tumor show primarily cytoplasmic staining (black arrow). Arrow points to unstained tumor cells. Tumor cells are stained with VB1-008.
Figure 6:
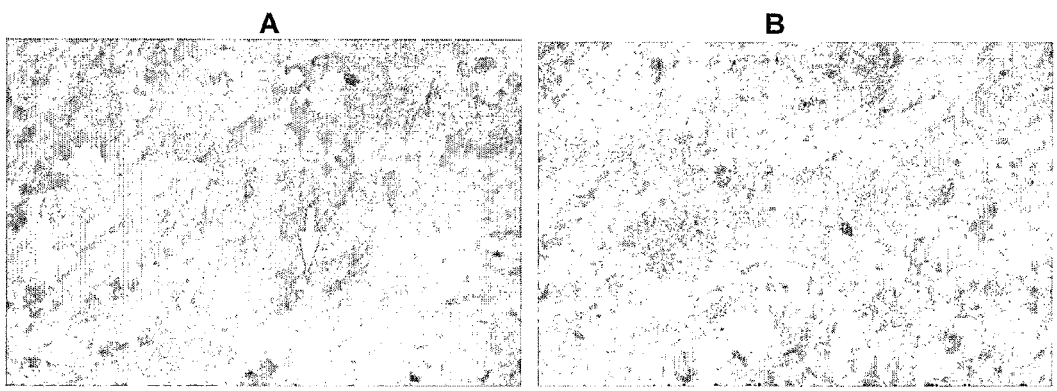
FIG. 6 shows Sample 946 B1 bladder carcinoma (400×) stained with VB1-008 (A) and IgG isotype control 4B5 (B). Arrows indicate membrane staining of the tumor cells with VB1-008 (A) but not with the control antibody (B).
Figure 7:
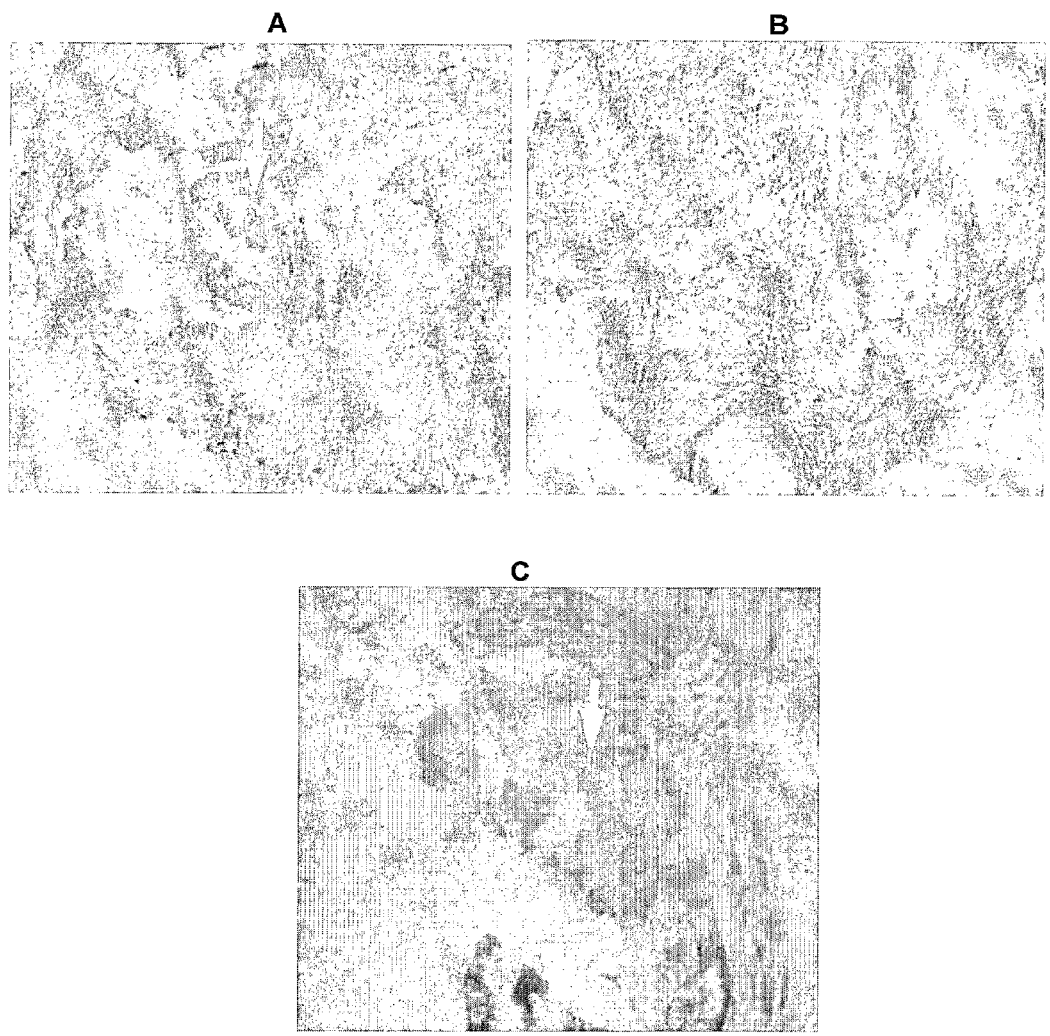
FIG. 7 shows sample 4036A2 uterus carcinoma (200× mag) stained with VB1-008 and the IgG control antibody 4B5. Notice membrane staining (arrow) with VB1-008 (A & C) but not with the control antibody (B). Higher magnification of uterus carcinoma (600×) shows membrane staining (C).

VB1-008 was tested in a HD formalin-fixed tumor TMA for tumor tissue reactivity. See Table 5. VB1-008 exhibited moderate cell surface reactivity against a wide variety of indications including, bladder, breast, colon, kidney, liver, ovary, prostate, rectum, stomach and uterus. VB1-008 cell surface binding was lesser represented and at a lower reactivity with cancers of the cervix, lung, pancreas, and skin. Representative pictures illustrating the cell surface reactivity VB1-008 but not the isotype-matched control antibody to some of the cancers are shown in FIGS. 5-7.

Example 5

Assessment of VB1-008 Binding and Internalization by Flow Cytometry and Confocal Microscopy VB1-008 and two control antibodies (5E9 and MA-103) that demonstrate strong reactivity against the tumor cell line A-375 were used to assess VB1-008 for internalization. A representative experiment is shown in Table 6. VB1-008 binding results at different temperatures were not different from the internalizing antibody 5E9. After 60 min at 37° C., the membrane-bound VB1-008 disappeared from the cell surface, with a 57.5% reduction in median fluorescence. Increasing the incubation time at 37° C. was associated with a further decline in median fluorescence. By 120 min, the median fluorescence had decreased by 62.2%. Flow histograms demonstrating cell-surface binding are illustrated in FIG. 8. To confirm if the cell-surface bound VB1-008 internalized into A-375 cells or instead was shed from the plasma membrane, antibody-treated cells were further evaluated by direct visualization of fluorescence distribution and intracellular staining with the aid of laser scanning confocal microscopy. Like MA-103 and 5E9, incubation of A-375 cells with VB1-008 at 4° C. for 60 min demonstrated a circumferential surface distribution of fluorescence label (FIG. 9A). Warming the VB1-008 antibody bound cells to 37° C. revealed a punctuated pattern of intracellular staining by the internalized antibody within 60 minutes, as shown in FIG. 9B.

Example 6

Binding Affinity

Flow cytometry was used to assess functional affinity [Benedict, C. A., NacKrell, A. J. and Anderson, W. F. (1997) J. Immunol. Methods, 201:223-231]. A range of antibody concentrations were tested against a fixed number of tumor cells (A-375) for 2-hours to construct a saturation curve. Values and graphical analysis were generated using Sigma Plot (Jandel Scientific, San Rafael, Calif.). The inverse of the determined median fluorescence was plotted as a function of the inverse of antibody concentration to determine KD by the Lineweaver-Burk method. A straight line was generated and the KD was calculated from the slope of the curve. The dissociation constant KD values were determined by the following equation: $1/F=1/Fmax+(KD/Fmax)(1/IgG$ or IgM or scFv), where F=background subtracted median fluorescence and Fmax was calculated from the plot. The dissociation constant for VB1-008 was shown to be $5.88 \times 10^{-8}$M.

Example 7

VB1-008 Antigen Identification

Cells

Breast cancer cell lines, MDA-MB 435S, MDA-MB-231; MCF-7; melanoma cell line, A-375; pancreatic tumor cell line, PANC-1 and T-cell lines, Daudi and Ramos were used in the study (Table 7). These cell lines were selected based on the results of tumor cell line profiling by flow cytometry.

Growth and Maintenance of Tumor Cell Lines

The cell lines in the study were purchased from ATCC and cultured in accordance with the guidelines and recommendations of ATCC. Cells were harvested at 90% confluence with viability >90%.

Preliminary Characterization of the Antigen Binding to VB1-008

Preliminary characterization data was obtained from experiments designed to assess the feasibility of the gel-based approach by dot blot assays; and from experiments performed to determine the nature of the epitope associated with the antigens.

The data from these experiments classified the VB1-008 antigen as a "blottable" antigen with a peptide epitope, i.e., the epitope involved in binding to VB1-008 on the antigen was neither glycosylated nor lipid associated. It should be noted that the antigen could be glycosylated at sites other than the binding site.

VB1-008 Ag Enrichment and Purification

Immunoprecipitation

A minimum of 500 µg membrane protein was used for immuno-affinity purification. A pre-clearing step using protein-G sepharose alone was the first step in the purification of the antigen prior to the addition of the antibody. In certain cases, pre-clearing was performed twice to add more stringency to the assay. A total of 15-20 µg of antibody was used as the precipitating agent in the mixture. The antigen-antibody mixtures were nutated overnight at 4° C. using buffer conditions that mimicked physiologic conditions. Care was taken to ensure that protease inhibitors were used in every step of the antigen isolation process.

Immune complexes were centrifuged, washed with RIP-A lysis buffer and eluted with 0.2 M glycine pH 2.5. Supernatants representing the unbound fractions were stored to test the proteins that were not isolated by affinity purification. Immunoprecipitations were carried out on two very positive cell lines, i.e., A-375 and MDA-MB-435S, one moderately positive cell line, MDA-MB-231; one weakly positive cell line, i.e., MCF-7; and three negative cell lines, i.e., Panc-1; Daudi and Ramos, with VB1-008 and equal amounts of 4B5 (isotype-matched control) processed in parallel at all times.

Gel-Based Analysis and Western Blotting

1D-Page

The purified proteins were subjected to reducing and non-reducing conditions of sample preparation and were subsequently analyzed by SDS-PAGE/Western Blotting. When reducing conditions were used, the isolated antigens were treated with sample buffer containing 1% β-mercaptoethanol at 65° C. for 15 minutes and when non-reducing conditions were used, the antigens were mixed with sample buffer devoid of any reducing agent. The resulting blots were probed with the required antibodies and corresponding secondary antibodies conjugated to HRP, to visualize the immuno-purified proteins by chemiluminescence.

2D-Page

The immunoprecipitated proteins were separated by two-dimensional gel electrophoresis to resolve any protein stacking effect that may have occurred in the 1D-PAGE analysis. The 2D-gel electrophoresis resolved proteins according to their isoelectric points (Pi) in the first dimension and on the basis of their molecular weights in the second dimension. The proteins thus resolved were transferred to nitrocellulose membranes, overnight, and processed as in the case of 1D-PAGE. Western blots were probed with VB1-008, anti-CD44 and anti-AFP as required and reacting proteins visualized by chemiluminescence.

Peptide Extraction and Antigen ID

The proteins were excised from 1D-gel and 2D-gels and analyzed. Raw data was obtained predicting the probable proteins based on the number of peptides received. The LC-MS/MS runs were carried out on 'QSTAR- and LCQ-dodeca LC-MS/MS from Thermo Finnigan. De-novo sequencing of the identified proteins was also performed at the same facility.

Example 7(a) 1D-Page/Western Analysis

Figure 10A:
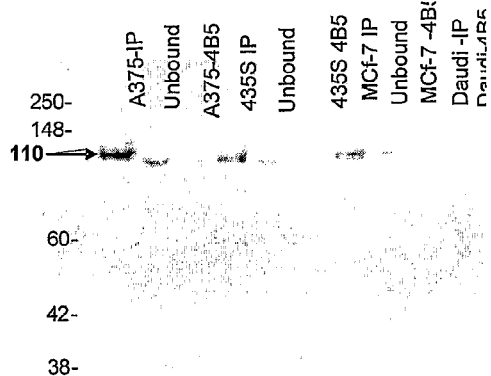
FIGS. 10A, B and C show a western analysis of immunoprecipitation reactions using VB1-008.
Figure 10B:
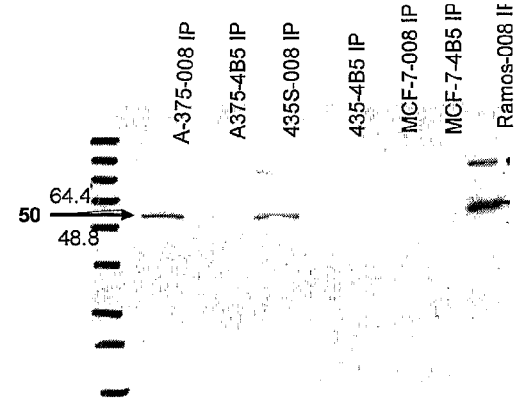
Figure 10C:
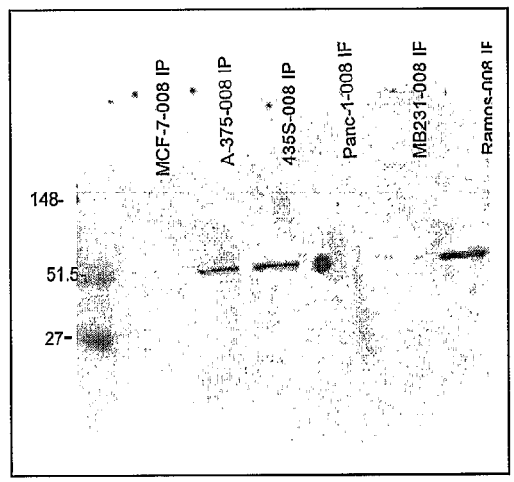

Only one specific band was detected after separation on a 1D-PAGE at ~110 kDa under non-reducing conditions (FIG. 10A) in antigen-positive cell lines (A-375, MDA-MB-435S,). The same band was weakly detected in the weakly positive cell lines (MCF-7) and absent in the antigen-negative cell line (Daudi). When samples were separated on SDS-PAGE under reducing conditions of sample preparation, a predominant band at ~50 kDa and a faint 110 kDa band were observed expressed strongly in antigen-positive cell lines, MDA-MB-435S, A-375, MDA-MB-231, weakly expressed in MCF-7, and absent in antigen-negative cell lines, such as Daudi and Panc-1 (FIG. 10B; FIG. 10C); Ramos was an exception to the above observations (FIGS. 11B and 10C). None of the cell lines showed positive immunoprecipitation with 4B5. The Western data is summarized in Table 8.

To determine the specificity of binding of the antigens detected by IP and Western blotting, four cell lines were pre-cleared twice and the resulting solutions immunoprecipitated with VB1-008. As can be seen in FIG. 10B, no band was detected in MCF-7, but the rest of the cell lines, showed the same 2 specific bands at ~50 kDa and ~110 kDa (faint). Apart from these, as seen in FIG. 10A as well, immunoprecipitation with 4B5 did not yield any detectable reactive proteins with VB1-008, indicating specificity in the purification technique employed. The binding profiles of VB1-008 to these seven cell lines, measured by flow cytometry, were comparable to the results observed in the immunopurification experiments (Table 8).

Example 7(b) 2D-Page Analysis

In order to determine isoelectric points (Pi) and assess the possibility of protein stacking in the 1D-PAGE analysis, the purified antigens for VB1-008 were separated on two-dimensional polyacrylamide gel electrophoresis (2D-PAGE), where the separation in the first dimension was on the basis of Pi and the second dimension on the basis of molecular weight. The gels were then transferred to nitrocellulose membranes and subjected to standard Western blotting processing. Since the amounts required for the detection of proteins on a 2D gel is ~4 times higher than the requirement for a 1D gel, purified antigens from 4 separate immunoprecipitation reactions were pooled together for one 2D-PAGE analysis. Two separate gels were processed simultaneously for Western blot analysis to ensure that the proteins detected on the Coomassie stained gels were the same as those observed in the Western blots. The 2D Western blots were probed with VB1-008 and detected by ECL (chemiluniscence). As can be seen in FIG. 11A, two spots were detected at ~49 kDa/Pi=5.2-5.6.

FIG. 11B represents the coomassie stained profile of the immunoprecipitates from MDA-MB-435S separated by two-dimensional gel electrophoresis. The two spots that were observed, labeled as spots "C" and "D" were excised for MS analysis. The details of the proteins identified are given in the Tables 9A and 9B, respectively.

Peptide Extraction and Protein Analysis

A-375 and MDA-MB-435S membranes were used to immunopurify antigen(s) that bind specifically to VB1-008. Under reducing conditions of gel separation, ~50 kDa band was observed in both the cell lines and under non-reducing conditions, ~110 kDa band was observed, referred to as "E" from MDA-MB-435S cells. These protein bands were excised from the coomassie stained gels for MS analysis.

Proteins from 1D-gel band and 2D-spots were digested with trypsin to release them from the gel and analyzed on a reverse-phase LC-MS/MS system. The identities of the proteins were revealed by database analysis using bioinformatic tools. Raw data included peptides obtained, and a list of suggested proteins including contaminants such as keratin. To obtain the analysis MS/MS spectra were submitted directly to Mascot search engines available at www.Matrix-science.com.

Analysis of Peptide Masses and their Identities

The connection between the isoelectric point (Pi) and the molecular weight of the putative protein candidate is a critical parameter for protein ID. Care was taken during analysis to ensure that the identified peptide masses and their Pi were within ±3 kDa range and ±0.2 Pi respectively. This is because of the inherent possibility of peptides to exist in different modified states, resulting in their deviation from the theoretically calculated masses and Pi. Any acceptable deviation should not be more than the values specified earlier. In cases, where the number of peptides was very low, an additional MS step was required to obtain more information by a process known as "de-novo sequencing". De-novo sequencing is a process where a second MS step fragments each of the peptides obtained in the first MS run into peptide fragment ions (y and b ions), each representing an ionized form of an amino acid. The sequence of each peptide can then be deduced from the resulting mass spectrum.

Peptides have a general tendency to undergo modifications such as oxidation of methionines; esterification of acidic "R" groups, acetamide formations of amine groups and hydroxylations of proline, hydroxyproline and glycine residues during MS/MS fragmentations. When these modifications occur, the peptide masses, although identical are perceived as different peptides, resulting in a false increase in scoring pattern of the protein ID, which is otherwise a cumulative unit of all the individual peptides identified. If the peptides are not analyzed properly, spurious scores may arise leading to incorrect protein identification. Therefore, it was critical to assess and select "unique" peptides that were not repetitive or represented elsewhere and award scores correctly on the basis of these unique peptides. In addition, several other parameters such as the SE window, the number of missed cleavages, metastable fragmentation, single amino acid modifications, etc., were taken into account before the final analysis was performed in-house. As a consequence of these stringent steps, a large number of peptides were drastically reduced to a fewer number. The database searches using these edited lists pulled down mapped proteins. Since the procedure employed here is immunopurification, the presence of remnant antibody also was considered as a contaminant along with well-known contaminants such as actin, vimentin, keratin, cytokeratin and tubulin. The resulting 3-4 final proteins were legitimate IDs, selected or eliminated based on the Pi and molecular weights of the proteins deduced by 2D-PAGE.

Analysis of 2D Spot "C"

Spot "C" excised from the 2D-gel identified only alpha-fetoprotein (AFP), while the other two proteins listed were protease inhibitors added for the integrity of the protein during the study. The Pi also matches the possibility of the molecule being AFP. The MS analysis revealed 65 peptides, but only 30 unique peptides were retrieved which constituted 54% sequence coverage for human AFP with each peptide showing 100% homology to the original protein. However, the AFP molecule lacked the first 160 aa from the N-terminus. Sequence analysis of the human AFP molecule showed clear presence of lysine and arginine residues in these first 106 aa, which could be cleaved as peptides, should they be present in the molecule. De-novo sequencing information of the 2D spot "C", showed a lack of 160 aa from the N-terminus, which has been a recurrent phenomenon when the identity of AFP was established (FIG. 12A). The combined results of De-novo sequencing from the 1D gel and the 2D gel is shown in FIG. 12B. The results show a lack of 106 aa from the N-terminus. Table 11A lists the peptides identified.

Analysis of 2D-Spot "D"

Spot "D" from the 2D-gel revealed the identities of 3 proteins in addition to co-purifying contaminants, actin and actin-binding protein actinin. However, except for CD44, the Pi of the other two proteins were distinctly different from the one observed for the 2D spot, therefore they were excluded as protein IDs. The molecular weight of the CD44 isoform 3 was determined to be 53.585±3 kDa making it a complete match for the molecular weight and Pi observed on 2D-PAGE analysis for the spot "D".

Analysis of the 110 kDa Antigen Band

As mentioned earlier, under reducing conditions the ~110 kDa band was visualized by both Coomassie and Western blot analysis. From the 2D-PAGE analysis, it was clear that there were two components each around ~50 kDa, individually identified as CD44 and AFP, contributing together to form a 110 kDa band when the conformation was preserved under non-reducing conditions of gel separation. Thus for confirmation, the 110 kDa band was excised and analyzed to identify the protein components. The ~110 kDa band seen in FIG. 13A, was excised (E) for MS analysis. The details of the proteins identified from the 100 kDa band are given in Table 10.

MS Analysis of Protein Band "E"

Figure 15A:
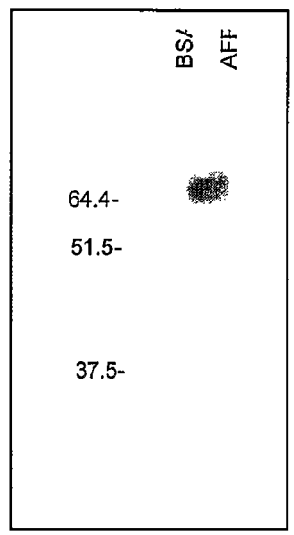
FIG. 15A shows the reactivity of VB1-008 to recombinant AFP molecule, commercially available from RDI systems. The recombinant AFP was electrophoresed, transferred on to nitrocellulose membrane and probed with VB1-008. The results are clearly indicative of the reactivity of VB1-008 to AFP.

The results of the MS analysis for protein band "E" are given in Table 10. Apart from the co-purifying contaminants, i.e., actin, actinin and vimentin, three protein identities were obtained. Among them were CD44, AFP and heat shock protein 90. Heat shock protein 90 was not a match for the molecular weight identified, and was therefore excluded as a potential candidate. Since CD44 is membrane-associated, it is likely the cognate antigen. It has also been demonstrated that AFP co-purifies with CD44 (FIG. 15A), however, AFP was not detected on the membrane surface.

Using top-down proteomics approach, it was clear that the molecular weight of the isolated antigen (50 kDa) corresponded to the predicted molecular weight of CD44E. Flow experiments and the binding rank order to the given cell lines also validate this finding. Data in Tables 11B and 12 describe the details associated with the mapping of the peptides identified by MS/MS analysis. Specifically, a set of 8 peptides were isolated that mapped to 3 different regions on the CD44 molecule. Particularly, one peptide mapped to v8-v9 region which is unique to CD44E in addition to being present in the parent molecule.

FIG. 14 represents the sequence coverage obtained from mapping the peptides obtained in the protein database. A set of 8 peptides were obtained in all mapping the extracellular region, one in the variable region and 4 in the cytoplasmic region of the CD44 molecule. The homology searches and mapping of peptides to CD44 variants indicate that CD44R1 and CD44 R2 also express v8-v10 exons in the variable region. However, they lack a major portion of the cytoplasmic tail from the exon 19. Therefore show homology only to 4 peptides out of 8 identified from our analysis, hence do not fit into the criterion of Molecular weight/Pi observed from the antigen purified by immunoprecipitation. The predicted molecular weight of 53.8 kDa for CD44E and the observed molecular weight and Pi proved to be an exact match. Therefore, the CD44 isoform that is the possible antigen for VB1-008 is CD44E or the epithelial form, also referred to as Isoform-3.

Example 7(c) Validation of VB1-008 Antigen (1) Cell Surface Reactivity of Anti-CD44 and Anti-AFP by Flow Cytometry The possibility of CD44 being the cognate antigen for VB1-008 has been clearly established through immunopurification, gel-based analysis and MS analysis. Membrane preparations have been used in all the studies performed with VB1-008 based on the preliminary characterization experiments that clearly suggested the membrane localization of the antigen binding to VB1-008. To determine the orientation of the two components of the antigen on the cell surface, reactivity was measured by flow cytometry on a panel of cell lines, with VB1-008, anti-CD44, anti-AFP and anti-EGFR. Appropriate isotype-matched controls were also used in the study.

A panel of cell lines expressing different levels of VB1-008 Ag was selected for comparative cell surface reactivity experiments. Approximately, 300,000 cells from each cell line were used and the fold-increase in median fluorescence of VB1-008/anti-CD44/anti-AFP was measured and compared to the respective isotype-matched controls. The antigen intensity column was a compilation of the signal intensity observed on WB analysis for each cell line, probed with the corresponding antibodies. The isotype-matched control for VB1-008 was 4B5-IgG and the control for anti-CD44, anti-AFP and anti-EGFR were mouse IgG, since the latter three antibodies were mouse monoclonal antibodies.

As seen in Table 13, the rank order of the binding of anti-CD44 was similar to VB1-008. Anti-AFP did not show any detectable binding over the isotype-matched control. Since anti-CD44 and anti-AFP were mouse monoclonal antibodies, anti-EGFR, a mouse monoclonal antibody was used as a positive control. Not only was the rank order of binding comparable, anti-CD44 showed an enormous increase of over 48-fold compared to the binding of VB1-008, suggesting the presence of a cognate antigen-antibody interaction. The antigen intensity as observed from Western blotting profiles also was comparable to the profile obtained by flow.

(2) 1D-Page/Western Blotting Analysis of Recombinant AFP

AFP is a serum glycoprotein that is available commercially as a 67 kDa recombinant molecule. This molecule was purchased from RDI laboratories and 0.3 μg of the pure protein, AFP and 0.3 μg of BSA were electrophoresed on SDS-PAGE, transferred to nitrocellulose membrane and probed with VB1-008. As can be seen from FIG. 15A, positive reactivity was observed indicating the presence of an epitope on AFP that is recognized by VB1-008. Since AFP was one of the two identified protein molecules purified by immunoprecipitation with VB1-008 and identified by MS analysis, the current western blotting experiment proves the presence of AFP in the immunopurified sample by VB1-008.

(3) Western Blot Analysis of VB1-008 Ag and Reactivity with Anti-AFP and Anti-CD44

Figure 15B:
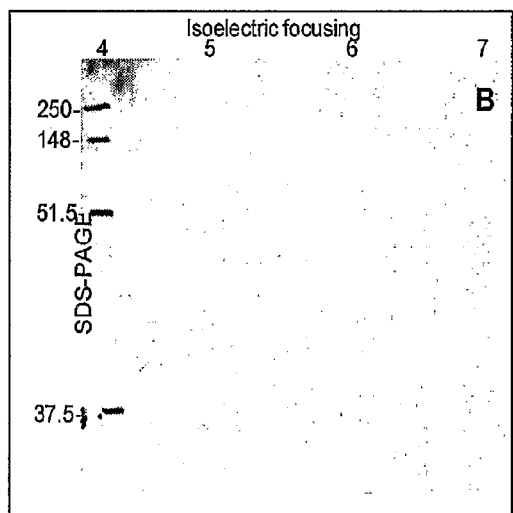
FIGS. 15B and C are 2D-gel profiles of "B" and "C", which were immunoprecipitates obtained using VB1-008. The gels were transferred to nitrocellulose and probed with anti-CD44 and anti-AFP, both mouse-monoclonal antibodies respectively.
Figure 15C:
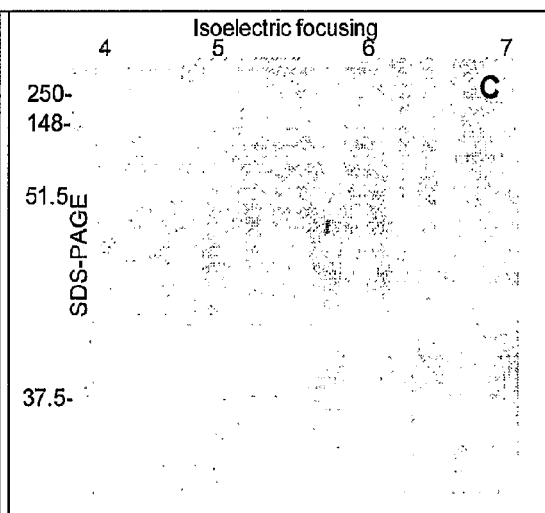

2D-PAGE separation of the eluates from the VB1-008 immunoprecipitation reaction of MDA-MB-435S membranes revealed the presence of two distinct spots, "C" and "D", in the Pi range of 5.1-5.4 and molecular weight 51±3 kDa, and Pi range 5.2-5.5 and 50±3 kDa respectively. The two spots were visualized when probed with VB1-008 as well. LC-MS/MS analysis of these two spots revealed the identities of AFP and CD44, whose presence was confirmed even in the 110 kDa band seen under non-reducing conditions. Therefore, as a next step, the same conditions of immunopurification were repeated, resolved on 2D-PAGE, transferred to nitrocellulose membranes and the Western blots were probed with anti-AFP and anti-CD44. The results are shown in FIG. 15B and FIG. 15C.

Each of the commercially available antibodies, anti-AFP and anti-CD44 reacted specifically with the cognate spots identified by MS analysis from FIGS. 11A and 11B as spots "C" and "D" respectively. In FIGS. 15B and C, two spots around the same Pi, differing by 2-3 kDa were seen interacting to anti-CD44, possibly due to some random loss of a few amino acids as a processing by-product or due to the sensitivity of anti-CD44 to recognize the presence of surrounding CD44 epitopes. The point that needs to be emphasized is that the two spots that reacted with VB1-008, identified to be AFP and CD44 have been visualized with the respective antibodies at the appropriate positions of mass and Pi.

(4) Cross-Reactivity of AFP to CD44

In order to understand the relationship of AFP to CD44, an experiment was designed to immunoprecipitate all CD44 isoforms, using anti-CD44. These proteins selectively purified were subjected to SDS-PAGE and WB. Three sets of identical experiments were carried out simultaneously. Western blots were probed with anti-CD44.

Figure 16:
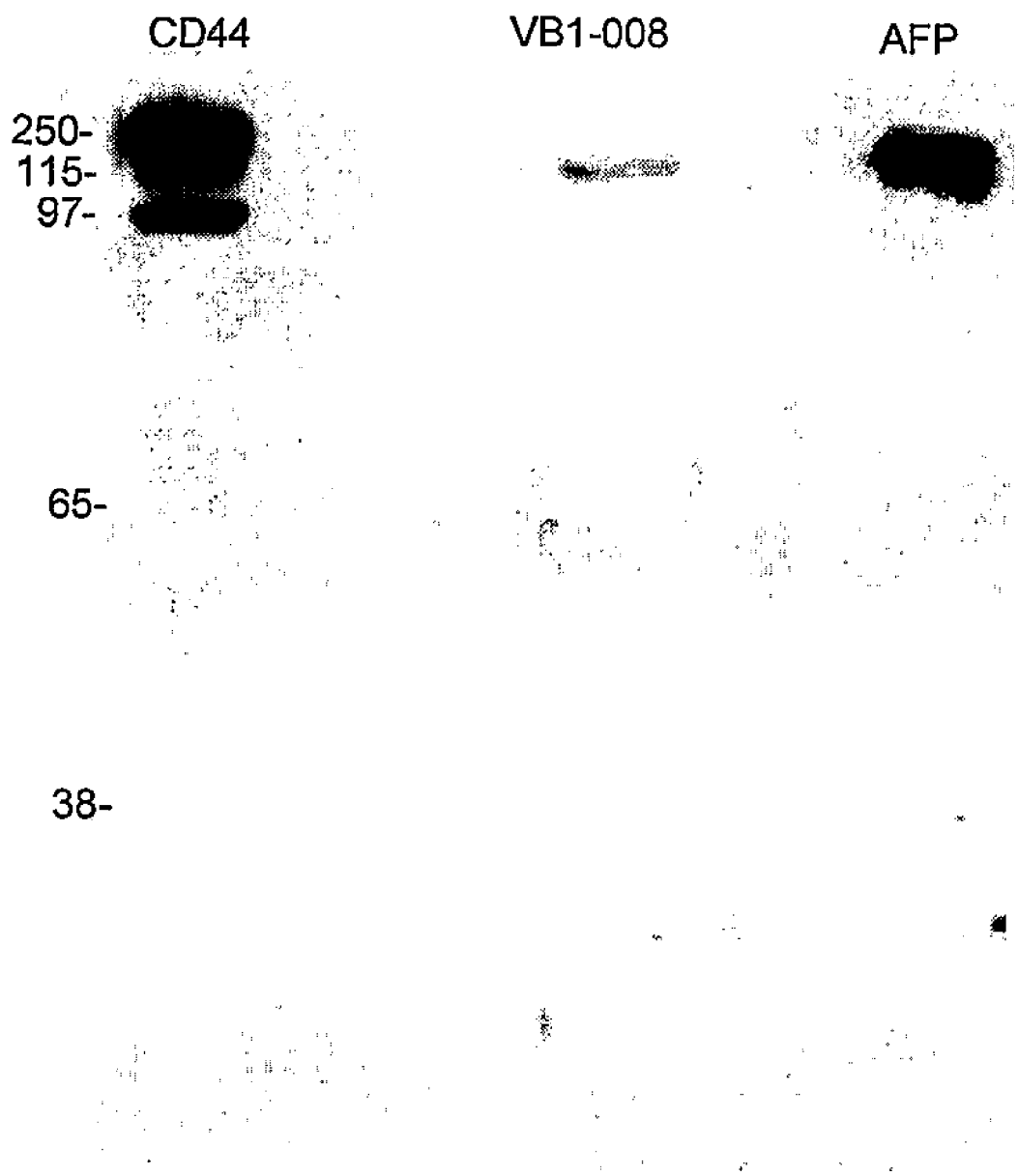
FIG. 16 is a western analysis under non-reducing conditions. Anti-CD44 was used to immunopurify CD44 proteins from MDA-MB-435S cells and the purified fraction was subjected to SDS-PAGE and WB analysis under non-reducing conditions. The experiment was performed in three sets and each set was identical to the other. Each of the sets was probed with 5 μg/mL of anti-CD44, anti-AFP and VB1-008. Anti-CD44 and anti-AFP were mouse monoclonal antibodies, whereas, VB1-008 is VBI's human monoclonal antibody.

As can be seen in FIG. 16, AFP very strongly reacts with CD44 between 115-200 kDa range when experimented under non-reducing conditions. VB1-008 reacts with CD44 as expected and is seen as a clean single band at ~110 kDa range as has been seen in previous cases. Therefore it is possible that AFP is yet another co-purifying protein that possesses an inherent capacity to interact with CD44. As a result of being bound to CD44, it gets pulled down when immunopurified with VB1-008.

Discussion

Immunopurification experiments with VB1-008 showed a single specific band at ~110 kDa under non-reducing conditions and a single 50+3 kDa band under reducing conditions of 1D-PAGE. In order to resolve protein stacking possibilities and to determine the isoelectric point of the protein, 2D-PAGE analysis was performed. Results from 2D-PAGE analysis showed the presence of two spots at Pi=5.1-5.4 and 5.2-5.5 with molecular weights of 51±3 kDa and 50±3 kDa, respectively. MS/MS analysis of the 2D spots recovered 32 and 8 peptides, spanning 54% and 28% of each protein identified, respectively. The two putative antigens identified were CD44 isoform 3 and low molecular weight form of alpha-fetoprotein.

Validation experiments were performed to confirm the presence of the suggested antigens. SDS-PAGE/Western blot analysis of recombinant AFP molecule probed with VB1-008 showed positive reactivity in the 67 kDa range as one strong single band, thus confirming the presence of AFP. To confirm the presence of CD44, the same panel of cells was tested using anti-CD44 by flow cytometry. CD44 showed a dramatic increase in binding compared to VB1-008, also preserving the same rank order. AFP failed to bind to any of the cell lines tested. These results suggest that CD44 is the cell surface antigen that is recognized by VB1-008. Also, immunopurification and subsequent MS/MS analysis clearly implicate the involvement of AFP.

CD44E as the VB1-008 Ag

Protein identification was done with m/z measurements of tryptic peptides from VB1-008 Ag purified by immunoprecipitation. Thorough searches of the protein databases led to one perfect hit corresponding to a set of 8 peptides identified from the immunopurified VB1-008 Ag, pointing to CD44 isoform 3 also known as CD44E or the epithelial form. The molecular weight of the purified antigen, rules out the possibility of both isoforms (1 and 2) as the antigen recognized by VB1-008 on the cells lines. Other isoforms such as isoform 2 which encodes all the exons except v1 or CD44v3, 8-10 could also be expected to react with VB1-008 but their molecular weight and/or pI are not consistent with those observed for the VB1-008 cell surface antigen.

We show evidence for the occurrence of the predicted molecular weight of the CD44E or isoform 3 as 50±3 kDa on both 2D-PAGE, probed with anti-CD44 and on 1D-PAGE under reducing conditions of sample preparation, which under non-reducing conditions was observed as 110±10 kDa on 1D-PAGE and Western blot analysis. LC-MS/MS analysis of the proteins confirms the presence of CD44E.

Example 8

Epitope Mapping-Binding Experiments

As described above, immunoprecipitation and MS analysis have identified CD44E (isoform 3) as the VB1-008 antigen. CD44E differs from other splice variants in having exons v8-v10 in between the conserved sequences, exons 1-5 and 16-20. Peptides were then synthesized from the unique region of CD44E (i.e., the amino acid sequence that spans the exon 5-v8 junction) in order to identify the reactive epitope of VB1-008. A peptide of the same length taken from the C-terminal region of CD44E was used the negative control.

Methods and Reagents

Peptides from the Unique Region of CD44E

Synthetic peptides spanning the exon 5-V8 junction of CD44E were ordered from Global peptide services, LLC. The amino acid sequence (17 aa) from CD44E spans a length of 6 amino acids from exon 5 and 11 amino acids from the unique peptide of the v8 region. The highlighted portion of FIG. 18A represents the stretch of 17 amino acids which has been split into 3 peptides, and the negative control peptide sequence is as highlighted in the C-terminal region of the protein.

The amino acid sequence of each peptide is as follows:

```
Peptide 1:
                                    (SEQ ID NO: 26)
Biotin-STDRIPATNMD-1445.2 amu Peptide 2:
                                    (SEQ ID NO: 27)
Biotin-RIPATNMDSSH-1453.27 amu Peptide 3:
                                    (SEQ ID NO: 28)
Biotin-ATNMDSSHSIT-1387.58 amu Negative:
                                    (SEQ ID NO: 29)
Biotin-AVEDRKPSGLN-1410.19 amu
```

Solubilizing Peptides

All peptides were solubilized in PBS. The pH of the solution was adjusted with 0.01N HCl or 0.01N NaOH if any difficulty in solubility was observed. The peptide was stored in stock solutions (1000 nM) at −20° C.

Coating the Peptides on an ELISA Plate

Peptide solutions were diluted 1-in-100 with Hank's buffered saline solution (HBSS) containing 0.5% formaldehyde. 100 µL of diluted peptide solution was distributed to each well in a 96-well plate. The plates were incubated at room temperature for 1 hour. The supernatant was removed and the plates were placed uncovered in a 37° C. incubator for 16-18 hours. The peptide-coated plates were placed in plastic bags and stored at 2-8° C. until required.

Alternatively, the peptides were diluted in carbonate/bicarbonate buffer pH 9.6 and coated on the plates. All the other steps with the exception of a change in the coating buffer were the same.

Binding of VB1-008 to the Peptide-Coated ELISA Plates

VB1-008 binding to immobilized peptides was performed according to SOP 2.1.19 and SOP 2.2.7:

Following overnight incubation of the peptide-coated plates, 300 µL of wash buffer (PBS containing 0.5% Tween20) was manually added to each plate, with the help of a repeator pipette equipped with an 8-channel adaptor. The contents of the plates were discarded; the plates were inverted and patted on 3-4 inches of paper towel to remove excess liquid. The above steps were repeated two more times.

Blocking

The peptide-coated plates were blocked with 300 µL/well with blocking buffer (PBS containing 1% BSA). The plates were incubated for 30-60 minutes at room temperature. The block buffer was discarded after the incubation.

Binding

Aliquots equivalent to 75 µg/mL of VB1-008 were added to each of the wells and incubated at 37° C. for two hours. The plates were washed as previously described with the wash buffer (PBS containing 0.5% Tween 20). The plates were incubated with 1:6000 dilution of anti-human IgG-HRP for one hour at room temperature. The plates were washed as previously described. 100 µL of TMB substrate (TMB peroxidase substrate KPL cat#50-76-00) was added to each well and incubated for 5-10 minutes in the dark. The reaction was terminated by adding 100 µL of 1M phosphoric acid to each well. The optical density was measured at 450 nm using an ELISA plate reader.

Alternatively, ELISA plates were coated with 100 µg/mL of VB1-008, according to the SOP 2.1.111, and binding of the biotinylated peptides to VB1-008 were assayed according to SOP 2.1.41 for the detection of biotinylated probes.

Results

Screening of synthetic peptides from the unique region of CD44E (i.e., the amino acid sequence that spans the exon 5-v8 junction), revealed that Peptide 3 showed the strongest binding, followed by peptide 2 which demonstrated 50-60% of the binding observed with Peptide 3. A peptide of the same length taken from the C-terminal region of CD44E used as negative control did not show any reactivity as was the case with Peptide 1. Reactivity of VB1-008 with peptide 3 demonstrated that this region of CD44E contains the reactive epitope of VB1-008. See FIG. 18B.

Example 9

Epitope Mapping-Competition Experiments

The competing efficiency of the peptides for VB1-008 binding was then assayed.

Methods and Reagents

Growth and Maintenance of Tumor Cell Lines

Cell lines that are VB1-008-positive, i.e., MDA-MB-435S were cultured and maintained according to ATCC guidelines.

Synthetic Peptides

All peptides were solubilized in PBS and stored at 1.428 mM (2 mg/mL) and as 100 µM solutions at −20° C.

Competition Assay

VB1-008 (75 µg/mL)—0.5 µM concentration, was used as the non-competed control. Molar excesses, i.e., 20×, 40×, 100× and 200× of peptides were used to compete with VB1-008. The peptides/VB1-008 mixtures were incubated on ice for 10 minutes prior to binding by flow. 4B5-IgG was used as the Isotype-matched control and anti-EGFR was used as the unrelated antibody. These two antibodies were processed exactly the same as VB1-008.

Binding of VB1-008

The binding of VB1-008, along with the anti-EGFR and 4B5-IgG antibodies to MDA-MB435S cells was assessed by flow cytometry; and was performed according to the optimized protocol previously described. Cells treated with peptides and those that were untreated were processed similarly.

Results

Figure 19A:
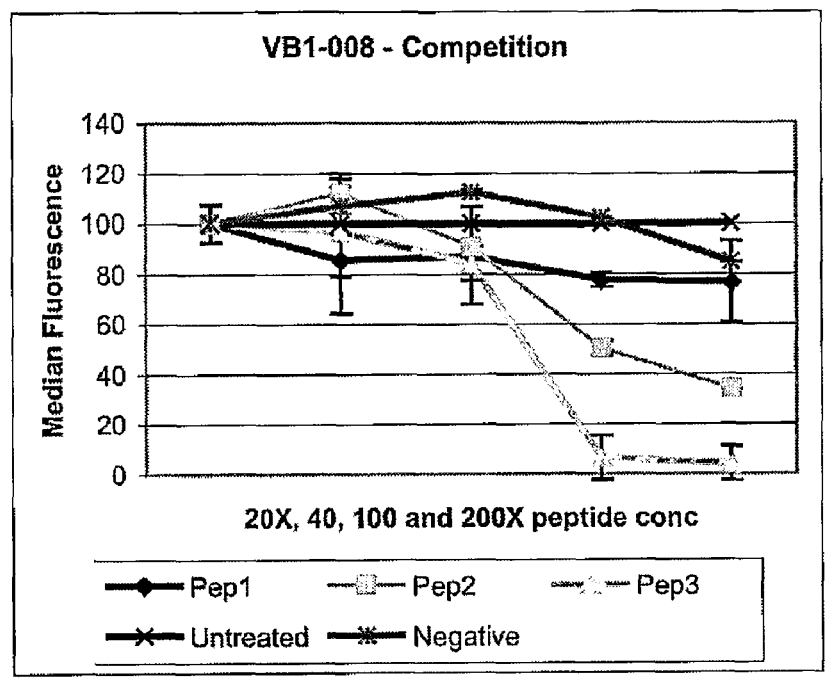
FIG. 19A shows the results of a competition study using peptides 1-3 against binding of VB1-008.

As seen in FIG. 19A, peptide 1 did not compete with VB1-008 binding to MDA-MB435S, peptide 2 competed at 60% efficiency with VB1-008 binding to MDA-MB435S and peptide 3 competed at 96% efficiency with VB1-008 binding to MDA-MB435S. The control showed no competition to VB1-008.

Figure 19B:
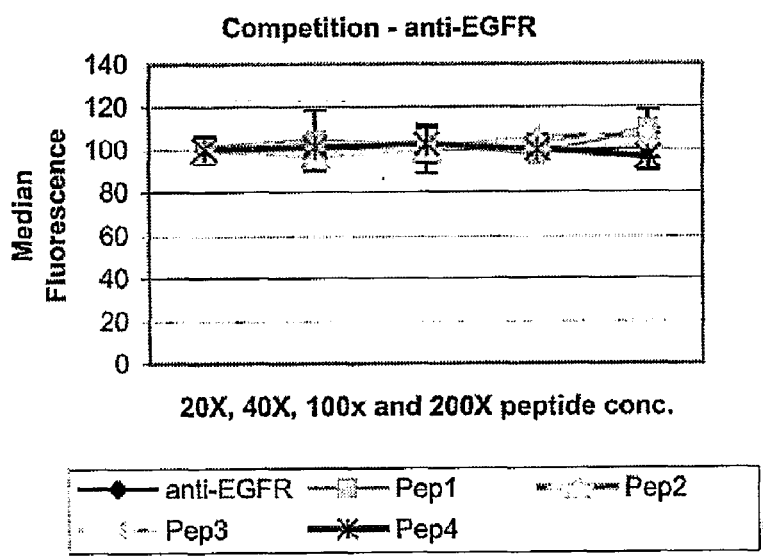
FIG. 19B shows the results of a competition study using peptides 1-3 against a control antibody (anti-EGFR).

FIG. 19B shows the results of the isotype-matched control. None of the peptides or controls compete with anti-EGFR for binding.

Example 10

Cytotoxicity of VB1-008 Immunotoxin

Methods and Reagents

The VB6-008 construct, comprising VB1-008 attached to a modified bouganin was constructed using the methods disclosed in PCT/CA2005/000410 and U.S. patent application Ser. No. 11/084,080.

Figure 26:
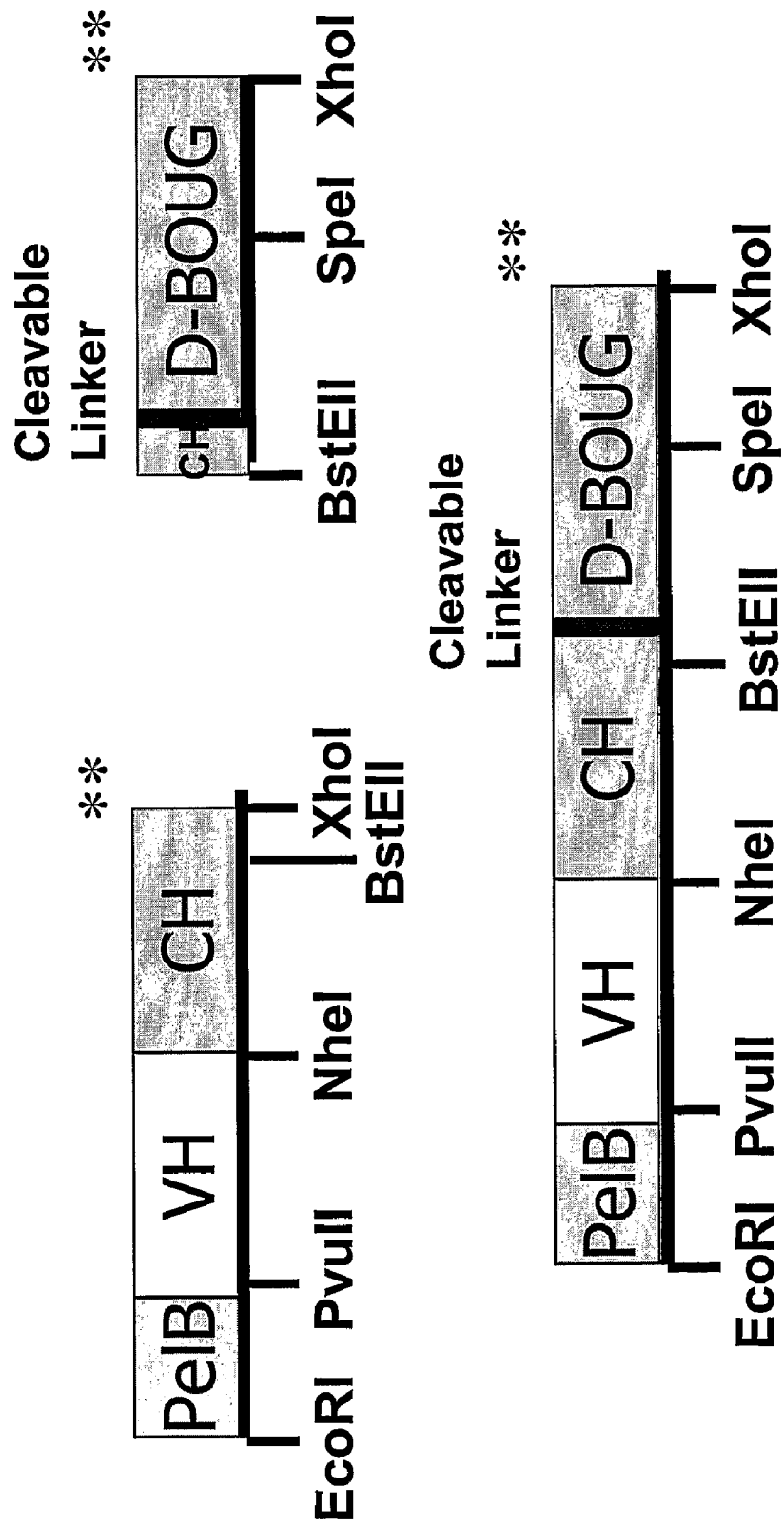
FIG. 26 is a depiction of the gamma cassette.

A dicistronic expression unit was generated comprising the VH-CH domain of VB1-008 linked to modified bouganin using a furin-sensitive linker immediately followed by the VL-CL of VB1-008 domain. Both the VH and VL were preceded by a PeIB leader sequence (See FIGS. 26 and 27). The dicistronic unit was cloned into the pING3302 Xoma vector and was under the control of the arabinose-inducible araBAD promoter. The presence of the PeIB leader sequence, adjacent to VH-CH Bouganin and VL-CL, will result in secretion of the proteins into the periplasmic space where the reducing environment will allow the formation of the disulphide bridge between the two constant domains. Ultimately, the Fab-bouganin fusion protein will be secreted into the culture supernatant. A histidine affinity tag, placed at the N-terminal of the VL-CL enables the Fab-bouganin protein to be purified using a $Ni^{2+}$-chelating capture method. The VH fragment of VB6-008 (395 bp) was amplified with the following primers and cloned into PeIB-VB6-011-F-boug gamma cassette using PvuII and NheI restriction sites.

```
5' PvuII-QVQL
                                        (SEQ ID NO: 30)
5' ATG GCG CAG GTG CAG CTG CAG GAG TTG GGT CCA

3' VB4-008-NheI
                                        (SEQ ID NO: 31)
5' CGA TGG GCC CTT GGT GGA GGC GCT AGC GAC AGT GAC

CAT TGT CCC
```

VB1-008 light chain is a lambda and since the lambda CL domain contains a SpeI restriction site, a different restriction site was used to assemble VB6-008. Therefore, in the 5' end of the VB6-008 light chain fragment, the HindIII restriction site (in bouganin) was used to assemble the final construct into pSP73 plasmid (See FIG. 27). No restriction site was found around the VL-CL junction therefore the VL-CL of each clones was obtained by the Splice Overlapping Extension PCR approach. The following primers were used along with D-bouganin 156, PeIB signal and cDNA of VB1-008 hybridoma as templates:

HindIII-boug-PeIB-VB6-008 lambda was assembled by the Splice Overlapping Extension Polymerase Chain Reaction method using the following primers:

```
5' Furin Linker D-bouganin
                                        (SEQ ID NO: 32)
5' CAC AGG CAG CCC AGA GGC TGG GAG CAG CTC TAC AAC

ACC GTG TCA TTT AAC CTT

3' 008-PelB
                                        (SEQ ID NO: 33)
5' CGT TCC ATA GAC CTG CAG TCT AGA GTC GAC TCA CTA

TTT GGA GCT TTT AAA CTT

5' PelB-SalI
                                        (SEQ ID NO: 34)
5' AAG TTT AAA AGC TCC AAA TAG TGA TCT AGA GTC GAC

CTG CAG GTC TAT GGA ACG ATA AAT

3' 008-VL CL
                                        (SEQ ID NO: 35)
5' CAC TGA GGG TGG CTG AGT CAG CTC ATA GTG ATG GTG

GTA GTG AGT

5' 008-VL CL
                                        (SEQ ID NO: 36)
5' CAT CAC CAT CAC CAT CAC TAT GAG CTG ACT CAG CCA

CCC TCA GTG

3' 008 CL STOP
                                        (SEQ ID NO: 37)
5' CTC GAG TCA CTA TGA ACA TTC TGT AGG GGC CAC TGT

CTT CTC CAC
```

A three-step Splice Overlapping Extension PCR approach was undertaken using all 6 primers listed above for amplification.

Step 1

Primers 1 and 2 was used to amplify bouganin containing a portion of the PeIB promoter (820 bp) in the 3' end. In a second PCR reaction, primers 3 and 4 was used to amplify the PeIB containing in the 3' end a His tag and a portion of VB6-008 VL (179 bp). In a third PCR reaction, primers 5 and 6 was used to amplify the VB6-008 lambda chain with two stop codons and the XhoI site (666 bp) in the 3' end.

Step 2

In the second PCR reaction, primers 1 and 6 was used with 1 μl from each PCR product to produce the HindIII-bouganin-PeIB-VB6-008 lambda chain (1591 bp).

Electrophoresis on a 1% agarose gel was used to separate the amplified PCR products. The bands of interest was excised and purified using a Qiaquick gel extraction kit, cloned into the TOPO pCR 2.1 cloning vector and sequenced using the 373 DNA sequencer.

Figure 27:
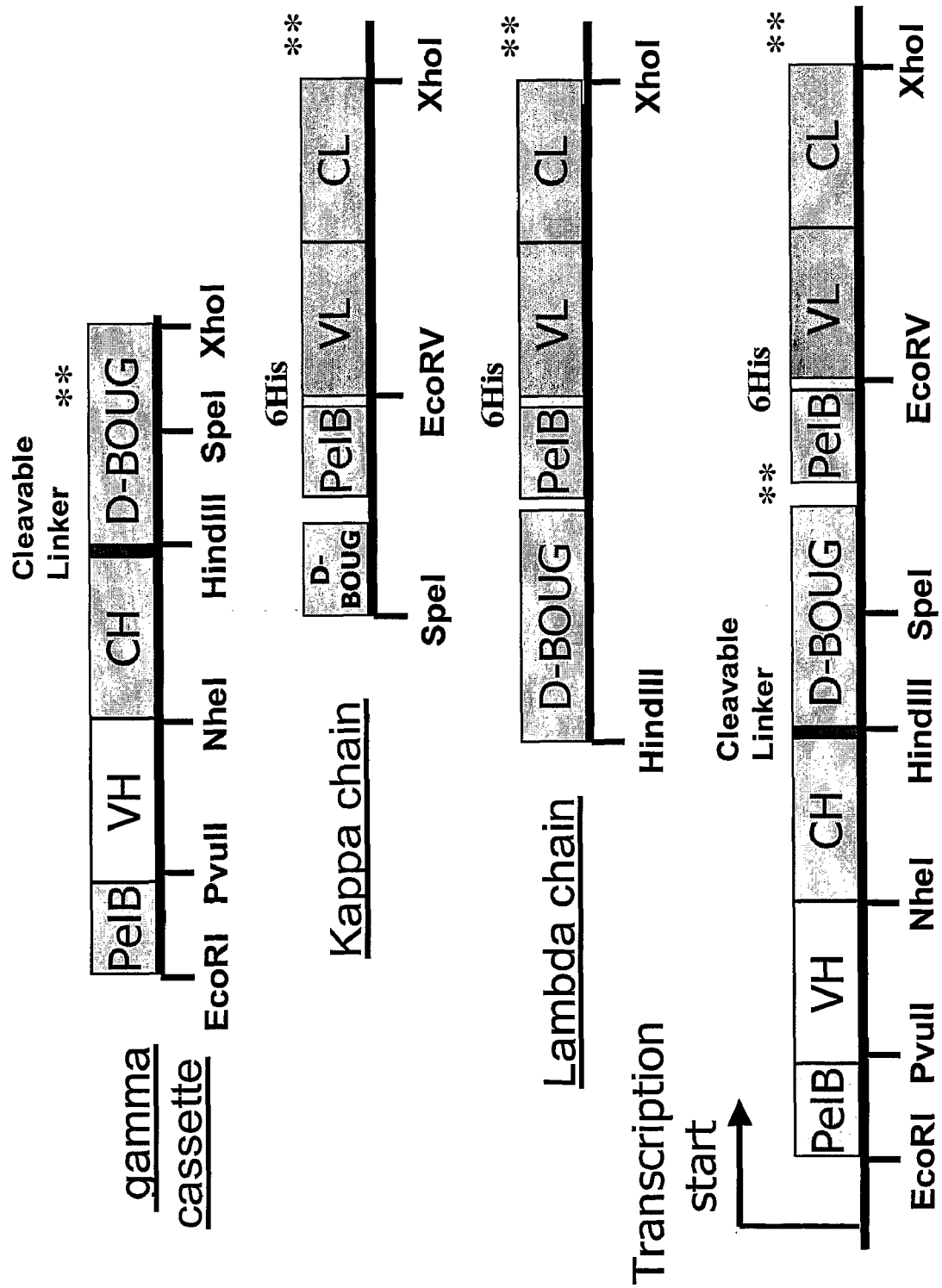
FIG. 27 is a depiction of the assembly of the Fab-bouganin immunotoxin.

The PCR product was purified and sequenced. A verified clone was digested with HindIII and XhoI and ligated into the PeIB-VB4-008-F-boug/pSP73 previously digested with the corresponding enzymes (FIG. 27). The VB6-008 fragment was then be digested with EcoRI and XhoI and cloned into the pING3302 expression vector and transformed into E104 cells.

E104 cells were propagated in 30 mL of TB media (1% innoculum) in a 250 mL shake flask at 37° C., shaken at 225 rpm for approximately 5 hours until the optical density (O.D. 600 nm) reached 2. At this time, the culture was induced with a final concentration of 0.1% L-(+) arabinose for 16 hours and incubated at 25° C. Subsequently, the cell pellet and supernatant was collected by centrifugation at 14000 rpm for 5 minutes. Both the cell pellet and supernatant was analyzed by Western blot using an anti-His (Amersham Biosciences 27-4710-01) and an anti-human kappa light chain (Sigma A-7164) or anti-human lambda light chain (Sigma A-5175) under reducing and non-reducing conditions to confirm the presence and size of the immunotoxin. A Research Cell Bank of the clone with the highest expression level was made and three independent vials will be tested for induction at a scale of 500 mL TB in 2 L shake flasks. Every 6 hours, the cell pellet and supernatant was isolated and Western blot analysis was used to indicate the optimal post-induction time for harvesting.

Flow cytometry was used to demonstrate that the purified VB6 immunotoxins retain the binding specificity of their respective parent antibody using antigen positive and negative cell lines. Binding will be detected using a mouse anti-His monoclonal antibody (Amersham Biosciences 27-4710-01). The specificity of the binding was assessed by competition assay. Briefly, the VB6-immunotoxin (at a fixed concentration) and the corresponding VB1 antibody or an isotype-matched control antibody (at varying concentrations) was incubated simultaneously with antigen positive cells. Binding was detected using a mouse anti-His monoclonal antibody. Decreased binding using the anti-His monoclonal antibody indicated that the VB6 immunotoxins and the corresponding VB1 antibody bind to the same antigen. It is expected that the level of binding of the VB6 immunotoxins will not be altered in the presence of the isotype-matched control antibody. The functional affinity of the VB6 immunotoxins was calculated with a titration curve using an anti-gen positive cell line. An MTS assay was used to measure the $IC_{50}$ of each VB6 immunotoxin using antigen positive and negative cell lines. VB6-4B5 was used as a negative control.

The specificity of the cytotoxicity was measured by the difference in $IC_{50}$ between the VB6 immunotoxins and VB6-4B5.

Results

Figure 22:
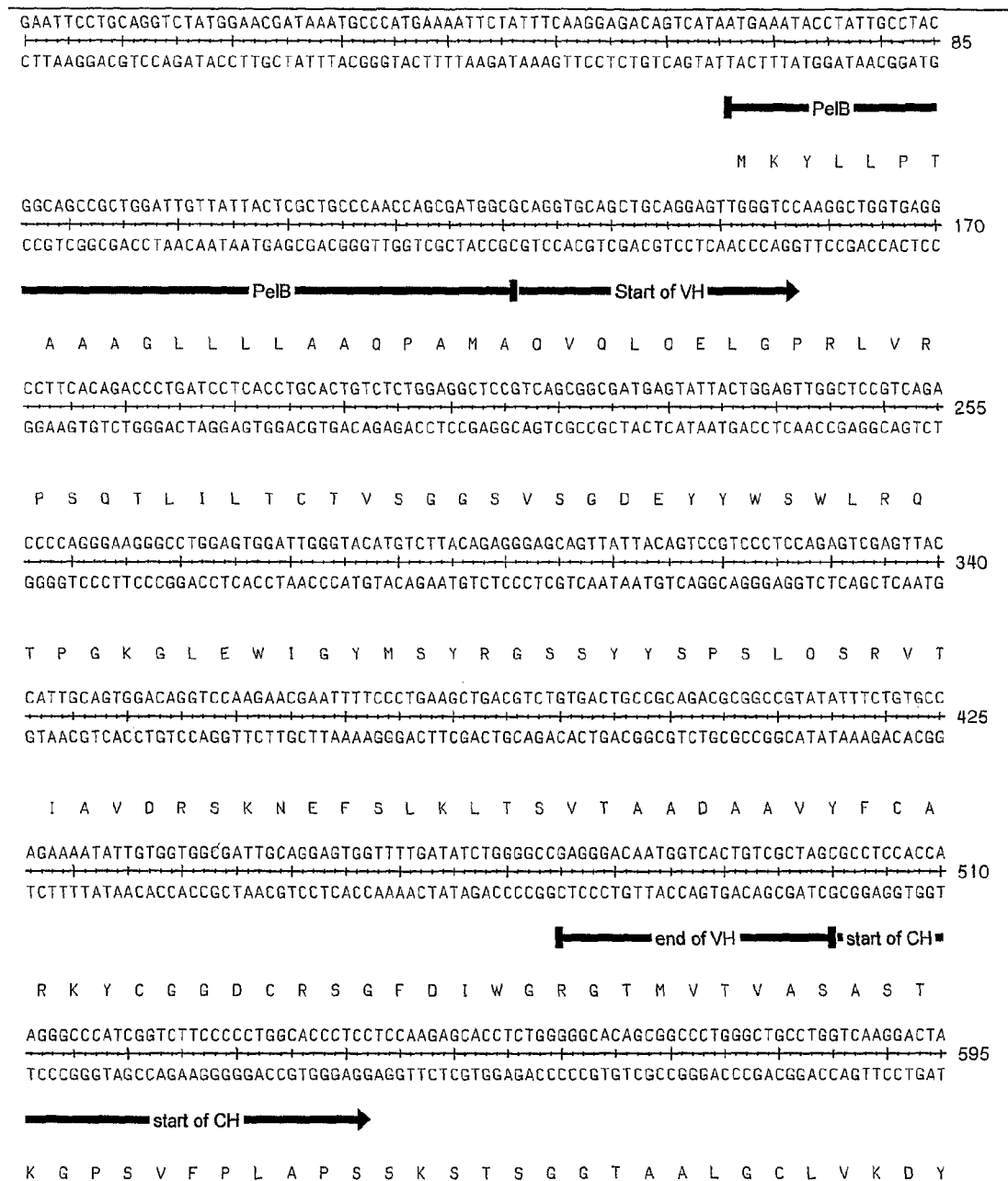
FIG. 22 shows the complete VB6-008 construct (SEQ ID NOS: 81, 82 and 83).

An immunoconjugate (VB6-008) comprising VB1-008 attached to a modified bouganin was constructed. The nucleotide sequence of the immunoconjugate is depicted in FIG. 20 (SEQ ID NO:11). The amino acid sequence of the immunoconjugate is depicted in FIG. 21 (SEQ ID NO:12). FIG. 22 shows the complete VB6-008 construct. FIG. 23 shows VB6-008 unit #1, which includes PeIB-VH-CH-Furin-De-Bouganin. FIG. 24 shows VB6-008 unit #2, which consists of PeIB-VL-CL.

The cytotoxicity of VB6-008 was assessed in vitro against the antigen-positive cells, MB-435SC. Colo-320 was used as the negative control. The cells were incubated with VB8-008 ranging from 1000 to 1 nm and after 5 days of incubation variability was measured. As can be seen, in FIG. 25, the VB6-008 immunoconjugate significantly killed the antigen-positive cells as compared to the negative control.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

CDR Sequences

VB1-008

| | L-chain | | H-chain | |
|---|---|---|---|---|
| CDR1 | SGDNLGNKYVC | SEQ ID NO:1 | GDEYYWS | SEQ ID NO:4 |
| CDR2 | EDTKRPS | SEQ ID NO:2 | YMSYRGSSYYSPSLQS | SEQ ID NO:5 |
| CDR3 | QAWDSRTEI | SEQ ID NO:3 | KYCGGDCRSGFDI | SEQ ID NO:6 |

TABLE 2

Comparison of normal and tumor cell surface binding with VB1-008

| Clinical Indication | Representative Tumor Cell lines | N[1] | MF[2] | Relative Rank |
|---|---|---|---|---|
| Breast | MCF-7, MDA-MB-231, MDA-MB-435S | 3 | 17.2 | 1 |
| Lung | A-549, NCI-H460, NCI-H69 | 3 | 16.1 | 2 |
| Melanoma | A-375, SK-MEL-5[a,b], SK-MEL-28[a] | 3 | 15.6 | 3 |
| Prostate | DU-145[a,b,f], PC-3[a,b,g], LNCaP[a,b,g] | 3 | 14.2 | 4 |
| Ovarian | SK-OV-3[a], OVCar-3 | 2 | 10.8 | 5 |
| Kidney | Caki-1[a], A498[a], ACHN[a] | 3 | 10.5 | 6 |
| Liver | SK-HEP-1, Hep-G2 | 2 | 8.3 | 7 |
| Rectum | SW837, NCI-H630 | 2 | 7.5 | 8 |
| Colon | HT-29[a], SW480, WiDr | 3 | 7.2 | 9 |
| Cervix | HeLa, C-41, C-33A | 3 | 4.4 | 10 |
| Stomach | AGS, NCI-N-87, KATO III | 3 | 4.0 | 11 |
| Bladder | UM-UC-3, T24 | 2 | 3.9 | 12 |
| Endometrium | RL-95-2, HEC-1-A | 2 | 3.9 | 12 |
| Pancreas | PANC-1, BxPC-3, MIA PaCa-2 | 3 | 3.8 | 14 |
| Head & Neck | SCC-15, SCC-25 | 2 | 2.9 | 15 |

| Normal Cell Type | Cell Line | | | Tumor:normal |
|---|---|---|---|---|
| Kidney | HRE | 1 | 6.1 | 1.7 |
| Lung | NHLF | 1 | 5.6 | 2.9 |
| Endothelial | HUVEC | 1 | 1.6 | N/A |
| Breast | HMEC | 1 | 2.4 | 7.2 |
| Prostate | PrEC | 1 | 4.0 | 3.6 |

[1]N indicates the number of cell lines tested per indication.
[2]MF: Values indicate the mean calculated from the sum of the mean fold increase in median fluorescence over the control antibody from all cell lines in each indication. A zero value indicates no measurable reactivity relative to the control antibody.
[a]Indicates orthotopic models offered by AntiCancer Inc.
[b]Indicates cell lines available as GFP (green fluorescent protein)-transfectants.
[c]Her2/neu−, ER+.
[d]Her2/neu−, ER−, p53[wt], ras[wt].
[e]Her2/neu−, ER−, p53[mt], ras[wt].
[f]Androgen-responsive.
[g]Androgen-unresponsive.
N/A, not applicable.
The mean-fold increase (MF) is used to calculate the tumor:normal ratio.

TABLE 3

LD Array of Critical Normal Tissue for VB1-008

| Tissue | Membrane Staining | Score Range* |
|---|---|---|
| Brain | None (0/2) | 0 |
| Colon | None (0/5) | 0 |
| Heart | None (0/5) | 0 |
| Kidney | 2/3 | 0-1 (10%) |
| Liver | None (0/5) | 0 |
| Lung | None (0/5) | 0 |
| Pancreas | 1/5 | 1 (30%) |
| Stomach | 1/5 | 1 (70%) |

*Scoring was evaluated on a 0-3+ scale, with 0 = no staining and trace being less than 1+ but greater than 0. Grades 1+ to 3+ represent increased intensity of staining, with 3+ being strong, dark brown staining. In general, a single specimen of 6 different patients was screened. Where fewer than 6 patients were screened indicates cores were either missing or were not representative of the tissue to be stained. Values in parentheses indicate the percentage of cells stained in the scored range.

TABLE 4

HD Normal TMA for VB1-008

| Tissue | Membrane Staining | Score Range* |
|---|---|---|
| Adrenal | None (0/2) | 0 |
| Aorta | None (0/5) | 0 |
| Artery | None (0/5) | 0 |
| Bladder | None (0/5) | 0 |
| Brain | None (0/5) | 0 |
| Breast | None (0/5) | 0 |
| Fallopian tube | 3/4 | 1-2 (30-60%) |
| LN | None (0/3) | 0 |
| Muscle | None (0/4) | 0 |
| Ovary | None (0/5) | 0 |
| Pituitary | None (0/5) | 0 |
| Placenta | None (0/4) | 0 |
| Prostate | 4/5 | 0-1 (10-20%) |
| Skin | ND | |
| Spinal cord | None (0/1) | 0 |
| Spleen | None (0/2) | 0 |
| Testis | 3/5 | 1-2 (95%) |
| Thymus | None (0/1) | 0 |
| Thyroid | None (0/5) | 0 |
| Ureter | 1/2 | |
| Uterus | None (0/5) | 0 |

*Scoring was evaluated on a 0-3+ scale, with 0 = no staining and trace being less than 1+ but greater than 0. Grades 1+ to 3+ represent increased intensity of staining, with 3+ being strong, dark brown staining. In general, 2 specimens of 8 different patients were screened. Where fewer than 8 patients were screened indicates cores were either missing or were not representative of the tissue to be stained. Values in parentheses indicate the percentage of cells stained in the scored range.

TABLE 5

HD Tumor TMA for VB1-008

| Tissue | Membrane Staining | Score Range* |
|---|---|---|
| Bladder | 6/6 | 1-2 (100%) |
| Breast | 6/7 | 1-2 (100%) |
| Cervix | 2/7 | 1 (100%) |
| Colon | 3/3 | 1-2 (100%) |
| Kidney | 5/8 | 1-2 (100%) |
| Liver | 5/7 | 1-2 (100%) |
| Lung | 1/8 | 1 (100%) |
| Ovary | 6/7 | 1-2 (100%) |
| Pancreas | 4/7 | 1 (100%) |
| Prostate | 5/5 | 1-2 (100%) |
| Rectum | 4/6 | 1-2 (100%) |
| Skin | 1/4 | 1 (100%) |
| Stomach | 4/5 | 1-2 (100%) |
| Uterus | 8/8 | 1-2 (100%) |
| Head & Neck | 4/8 | 1 (100%) |

*Scoring was evaluated on a 0-3+ scale, with 0 = no staining and trace being less than 1+ but greater than 0. Grades 1+ to 3+ represent increased intensity of staining, with 3+ being strong, dark brown staining. In general, 2 specimens of 8 different patients were screened. Where fewer than 8 proteins were screened indicates cores were either missing or were not representative of the tissue to be stained. Head & neck cancers included carcinomas of the throat, lip, larynx, mouth, tonsil, and gingival surface. Values in parentheses indicate the percentage of cells stained in the scored range.

TABLE 6

Flow cytometry assessment of antibody binding as a function of time and temperature

| MAb ID | Anti-bodies[1] | Incubation Time (min) at 37° C. | Median Fluorescence (MF) | Fold-increase in MF[2] | % Reduction in MF[3] |
|---|---|---|---|---|---|
| VB1-008 | 17P2/C12 | —[4] | 134.0 ± 11 | 31.7 | — |
| | | 60 | 57.0 ± 1.0 | 13.5 | 57.5 |
| | | 120 | 50.7 ± 1.1 | 12.0 | 62.2 |
| Non-Internalizing Control | MA-103 | — | 536.1 ± 31.3 | 112.8 | — |
| | | 120 | 535.5 ± 16.8 | 113.0 | — |
| Internalizing | 5E9 | — | 246 ± 11 | 60.0 | — |
| | | 60 | 53.5 ± 1.5 | 13.0 | 78.3 |
| Control | | 120 | 48 ± 4 | 11.7 | 80.5 |

[1] A representative experiment is shown.
[2] MF increase above the negative control, mouse myeloma IgG or human IgG (4B5).
[3] Percent reduction of MF from the cell-surface of tumor cells.
[4] — cells incubated on ice for 120 minutes.

TABLE 7

Increase in median fluorescence for VB1-008 over an isotype-matched control for each cell line used in the study

| Cell line | MF* |
|---|---|
| A-375 | 13.3 |
| MDA-MB-435S | 15.8 |
| MDA-MB-231 | 14.2 |
| MCF-7 | 4.67 |
| PANC-1 | 8.3 |
| DAUDI | 1.1 |
| RAMOS | 1.3 |

TABLE 8

Summary of the antigens purified

| | Sample preparation | | | |
|---|---|---|---|---|
| Cell line | reduced | non-reduced | Flow results | intensity |
| A-375 | 50 ± 2 kDa | 100 ± 5 kDa | 11.08 | +++ |
| MB435S | 50 ± 2 kDa | 100 ± 5 kDa | 15.8 | ++++ |
| MB231 | 50 ± 2 kDa | 100 ± 5 kDa | 14.2 | ++ |
| MCF-7 | 50 ± 2 kDa | 100 ± 5 kDa | 4.63 | + |
| PANC-1 | — | — | 8.95 | - |
| DAUDI | — | — | 1 | - |
| RAMOS | 50 ± 2 kDa | 100 ± 5 kDa | 1.1 | +++ |

TABLE 9A

Summary of the proteins identified by LC-MS/MS from 2D spot - 'C'
2D Spot 'C' - 48.8 kDa from MDA-MB-435S

| Accession # | Protein ID | Mw/Pi | Peptides | Match to 2DE |
|---|---|---|---|---|
| gi\|4501989 | alpha-fetoprotein [Homo sapiens] (AFP) | 68813/5.2 | 30 | ✓ |
| gi\|231315 | alpha-1proteinase inhibitor | 39099/5.27 | 7 | C |
| gi\|224224 | alpha-1 antitrypsin | 46731/4.35 | 6 | C |

C- Co-purifying contaminant;
X - does not match Pi and/or Mw observed;
✓ = matches Pi and Mw

TABLE 9B

Summary of the proteins identified by LC-MS/MS from 2D spot - 'D'
2D Spot 'D' - 45 ± 2 kDa

| Accession # | Protein ID | Mw/PI | Peptides | Match to 2DE |
|---|---|---|---|---|
| gi\|105583 | cell adhesion molecule CD44 - human | 53585/5.4 | 3 | ✓ |

TABLE 9B-continued

Summary of the proteins identified by LC-MS/MS from 2D spot - 'D'
2D Spot 'D' - 45 + 2 kDa

| Accession # | Protein ID | Mw/PI | Peptides | Match to 2DE |
|---|---|---|---|---|
| gi\|87056 | nucleolin-related protein - human | 77453/4.5 | 3 | X |
| gi\|2804273 | alpha-actinin 4 [Homo sapiens] | 102661/5.27 | 5 | C |
| gi\|34862435 | ER protein 99/integrin | 92713/4.72 | 2 | X |
| gi\|71620 | actin-beta - bovine | 41786/5.22 | 1 | C |

C- Co-purifying contaminant;
X - does not match Pi and Mw observed;
✓ = matches pI and Mw within acceptable range

TABLE 10

Summary of the proteins identified by LC-MS/MS from protein band 'E'
Protein band 'E' - 110 kDa band from VB1-008 IP
(non-reducing conditions)

| Accession # | Protein ID | Mw/PI | Peptides | Match to 2DE |
|---|---|---|---|---|
| gi\|4501989 | alpha-fetoprotein [Homo sapiens] (AFP) | 68813/5.2 | 16 | ✓ |
| Gi\|105583 | cell adhesion molecule CD44 - human | 53585/5.4 | 8 | ✓ |
| gi\|20177936 | heat shock protein Hsp90-beta[Hsp 84] | 81912/4.77 | 10 | X |
| gi\|34862435 | Alpha-actinin | 92713/4.72 | 2 | C |
| gi\|71620 | actin-beta - bovine | 41786/5.22 | 5 | C |
| gi\|55408 | vimentin [Mus musculus] | 54418/5.01 | 3 | C |

C- Co-purifying contaminant;
X - does not match Pi and Mw observed;
✓ = matches pI and Mw within acceptable range

TABLE 11A

List of peptides recovered from MS/MS for AFP

| Peptide | SEQ ID NO |
|---|---|
| YGHSDCCSQSEEGR | 46 |
| HNCFLAHK | 47 |
| FIYEIAR | 48 |
| HPFLYAPTILLWAAR | 49 |
| IIPSCCK | 50 |
| AENAVECFQTK | 51 |
| ESSLLNQHACAVMK | 52 |
| TFQAITVTK | 53 |
| LSQKFTK | 54 |
| LVLDVAHVHEHCCR | 55 |
| GDVLDCLQDGEK | 56 |
| IMSYICSQQDTLSNK | 57 |
| GQCIIHAENDEKPEGLSPNLNR | 58 |
| FLGDRDFNQFSSGEK | 59 |
| DFNQFSSGEK | 60 |
| DFNQFSSGEKNIFLASFVHEYSR | 61 |
| NIFLASFVHEYSR | 62 |
| RHPQLAVSVILR | 63 |
| HPQLAVSVILR | 64 |
| GYQELLEK | 65 |
| YIQESQALAKR | 66 |
| RSCGLFQK | 67 |
| LGEYYLQNAFLVAYTKK | 68 |
| KAPQLTSSELMAITR | 69 |
| APQLTSSELMAITR | 70 |
| MAATAATCCQLSEDKLLACGEGAADIIIGHLCIR | 71 |
| LLACGEGAADIIIGHLCIR | 72 |
| DLCQAQGVALQTMKQEFLINLVK | 73 |
| QEFLINLVK | 74 |
| QKPQITEEQLEAVIADFSGLLEK | 75 |

TABLE 11B

List of peptides recovered from MS analysis of immunopurified CD44

| | |
|---|---|
| NLQNVDMK-Exon 20 | (SEQ ID NO: 38) |
| YVQKGEYR-Exon 5 | (SEQ ID NO: 39) |
| KPSGLNGEASK-Exon 20 | (SEQ ID NO: 40) |
| YGFIEGHVVIPR-Exon 3 | (SEQ ID NO: 41) |
| TEAADLCK-Exon 2 | (SEQ ID NO: 42) |
| LVINSGNGAVEDR-Exon 19 | (SEQ ID NO: 43) |
| ESSETPDQFMTADETR-Exon 20 | (SEQ ID NO: 44) |
| TGPLSMTTQQSNSQSFSTSHEGLEED-Exon v8-v9 | (SEQ ID NO: 45) |

TABLE 12

Peptide matches between different CD44 isoforms

| CD44 isoform | Accession Number | peptide matches | homology |
|---|---|---|---|
| CD44 PGP Hutch protein | Gi\|87056 | 2 | 100% |
| CD44 E/Isoform 3 | GI\|105583/ GI\|48255939 | 8* | 100% |
| CD44 M4 isoform | GI\|346672 | 1 | 58.7% |
| CD44 Isoform 1 (parent) | GI\|48255935 | 8 | 100% |
| CD44H/CD44s Isoform 2 (standard) | GI\|48255937 | 7 | 100% |
| CD44 isoform 4 | GI\|48255941 | 7 | 100% |
| CD44 isoform 5/isoform RC | GI\|48255943 | 1 | 100% |
| CD44 isoform v3-v6 | GI\|11139066 | 2 | 100% |
| CD44 homing antigen | GI\|10432374 | 3 | 78.7% |
| CD44 T-cell antigen | GI\|13936302 | 1 | 100% |
| CD44 M3 isoform | GI\|346670 | 0 | — |

TABLE 12-continued

Peptide matches between different CD44 isoforms

| CD44 isoform | Accession Number | peptide matches | homology |
|---|---|---|---|
| CD44 isoform v6 | GI|11139062 | 0 | — |
| CD44 isoform R1, R2 | GI|87053 | 4 | 100% |

TABLE 13

Comparative binding profiles of VB1-008, anti CD44, anti-AFP and anti-EGFR

| Cell line | VB1-008 | Anti-CD44 | Anti-AFP | Ag intensity | Anti-EGFR |
|---|---|---|---|---|---|
| MB435S | 15.8 | 773.5 | 1.95 | ++++ | 33.1 |
| MB231 | 14.2 | 292 | 1.3 | ++ | 149 |

TABLE 13-continued

Comparative binding profiles of VB1-008, anti CD44, anti-AFP and anti-EGFR

| Cell line | VB1-008 | Anti-CD44 | Anti-AFP | Ag intensity | Anti-EGFR |
|---|---|---|---|---|---|
| A-375 | 13.3 | 368 | 1.3 | +++ | 16 |
| PANC-1 | 8.3 | 192.5 | 1.1 | − | 132.4 |
| MCF-7 | 4.63 | 52 | 1.1 | + | 7 |
| DAUDI | 1 | 1.6 | 1.4 | − | 1.1 |
| RAMOS | 1.1 | 1.3 | 1.3 | +++ | 1.2 |

SEQUENCE LISTING

```
<160> NUMBER OF SEQ ID NOS: 87

<210> SEQ ID NO 1
<211> LENGTH: 11
<212> TYPE: PRT
<213> ORGANISM: Homo sapiens

<400> SEQUENCE: 1

Ser Gly Asp Asn Leu Gly Asn Lys Tyr Val Cys
1               5                   10

<210> SEQ ID NO 2
<211> LENGTH: 7
<212> TYPE: PRT
<213> ORGANISM: Homo sapiens

<400> SEQUENCE: 2

Glu Asp Thr Lys Arg Pro Ser
1               5

<210> SEQ ID NO 3
<211> LENGTH: 9
<212> TYPE: PRT
<213> ORGANISM: Homo sapiens

<400> SEQUENCE: 3

Gln Ala Trp Asp Ser Arg Thr Glu Ile
1               5

<210> SEQ ID NO 4
<211> LENGTH: 7
<212> TYPE: PRT
<213> ORGANISM: Homo sapiens

<400> SEQUENCE: 4

Gly Asp Glu Tyr Tyr Trp Ser
1               5

<210> SEQ ID NO 5
<211> LENGTH: 16
<212> TYPE: PRT
<213> ORGANISM: Homo sapiens

<400> SEQUENCE: 5
```

Tyr Met Ser Tyr Arg Gly Ser Ser Tyr Tyr Ser Pro Ser Leu Gln Ser
1               5                   10                  15

<210> SEQ ID NO 6
<211> LENGTH: 13
<212> TYPE: PRT
<213> ORGANISM: Homo sapiens

<400> SEQUENCE: 6

Lys Tyr Cys Gly Gly Asp Cys Arg Ser Gly Phe Asp Ile
1               5                   10

<210> SEQ ID NO 7
<211> LENGTH: 106
<212> TYPE: PRT
<213> ORGANISM: Homo sapiens

<400> SEQUENCE: 7

Tyr Glu Leu Thr Gln Pro Pro Ser Val Ser Val Ser Pro Gly Gln Lys
1               5                   10                  15

Ala Phe Ile Thr Cys Ser Gly Asp Asn Leu Gly Asn Lys Tyr Val Cys
                20                  25                  30

Trp Tyr Gln Gln Lys Pro Gly Gln Ser Pro Val Leu Val Ile Tyr Glu
            35                  40                  45

Asp Thr Lys Arg Pro Ser Gly Ile Pro Glu Arg Phe Ser Ala Ser Asn
        50                  55                  60

Ser Gly Asn Thr Ala Thr Leu Thr Ile Ser Gly Thr Gln Pro Ile Asp
65                  70                  75                  80

Glu Ala Asp Tyr Tyr Cys Gln Ala Trp Asp Ser Arg Thr Glu Ile Phe
                85                  90                  95

Gly Thr Gly Thr Lys Val Thr Val Leu Ser
            100                 105

<210> SEQ ID NO 8
<211> LENGTH: 318
<212> TYPE: DNA
<213> ORGANISM: Homo sapiens

<400> SEQUENCE: 8
tatgagctga ctcagccacc ctcagtgtcc gtgtccccag gacagaaagc cttcataacc      60
tgctctggag ataacctggg aataaaatat gtgtgctggt atcaacagaa gccaggccag     120
tcccctgtcc tggtcatcta tgaagatacc aagaggccct cagggatccc tgagcgattc     180
tctgcctcca actctgggaa tacagccact ctgaccatca gcgggacgca gcctatagat     240
gaggctgact actactgtca ggcgtgggac agccgcactg aaatcttcgg aactgggacc     300
aaggtcaccg tcctaagt                                                  318

<210> SEQ ID NO 9
<211> LENGTH: 123
<212> TYPE: PRT
<213> ORGANISM: Homo sapiens

<400> SEQUENCE: 9

Gln Val Gln Leu Gln Glu Leu Gly Pro Arg Leu Val Arg Pro Ser Gln
1               5                   10                  15

Thr Leu Ile Leu Thr Cys Thr Val Ser Gly Gly Ser Val Ser Gly Asp
                20                  25                  30

Glu Tyr Tyr Trp Ser Trp Leu Arg Gln Thr Pro Gly Lys Gly Leu Glu
            35                  40                  45

Trp Ile Gly Tyr Met Ser Tyr Arg Gly Ser Ser Tyr Tyr Ser Pro Ser
 50                  55                  60

Leu Gln Ser Arg Val Thr Ile Ala Val Asp Arg Ser Lys Asn Glu Phe
 65                  70                  75                  80

Ser Leu Lys Leu Thr Ser Val Thr Ala Ala Asp Ala Ala Val Tyr Phe
                 85                  90                  95

Cys Ala Arg Lys Tyr Cys Gly Gly Asp Cys Arg Ser Gly Phe Asp Ile
            100                 105                 110

Trp Gly Arg Gly Thr Met Val Thr Val Ala Ser
        115                 120

<210> SEQ ID NO 10
<211> LENGTH: 369
<212> TYPE: DNA
<213> ORGANISM: Homo sapiens

<400> SEQUENCE: 10

```
caggtgcagc tgcaggagtt gggtccaagg ctggtgaggc cttcacagac cctgatcctc        60
acctgcactg tctctggagg ctccgtcagc ggcgatgagt attactggag ttggctccgt       120
cagaccccag ggaagggcct ggagtggatt gggtacatgt cttacagagg gagcagttat       180
tacagtccgt ccctccagag tcgagttacc attgcagtgg acaggtccaa gaacgaattt       240
tccctgaagc tgacgtctgt gactgccgca gacgcggccg tatatttctg tgccagaaaa       300
tattgtggtg gcgattgcag gagtggtttt gatatctggg gccgaggaca atggtcacc        360 gtcgcttca                                                               369
```

<210> SEQ ID NO 11
<211> LENGTH: 2400
<212> TYPE: DNA
<213> ORGANISM: Homo sapiens

<400> SEQUENCE: 11

```
gaattcctgc aggtctatgg aacgataaat gcccatgaaa attctatttc aaggagacag        60
tcataatgaa atacctattg cctacggcag ccgctggatt gttattactc gctgcccaac       120
cagcgatggc gcaggtgcag ctgcaggagt gggtccaag gctggtgagg ccttcacaga       180
ccctgatcct cacctgcact gtctctggag gctccgtcag cggcgatgag tattactgga       240
gttggctccg tcagacccca gggaagggcc tggagtggat tgggtacatg tcttacagag       300
ggagcagtta ttacagtccg tccctccaga gtcgagttac cattgcagtg gacaggtcca       360
agaacgaatt ttccctgaag ctgacgtctg tgactgccgc agacgcggcc gtatatttct       420
gtgccagaaa atattgtggt ggcgattgca ggagtggttt tgatatctgg ggccgaggga       480
caatggtcac tgtcgctagc gcctccacca agggcccatc ggtcttcccc ctggcaccct       540
cctccaaggc acctctgggg gcacagcggc cctgggctgc ctggtcaagg actacttccc       600
cgaaccggtg acggtgtcgt ggaactcagg cgccctgacc agcggcgtgc acaccttccc       660
ggctgtccta cagtcctcag gactctactc cctcagcagc gtggtgaccg tgccctccag       720
cagcttgggc acccagacct acatctgcaa cgtgaatcac aagcccagca acaccaaggt       780
ggacaagaaa gttgagccca atcttgtac caggcacagg cagcccagag ctgggagca        840 gctctacaac actgtgtcat ttaaccttgg agaagcttat gagtacccca cttttataca       900
agatttgcgc aatgaattgg ctaagggcac accagtatgt caacttccag tgacactaca       960
aaccatagcc gatgacaagc gatttgttct agttgatatc actacgacct cgaagaaaac      1020
```

```
agttaaggtt gctatagatg tgacagatgt gtatgttgtg ggttatcaag acaaatggga    1080
tggcaaagat cgagctgttt tccttgacaa ggttcctact gttgcaacta gtaaactttt    1140
cccaggggtg actaatcgtg taacgttaac atttgatggc agctatcaga acttgtgaa     1200 tgctgccaaa gctgatagaa aggctctcga actgggggtt aacaaattgg aattttccat    1260
tgaagcaatc catggtaaaa cgataaatgg tcaagaggca gccaagttct ttcttattgt    1320
catccaaatg gtttcagagg cagctcggtt caaatatatt gagactgagg tggttgatag    1380
aggattatat ggatcattca aacctaattt taaagtattg aacttggaga caattggggg    1440
cgacatctct gatgccattc acaaatcatc cccacaatgt accactatta atccggcact    1500
tcagttgata agcccctcaa atgacccatg ggttgtaaat aaagtgagtc aaattagtcc    1560
cgatatgggt atccttaagt ttaaaagctc aaatagtga gtcgactcta gactgcaggt     1620
ctatggaacg ataaatgccc atgaaaattc tatttcaagg agacagtcat aatgaaatac    1680
ctattgccta cggcagccgc tggattgtta ttactcgctg cccaaccagc gatggcgcat    1740
caccatcacc atcactatga gctgactcag ccaccctcag tgtccgtgtc cccaggacag    1800
aaagccttca taacctgctc tggagataac ctggggaata aatatgtgtg ctggtatcaa    1860
cagaagccag gccagtcccc tgtcctggtc atctatgaag ataccaagag gccctcaggg    1920
atccctgagc gattctctgc ctccaactct gggaatacag ccactctgac catcagcggg    1980
acgcagccta tagatgaggc tgactactac tgtcaggcgt gggacagccg cactgaaatc    2040
ttcggaactg ggaccaaggt caccgtccta agtcagccca aggccaaccc cactgtcact    2100
ctgttcccgc cctcctctga ggagctccaa gccaacaagg ccacactagt gtgtctgatc    2160
agtgacttct acccgggagc tgtgacagtg gcctggaagg cagatggcag ccccgtcaag    2220
gcgggagtgg agaccaccaa accctccaaa cagagcaaca caagtacgc ggccagcagc     2280 tacctgagcc tgacgcccga gcagtggaag tcccacagaa gctacagctg ccaggtcacg    2340
catgaaggga gcaccgtgga agacagtg gccctacag aatgttcata gtgactcgag         2400
```

<210> SEQ ID NO 12
<211> LENGTH: 510
<212> TYPE: PRT
<213> ORGANISM: Homo sapiens

<400> SEQUENCE: 12

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Leu Gly Pro Arg
            20                  25                  30

Leu Val Arg Pro Ser Gln Thr Leu Ile Leu Thr Cys Thr Val Ser Gly
        35                  40                  45

Gly Ser Val Ser Gly Asp Glu Tyr Tyr Trp Ser Trp Leu Arg Gln Thr
    50                  55                  60

Pro Gly Lys Gly Leu Glu Trp Ile Gly Tyr Met Ser Tyr Arg Gly Ser
65                  70                  75                  80

Ser Tyr Tyr Ser Pro Ser Leu Gln Ser Arg Val Thr Ile Ala Val Asp
                85                  90                  95

Arg Ser Lys Asn Glu Phe Ser Leu Lys Leu Thr Ser Val Thr Ala Ala
            100                 105                 110

Asp Ala Ala Val Tyr Phe Cys Ala Arg Lys Tyr Cys Gly Gly Asp Cys
        115                 120                 125

Arg Ser Gly Phe Asp Ile Trp Gly Arg Gly Thr Met Val Thr Val Ala
    130                 135                 140
```

```
Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Thr Arg His Arg Gln Pro Arg Gly
                245                 250                 255

Trp Glu Gln Leu Tyr Asn Thr Val Ser Phe Asn Leu Gly Glu Ala Tyr
            260                 265                 270

Glu Tyr Pro Thr Phe Ile Gln Asp Leu Arg Asn Glu Leu Ala Lys Gly
        275                 280                 285

Thr Pro Val Cys Gln Leu Pro Val Thr Leu Gln Thr Ile Ala Asp Asp
290                 295                 300

Lys Arg Phe Val Leu Val Asp Ile Thr Thr Ser Lys Lys Thr Val
305                 310                 315                 320

Lys Val Ala Ile Asp Val Thr Asp Val Tyr Val Gly Tyr Gln Asp
                325                 330                 335

Lys Trp Asp Gly Lys Asp Arg Ala Val Phe Leu Asp Lys Val Pro Thr
            340                 345                 350

Val Ala Thr Ser Lys Leu Phe Pro Gly Val Thr Asn Arg Val Thr Leu
        355                 360                 365

Thr Phe Asp Gly Ser Tyr Gln Lys Leu Val Asn Ala Ala Lys Ala Asp
370                 375                 380

Arg Lys Ala Leu Glu Leu Gly Val Asn Lys Leu Glu Phe Ser Ile Glu
385                 390                 395                 400

Ala Ile His Gly Lys Thr Ile Asn Gly Gln Glu Ala Ala Lys Phe Phe
                405                 410                 415

Leu Ile Val Ile Gln Met Val Ser Glu Ala Ala Arg Phe Lys Tyr Ile
            420                 425                 430

Glu Thr Glu Val Val Asp Arg Gly Leu Tyr Gly Ser Phe Lys Pro Asn
        435                 440                 445

Phe Lys Val Leu Asn Leu Glu Asn Asn Trp Gly Asp Ile Ser Asp Ala
450                 455                 460

Ile His Lys Ser Ser Pro Gln Cys Thr Thr Ile Asn Pro Ala Leu Gln
465                 470                 475                 480

Leu Ile Ser Pro Ser Asn Asp Pro Trp Val Val Asn Lys Val Ser Gln
                485                 490                 495

Ile Ser Pro Asp Met Gly Ile Leu Lys Phe Lys Ser Ser Lys
            500                 505                 510

<210> SEQ ID NO 13
<211> LENGTH: 239
<212> TYPE: PRT
<213> ORGANISM: Homo sapiens

<400> SEQUENCE: 13

Met Lys Tyr Leu Leu Pro Thr Ala Ala Ala Gly Leu Leu Leu Leu Ala
1               5                   10                  15
```

```
Ala Gln Pro Ala Met Ala His His His His His Tyr Glu Leu Thr
            20                  25                  30

Gln Pro Pro Ser Val Ser Val Ser Pro Gly Gln Lys Ala Phe Ile Thr
                35                  40                  45

Cys Ser Gly Asp Asn Leu Gly Asn Lys Tyr Val Cys Trp Tyr Gln Gln
 50                  55                  60

Lys Pro Gly Gln Ser Pro Val Leu Val Ile Tyr Glu Asp Thr Lys Arg
 65                  70                  75                  80

Pro Ser Gly Ile Pro Glu Arg Phe Ser Ala Ser Asn Ser Gly Asn Thr
                85                  90                  95

Ala Thr Leu Thr Ile Ser Gly Thr Gln Pro Ile Asp Glu Ala Asp Tyr
            100                 105                 110

Tyr Cys Gln Ala Trp Asp Ser Arg Thr Glu Ile Phe Gly Thr Gly Thr
        115                 120                 125

Lys Val Thr Val Leu Ser Gln Pro Lys Ala Asn Pro Thr Val Thr Leu
130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Gly Ser Pro Val Lys Ala Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Gln Val Thr His
210                 215                 220

Glu Gly Ser Thr Val Glu Lys Thr Val Ala Pro Thr Glu Cys Ser
225                 230                 235

<210> SEQ ID NO 14
<211> LENGTH: 381
<212> TYPE: PRT
<213> ORGANISM: Homo sapiens

<400> SEQUENCE: 14

Lys Tyr Gly His Ser Asp Cys Cys Ser Gln Ser Glu Glu Gly Arg His
 1               5                  10                  15

Asn Cys Phe Leu Ala His Lys Lys Pro Thr Pro Ala Ser Ile Pro Leu
            20                  25                  30

Phe Gln Val Pro Glu Pro Val Thr Ser Cys Glu Ala Tyr Glu Glu Asp
        35                  40                  45

Arg Glu Thr Phe Met Asn Lys Phe Ile Tyr Glu Ile Ala Arg Arg His
 50                  55                  60

Pro Phe Leu Tyr Ala Pro Thr Ile Leu Leu Trp Ala Ala Arg Tyr Asp
 65                  70                  75                  80

Lys Ile Ile Pro Ser Cys Cys Lys Ala Glu Asn Ala Val Glu Cys Phe
                85                  90                  95

Gln Thr Lys Ala Ala Thr Val Thr Lys Glu Leu Arg Glu Ser Ser Leu
            100                 105                 110

Leu Asn Gln His Ala Cys Ala Val Met Lys Asn Phe Gly Thr Arg Thr
        115                 120                 125

Phe Gln Ala Ile Thr Val Thr Lys Leu Ser Gln Lys Phe Thr Lys Val
130                 135                 140

Asn Phe Thr Glu Ile Gln Lys Leu Val Leu Asp Val Ala His Val His
145                 150                 155                 160
```

Glu His Cys Cys Arg Gly Asp Val Leu Asp Cys Leu Gln Asp Gly Glu
                165                 170                 175

Lys Ile Met Ser Tyr Ile Cys Ser Gln Gln Asp Thr Leu Ser Asn Lys
            180                 185                 190

Ile Thr Glu Cys Cys Lys Leu Thr Thr Leu Glu Arg Gly Gln Cys Ile
        195                 200                 205

Ile His Ala Glu Asn Asp Glu Lys Pro Glu Gly Leu Ser Pro Asn Leu
    210                 215                 220

Asn Arg Phe Leu Gly Asp Arg Asp Phe Asn Gln Phe Ser Ser Gly Glu
225                 230                 235                 240

Lys Asn Ile Phe Leu Ala Ser Phe Val His Glu Tyr Ser Arg Arg His
                245                 250                 255

Pro Gln Leu Ala Val Ser Val Ile Leu Arg Val Ala Lys Gly Tyr Gln
            260                 265                 270

Glu Leu Leu Glu Lys Cys Phe Gln Thr Glu Asn Pro Leu Glu Cys Gln
        275                 280                 285

Asp Lys Gly Glu Glu Glu Leu Gln Lys Tyr Ile Gln Glu Ser Gln Ala
    290                 295                 300

Leu Ala Lys Arg Ser Cys Gly Leu Phe Gln Lys Leu Gly Glu Tyr Tyr
305                 310                 315                 320

Leu Gln Asn Ala Phe Leu Val Ala Tyr Thr Lys Lys Ala Pro Gln Leu
                325                 330                 335

Thr Ser Ser Glu Leu Met Ala Ile Thr Arg Lys Met Ala Ala Thr Ala
            340                 345                 350

Ala Thr Cys Cys Gln Leu Ser Glu Asp Lys Leu Leu Ala Cys Gly Glu
        355                 360                 365

Gly Ala Ala Asp Ile Ile Ile Gly His Leu Cys Ile Arg
    370                 375                 380

<210> SEQ ID NO 15
<211> LENGTH: 484
<212> TYPE: PRT
<213> ORGANISM: Homo sapiens

<400> SEQUENCE: 15

Lys Tyr Gly His Ser Asp Cys Cys Ser Gln Ser Glu Glu Gly Arg His
1               5                   10                  15

Asn Cys Phe Leu Ala His Lys Lys Pro Thr Pro Ala Ser Ile Pro Leu
            20                  25                  30

Phe Gln Val Pro Glu Pro Val Thr Ser Cys Glu Ala Tyr Glu Glu Asp
        35                  40                  45

Arg Glu Thr Phe Met Asn Lys Phe Ile Tyr Glu Ile Ala Arg Arg His
    50                  55                  60

Pro Phe Leu Tyr Ala Pro Thr Ile Leu Leu Trp Ala Ala Arg Tyr Asp
65                  70                  75                  80

Lys Ile Ile Pro Ser Cys Cys Lys Ala Glu Asn Ala Val Glu Cys Phe
                85                  90                  95

Gln Thr Lys Ala Ala Thr Val Thr Lys Glu Leu Arg Glu Ser Ser Leu
            100                 105                 110

Leu Asn Gln His Ala Cys Ala Val Met Lys Asn Phe Gly Thr Arg Thr
        115                 120                 125

Phe Gln Ala Ile Thr Val Thr Lys Leu Ser Gln Lys Phe Thr Lys Val
    130                 135                 140

Asn Phe Thr Glu Ile Gln Lys Leu Val Leu Asp Val Ala His Val His
145                 150                 155                 160

Glu His Cys Cys Arg Gly Asp Val Leu Asp Cys Leu Gln Asp Gly Glu
                165                 170                 175

Lys Ile Met Ser Tyr Ile Cys Ser Gln Gln Asp Thr Leu Ser Asn Lys
            180                 185                 190

Ile Thr Glu Cys Cys Lys Leu Thr Thr Leu Glu Arg Gly Gln Cys Ile
        195                 200                 205

Ile His Ala Glu Asn Asp Glu Lys Pro Glu Gly Leu Ser Pro Asn Leu
    210                 215                 220

Asn Arg Phe Leu Gly Asp Arg Asp Phe Asn Gln Phe Ser Ser Gly Glu
225                 230                 235                 240

Lys Asn Ile Phe Leu Ala Ser Phe Val His Glu Tyr Ser Arg Arg His
                245                 250                 255

Pro Gln Leu Ala Val Ser Val Ile Leu Arg Val Ala Lys Gly Tyr Gln
            260                 265                 270

Glu Leu Leu Glu Lys Cys Phe Gln Thr Glu Asn Pro Leu Glu Cys Gln
        275                 280                 285

Asp Lys Gly Glu Glu Glu Leu Gln Lys Tyr Ile Gln Glu Ser Gln Ala
    290                 295                 300

Leu Ala Lys Arg Ser Cys Gly Leu Phe Gln Lys Leu Gly Glu Tyr Tyr
305                 310                 315                 320

Leu Gln Asn Ala Phe Leu Val Ala Tyr Thr Lys Lys Ala Pro Gln Leu
                325                 330                 335

Thr Ser Ser Glu Leu Met Ala Ile Thr Arg Lys Met Ala Ala Thr Ala
            340                 345                 350

Ala Thr Cys Cys Gln Leu Ser Glu Asp Lys Leu Leu Ala Cys Gly Glu
        355                 360                 365

Gly Ala Ala Asp Ile Ile Ile Gly His Leu Cys Ile Arg His Glu Met
    370                 375                 380

Thr Pro Val Asn Pro Gly Val Gly Gln Cys Cys Thr Ser Ser Tyr Ala
385                 390                 395                 400

Asn Arg Arg Pro Cys Phe Ser Ser Leu Val Val Asp Glu Thr Tyr Val
                405                 410                 415

Pro Pro Ala Phe Ser Asp Asp Lys Phe Ile Phe His Lys Asp Leu Cys
            420                 425                 430

Gln Ala Gln Gly Val Ala Leu Gln Thr Met Lys Gln Glu Phe Leu Ile
        435                 440                 445

Asn Leu Val Lys Gln Lys Pro Gln Ile Thr Glu Glu Gln Leu Glu Ala
    450                 455                 460

Val Ile Ala Asp Phe Ser Gly Leu Leu Glu Lys Cys Cys Gln Gly Gln
465                 470                 475                 480

Glu Gln Glu Val

<210> SEQ ID NO 16
<211> LENGTH: 503
<212> TYPE: PRT
<213> ORGANISM: Homo sapiens

<400> SEQUENCE: 16

Lys Tyr Gly His Ser Asp Cys Cys Ser Gln Ser Glu Glu Gly Arg His
1               5                   10                  15

Asn Cys Phe Leu Ala His Lys Lys Pro Thr Pro Ala Ser Ile Pro Leu
            20                  25                  30

Phe Gln Val Pro Glu Pro Val Thr Ser Cys Glu Ala Tyr Glu Glu Asp
        35                  40                  45

```
Arg Glu Thr Phe Met Asn Lys Phe Ile Tyr Glu Ile Ala Arg Arg His
    50                  55                  60

Pro Phe Leu Tyr Ala Pro Thr Ile Leu Leu Trp Ala Ala Arg Tyr Asp
65                  70                  75                  80

Lys Ile Ile Pro Ser Cys Cys Lys Ala Glu Asn Ala Val Glu Cys Phe
                85                  90                  95

Gln Thr Lys Ala Ala Thr Val Thr Lys Glu Leu Arg Glu Ser Ser Leu
                100                 105                 110

Leu Asn Gln His Ala Cys Ala Val Met Lys Asn Phe Gly Thr Arg Thr
            115                 120                 125

Phe Gln Ala Ile Thr Val Thr Lys Leu Ser Gln Lys Phe Thr Lys Val
        130                 135                 140

Asn Phe Thr Glu Ile Gln Lys Leu Val Leu Asp Val Ala His Val His
145                 150                 155                 160

Glu His Cys Cys Arg Gly Asp Val Leu Asp Cys Leu Gln Asp Gly Glu
                165                 170                 175

Lys Ile Met Ser Tyr Ile Cys Ser Gln Gln Asp Thr Leu Ser Asn Lys
                180                 185                 190

Ile Thr Glu Cys Cys Lys Leu Thr Thr Leu Glu Arg Gly Gln Cys Ile
            195                 200                 205

Ile His Ala Glu Asn Asp Glu Lys Pro Glu Gly Leu Ser Pro Asn Leu
        210                 215                 220

Asn Arg Phe Leu Gly Asp Arg Asp Phe Asn Gln Phe Ser Ser Gly Glu
225                 230                 235                 240

Lys Asn Ile Phe Leu Ala Ser Phe Val His Glu Tyr Ser Arg Arg His
                245                 250                 255

Pro Gln Leu Ala Val Ser Val Ile Leu Arg Val Ala Lys Gly Tyr Gln
                260                 265                 270

Glu Leu Leu Glu Lys Cys Phe Gln Thr Glu Asn Pro Leu Glu Cys Gln
            275                 280                 285

Asp Lys Gly Glu Glu Glu Leu Gln Lys Tyr Ile Gln Glu Ser Gln Ala
        290                 295                 300

Leu Ala Lys Arg Ser Cys Gly Leu Phe Gln Lys Leu Gly Glu Tyr Tyr
305                 310                 315                 320

Leu Gln Asn Ala Phe Leu Val Ala Tyr Thr Lys Lys Ala Pro Gln Leu
                325                 330                 335

Thr Ser Ser Glu Leu Met Ala Ile Thr Arg Lys Met Ala Ala Thr Ala
                340                 345                 350

Ala Thr Cys Cys Gln Leu Ser Glu Asp Lys Leu Leu Ala Cys Gly Glu
            355                 360                 365

Gly Ala Ala Asp Ile Ile Ile Gly His Leu Cys Ile Arg His Glu Met
        370                 375                 380

Thr Pro Val Asn Pro Gly Val Gly Gln Cys Cys Thr Ser Ser Tyr Ala
385                 390                 395                 400

Asn Arg Arg Pro Cys Phe Ser Ser Leu Val Val Asp Glu Thr Tyr Val
                405                 410                 415

Pro Pro Ala Phe Ser Asp Asp Lys Phe Ile Phe His Lys Asp Leu Cys
                420                 425                 430

Gln Ala Gln Gly Val Ala Leu Gln Thr Met Lys Gln Glu Phe Leu Ile
            435                 440                 445

Asn Leu Val Lys Gln Lys Pro Gln Ile Thr Glu Glu Gln Leu Glu Ala
        450                 455                 460

Val Ile Ala Asp Phe Ser Gly Leu Leu Glu Lys Cys Cys Gln Gly Gln
465                 470                 475                 480
```

```
Glu Gln Glu Val Cys Phe Ala Glu Gly Gln Lys Leu Ile Ser Lys
            485                 490                 495
Thr Arg Ala Ala Leu Gly Val
            500

<210> SEQ ID NO 17
<211> LENGTH: 250
<212> TYPE: PRT
<213> ORGANISM: Homo sapiens

<400> SEQUENCE: 17

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250

<210> SEQ ID NO 18
<211> LENGTH: 37
<212> TYPE: DNA
<213> ORGANISM: artificial sequence
<220> FEATURE:
<223> OTHER INFORMATION: primer

<400> SEQUENCE: 18
tctaaagaag cccctgggag cacagctcat caccatg                        37

<210> SEQ ID NO 19
<211> LENGTH: 36
<212> TYPE: DNA
<213> ORGANISM: artificial sequence
```

```
<220> FEATURE:
<223> OTHER INFORMATION: primer

<400> SEQUENCE: 19
gcccggggag cggggcttg ccggccgtcg cactca                               36

<210> SEQ ID NO 20
<211> LENGTH: 33
<212> TYPE: DNA
<213> ORGANISM: artificial sequence
<220> FEATURE:
<223> OTHER INFORMATION: primer

<400> SEQUENCE: 20
accatgagtg agaaaactg gatttgtgtg gca                                  33

<210> SEQ ID NO 21
<211> LENGTH: 30
<212> TYPE: DNA
<213> ORGANISM: artificial sequence
<220> FEATURE:
<223> OTHER INFORMATION: primer

<400> SEQUENCE: 21
ggagccggtg accagggttc cctggcccca                                     30

<210> SEQ ID NO 22
<211> LENGTH: 30
<212> TYPE: DNA
<213> ORGANISM: artificial sequence
<220> FEATURE:
<223> OTHER INFORMATION: primer

<400> SEQUENCE: 22
ctcaccatgg agtttgggct gagctgggtt                                     30

<210> SEQ ID NO 23
<211> LENGTH: 36
<212> TYPE: DNA
<213> ORGANISM: artificial sequence
<220> FEATURE:
<223> OTHER INFORMATION: primer

<400> SEQUENCE: 23
ggaggctgag gagacggtga ccagggttcc ctggcc                              36

<210> SEQ ID NO 24
<211> LENGTH: 35
<212> TYPE: DNA
<213> ORGANISM: artificial sequence
<220> FEATURE:
<223> OTHER INFORMATION: primer

<400> SEQUENCE: 24
ggctcgagat grcctgswcy cctctcytyc tswyc                               35

<210> SEQ ID NO 25
<211> LENGTH: 29
<212> TYPE: DNA
<213> ORGANISM: artificial sequence
<220> FEATURE:
<223> OTHER INFORMATION: primer

<400> SEQUENCE: 25
cccgtcgacg aagctccttc agaggaggg                                      29
```

```
<210> SEQ ID NO 26
<211> LENGTH: 11
<212> TYPE: PRT
<213> ORGANISM: artificial sequence
<220> FEATURE:
<223> OTHER INFORMATION: synthetic peptide

<400> SEQUENCE: 26

Ser Thr Asp Arg Ile Pro Ala Thr Asn Met Asp
1               5                   10

<210> SEQ ID NO 27
<211> LENGTH: 11
<212> TYPE: PRT
<213> ORGANISM: artificial sequence
<220> FEATURE:
<223> OTHER INFORMATION: synthetic peptide

<400> SEQUENCE: 27

Arg Ile Pro Ala Thr Asn Met Asp Ser Ser His
1               5                   10

<210> SEQ ID NO 28
<211> LENGTH: 11
<212> TYPE: PRT
<213> ORGANISM: artificial sequence
<220> FEATURE:
<223> OTHER INFORMATION: synthetic peptide

<400> SEQUENCE: 28

Ala Thr Asn Met Asp Ser Ser His Ser Ile Thr
1               5                   10

<210> SEQ ID NO 29
<211> LENGTH: 11
<212> TYPE: PRT
<213> ORGANISM: artificial sequence
<220> FEATURE:
<223> OTHER INFORMATION: synthetic peptide

<400> SEQUENCE: 29

Ala Val Glu Asp Arg Lys Pro Ser Gly Leu Asn
1               5                   10

<210> SEQ ID NO 30
<211> LENGTH: 33
<212> TYPE: DNA
<213> ORGANISM: artificial sequence
<220> FEATURE:
<223> OTHER INFORMATION: primer

<400> SEQUENCE: 30
atggcgcagg tgcagctgca ggagttgggt cca                           33

<210> SEQ ID NO 31
<211> LENGTH: 45
<212> TYPE: DNA
<213> ORGANISM: artificial sequence
<220> FEATURE:
<223> OTHER INFORMATION: primer

<400> SEQUENCE: 31
cgatgggccc ttggtggagg cgctagcgac agtgaccatt gtccc              45

<210> SEQ ID NO 32
<211> LENGTH: 54
<212> TYPE: DNA
<213> ORGANISM: artificial sequence
```

```
<220> FEATURE:
<223> OTHER INFORMATION: primer

<400> SEQUENCE: 32
cacaggcagc ccagaggctg ggagcagctc tacaacaccg tgtcatttaa cctt      54

<210> SEQ ID NO 33
<211> LENGTH: 54
<212> TYPE: DNA
<213> ORGANISM: artificial sequence
<220> FEATURE:
<223> OTHER INFORMATION: primer

<400> SEQUENCE: 33
cgttccatag acctgcagtc tagagtcgac tcactatttg agcttttaa actt      54

<210> SEQ ID NO 34
<211> LENGTH: 60
<212> TYPE: DNA
<213> ORGANISM: artificial sequence
<220> FEATURE:
<223> OTHER INFORMATION: primer

<400> SEQUENCE: 34
aagtttaaaa gctccaaata gtgatctaga gtcgacctgc aggtctatgg aacgataaat      60

<210> SEQ ID NO 35
<211> LENGTH: 45
<212> TYPE: DNA
<213> ORGANISM: artificial sequence
<220> FEATURE:
<223> OTHER INFORMATION: primer

<400> SEQUENCE: 35
cactgagggt ggctgagtca gctcatagtg atggtggtag tgagt      45

<210> SEQ ID NO 36
<211> LENGTH: 45
<212> TYPE: DNA
<213> ORGANISM: artificial sequence
<220> FEATURE:
<223> OTHER INFORMATION: primer

<400> SEQUENCE: 36
catcaccatc accatcacta tgagctgact cagccaccct cagtg      45

<210> SEQ ID NO 37
<211> LENGTH: 45
<212> TYPE: DNA
<213> ORGANISM: artificial sequence
<220> FEATURE:
<223> OTHER INFORMATION: primer

<400> SEQUENCE: 37
ctcgagtcac tatgaacatt ctgtaggggc cactgtcttc tccac      45

<210> SEQ ID NO 38
<211> LENGTH: 8
<212> TYPE: PRT
<213> ORGANISM: Homo sapiens

<400> SEQUENCE: 38

Asn Leu Gln Asn Val Asp Met Lys
1               5

<210> SEQ ID NO 39
```

```
<211> LENGTH: 8
<212> TYPE: PRT
<213> ORGANISM: Homo sapiens

<400> SEQUENCE: 39

Tyr Val Gln Lys Gly Glu Tyr Arg
1               5

<210> SEQ ID NO 40
<211> LENGTH: 11
<212> TYPE: PRT
<213> ORGANISM: Homo sapiens

<400> SEQUENCE: 40

Lys Pro Ser Gly Leu Asn Gly Glu Ala Ser Lys
1               5                   10

<210> SEQ ID NO 41
<211> LENGTH: 12
<212> TYPE: PRT
<213> ORGANISM: Homo sapiens

<400> SEQUENCE: 41

Tyr Gly Phe Ile Glu Gly His Val Val Ile Pro Arg
1               5                   10

<210> SEQ ID NO 42
<211> LENGTH: 8
<212> TYPE: PRT
<213> ORGANISM: Homo sapiens

<400> SEQUENCE: 42

Thr Glu Ala Ala Asp Leu Cys Lys
1               5

<210> SEQ ID NO 43
<211> LENGTH: 13
<212> TYPE: PRT
<213> ORGANISM: Homo sapiens

<400> SEQUENCE: 43

Leu Val Ile Asn Ser Gly Asn Gly Ala Val Glu Asp Arg
1               5                   10

<210> SEQ ID NO 44
<211> LENGTH: 16
<212> TYPE: PRT
<213> ORGANISM: Homo sapiens

<400> SEQUENCE: 44

Glu Ser Ser Glu Thr Pro Asp Gln Phe Met Thr Ala Asp Glu Thr Arg
1               5                   10                  15

<210> SEQ ID NO 45
<211> LENGTH: 26
<212> TYPE: PRT
<213> ORGANISM: Homo sapiens

<400> SEQUENCE: 45

Thr Gly Pro Leu Ser Met Thr Thr Gln Gln Ser Asn Ser Gln Ser Phe
1               5                   10                  15

Ser Thr Ser His Glu Gly Leu Glu Glu Asp
            20                  25

<210> SEQ ID NO 46
```

```
<211> LENGTH: 14
<212> TYPE: PRT
<213> ORGANISM: Homo sapiens

<400> SEQUENCE: 46

Tyr Gly His Ser Asp Cys Cys Ser Gln Ser Glu Glu Gly Arg
1               5                   10

<210> SEQ ID NO 47
<211> LENGTH: 8
<212> TYPE: PRT
<213> ORGANISM: Homo sapiens

<400> SEQUENCE: 47

His Asn Cys Phe Leu Ala His Lys
1               5

<210> SEQ ID NO 48
<211> LENGTH: 7
<212> TYPE: PRT
<213> ORGANISM: Homo sapiens

<400> SEQUENCE: 48

Phe Ile Tyr Glu Ile Ala Arg
1               5

<210> SEQ ID NO 49
<211> LENGTH: 15
<212> TYPE: PRT
<213> ORGANISM: Homo sapiens

<400> SEQUENCE: 49

His Pro Phe Leu Tyr Ala Pro Thr Ile Leu Leu Trp Ala Ala Arg
1               5                   10                  15

<210> SEQ ID NO 50
<211> LENGTH: 7
<212> TYPE: PRT
<213> ORGANISM: Homo sapiens

<400> SEQUENCE: 50

Ile Ile Pro Ser Cys Cys Lys
1               5

<210> SEQ ID NO 51
<211> LENGTH: 11
<212> TYPE: PRT
<213> ORGANISM: Homo sapiens

<400> SEQUENCE: 51

Ala Glu Asn Ala Val Glu Cys Phe Gln Thr Lys
1               5                   10

<210> SEQ ID NO 52
<211> LENGTH: 14
<212> TYPE: PRT
<213> ORGANISM: Homo sapiens

<400> SEQUENCE: 52

Glu Ser Ser Leu Leu Asn Gln His Ala Cys Ala Val Met Lys
1               5                   10

<210> SEQ ID NO 53
<211> LENGTH: 9
<212> TYPE: PRT
<213> ORGANISM: Homo sapiens
```

```
<400> SEQUENCE: 53

Thr Phe Gln Ala Ile Thr Val Thr Lys
1               5

<210> SEQ ID NO 54
<211> LENGTH: 7
<212> TYPE: PRT
<213> ORGANISM: Homo sapiens

<400> SEQUENCE: 54

Leu Ser Gln Lys Phe Thr Lys
1               5

<210> SEQ ID NO 55
<211> LENGTH: 14
<212> TYPE: PRT
<213> ORGANISM: Homo sapiens

<400> SEQUENCE: 55

Leu Val Leu Asp Val Ala His Val His Glu His Cys Cys Arg
1               5                   10

<210> SEQ ID NO 56
<211> LENGTH: 12
<212> TYPE: PRT
<213> ORGANISM: Homo sapiens

<400> SEQUENCE: 56

Gly Asp Val Leu Asp Cys Leu Gln Asp Gly Glu Lys
1               5                   10

<210> SEQ ID NO 57
<211> LENGTH: 15
<212> TYPE: PRT
<213> ORGANISM: Homo sapiens

<400> SEQUENCE: 57

Ile Met Ser Tyr Ile Cys Ser Gln Gln Asp Thr Leu Ser Asn Lys
1               5                   10                  15

<210> SEQ ID NO 58
<211> LENGTH: 22
<212> TYPE: PRT
<213> ORGANISM: Homo sapiens

<400> SEQUENCE: 58

Gly Gln Cys Ile Ile His Ala Glu Asn Asp Glu Lys Pro Glu Gly Leu
1               5                   10                  15

Ser Pro Asn Leu Asn Arg
            20

<210> SEQ ID NO 59
<211> LENGTH: 15
<212> TYPE: PRT
<213> ORGANISM: Homo sapiens

<400> SEQUENCE: 59

Phe Leu Gly Asp Arg Asp Phe Asn Gln Phe Ser Ser Gly Glu Lys
1               5                   10                  15

<210> SEQ ID NO 60
<211> LENGTH: 10
<212> TYPE: PRT
<213> ORGANISM: Homo sapiens
```

```
<400> SEQUENCE: 60

Asp Phe Asn Gln Phe Ser Ser Gly Glu Lys
1               5                   10

<210> SEQ ID NO 61
<211> LENGTH: 23
<212> TYPE: PRT
<213> ORGANISM: Homo sapiens

<400> SEQUENCE: 61

Asp Phe Asn Gln Phe Ser Ser Gly Glu Lys Asn Ile Phe Leu Ala Ser
1               5                   10                  15

Phe Val His Glu Tyr Ser Arg
            20

<210> SEQ ID NO 62
<211> LENGTH: 13
<212> TYPE: PRT
<213> ORGANISM: Homo sapiens

<400> SEQUENCE: 62

Asn Ile Phe Leu Ala Ser Phe Val His Glu Tyr Ser Arg
1               5                   10

<210> SEQ ID NO 63
<211> LENGTH: 12
<212> TYPE: PRT
<213> ORGANISM: Homo sapiens

<400> SEQUENCE: 63

Arg His Pro Gln Leu Ala Val Ser Val Ile Leu Arg
1               5                   10

<210> SEQ ID NO 64
<211> LENGTH: 11
<212> TYPE: PRT
<213> ORGANISM: Homo sapiens

<400> SEQUENCE: 64

His Pro Gln Leu Ala Val Ser Val Ile Leu Arg
1               5                   10

<210> SEQ ID NO 65
<211> LENGTH: 8
<212> TYPE: PRT
<213> ORGANISM: Homo sapiens

<400> SEQUENCE: 65

Gly Tyr Gln Glu Leu Leu Glu Lys
1               5

<210> SEQ ID NO 66
<211> LENGTH: 11
<212> TYPE: PRT
<213> ORGANISM: Homo sapiens

<400> SEQUENCE: 66

Tyr Ile Gln Glu Ser Gln Ala Leu Ala Lys Arg
1               5                   10

<210> SEQ ID NO 67
<211> LENGTH: 8
<212> TYPE: PRT
```

```
<400> SEQUENCE: 67

Arg Ser Cys Gly Leu Phe Gln Lys
1               5

<210> SEQ ID NO 68
<211> LENGTH: 17
<212> TYPE: PRT
<213> ORGANISM: Homo sapiens

<400> SEQUENCE: 68

Leu Gly Glu Tyr Tyr Leu Gln Asn Ala Phe Leu Val Ala Tyr Thr Lys
1               5                   10                  15

Lys

<210> SEQ ID NO 69
<211> LENGTH: 15
<212> TYPE: PRT
<213> ORGANISM: Homo sapiens

<400> SEQUENCE: 69

Lys Ala Pro Gln Leu Thr Ser Ser Glu Leu Met Ala Ile Thr Arg
1               5                   10                  15

<210> SEQ ID NO 70
<211> LENGTH: 14
<212> TYPE: PRT
<213> ORGANISM: Homo sapiens

<400> SEQUENCE: 70

Ala Pro Gln Leu Thr Ser Ser Glu Leu Met Ala Ile Thr Arg
1               5                   10

<210> SEQ ID NO 71
<211> LENGTH: 34
<212> TYPE: PRT
<213> ORGANISM: Homo sapiens

<400> SEQUENCE: 71

Met Ala Ala Thr Ala Ala Thr Cys Cys Gln Leu Ser Glu Asp Lys Leu
1               5                   10                  15

Leu Ala Cys Gly Glu Gly Ala Ala Asp Ile Ile Ile Gly His Leu Cys
            20                  25                  30

Ile Arg

<210> SEQ ID NO 72
<211> LENGTH: 19
<212> TYPE: PRT
<213> ORGANISM: Homo sapiens

<400> SEQUENCE: 72

Leu Leu Ala Cys Gly Glu Gly Ala Ala Asp Ile Ile Ile Gly His Leu
1               5                   10                  15

Cys Ile Arg

<210> SEQ ID NO 73
<211> LENGTH: 23
<212> TYPE: PRT
<213> ORGANISM: Homo sapiens

<400> SEQUENCE: 73

Asp Leu Cys Gln Ala Gln Gly Val Ala Leu Gln Thr Met Lys Gln Glu
1               5                   10                  15
```

```
Phe Leu Ile Asn Leu Val Lys
            20

<210> SEQ ID NO 74
<211> LENGTH: 9
<212> TYPE: PRT
<213> ORGANISM: Homo sapiens

<400> SEQUENCE: 74

Gln Glu Phe Leu Ile Asn Leu Val Lys
1               5

<210> SEQ ID NO 75
<211> LENGTH: 23
<212> TYPE: PRT
<213> ORGANISM: Homo sapiens

<400> SEQUENCE: 75

Gln Lys Pro Gln Ile Thr Glu Glu Gln Leu Glu Ala Val Ile Ala Asp
1               5                   10                  15

Phe Ser Gly Leu Leu Glu Lys
            20

<210> SEQ ID NO 76
<211> LENGTH: 609
<212> TYPE: PRT
<213> ORGANISM: Homo sapiens

<400> SEQUENCE: 76

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
```

```
                225                 230                 235                 240
Thr Lys Leu Ser Gln Lys Phe Thr Lys Val Asn Phe Thr Glu Ile Gln
            245                 250                 255
Lys Leu Val Leu Asp Val Ala His Val His Glu His Cys Cys Arg Gly
        260                 265                 270
Asp Val Leu Asp Cys Leu Gln Asp Gly Glu Lys Ile Met Ser Tyr Ile
    275                 280                 285
Cys Ser Gln Gln Asp Thr Leu Ser Asn Lys Ile Thr Glu Cys Cys Lys
290                 295                 300
Leu Thr Thr Leu Glu Arg Gly Gln Cys Ile Ile His Ala Glu Asn Asp
305                 310                 315                 320
Glu Lys Pro Glu Gly Leu Ser Pro Asn Leu Asn Arg Phe Leu Gly Asp
                325                 330                 335
Arg Asp Phe Asn Gln Phe Ser Ser Gly Glu Lys Asn Ile Phe Leu Ala
            340                 345                 350
Ser Phe Val His Glu Tyr Ser Arg Arg His Pro Gln Leu Ala Val Ser
        355                 360                 365
Val Ile Leu Arg Val Ala Lys Gly Tyr Gln Glu Leu Leu Glu Lys Cys
    370                 375                 380
Phe Gln Thr Glu Asn Pro Leu Glu Cys Gln Asp Lys Gly Glu Glu Glu
385                 390                 395                 400
Leu Gln Lys Tyr Ile Gln Glu Ser Gln Ala Leu Ala Lys Arg Ser Cys
                405                 410                 415
Gly Leu Phe Gln Lys Leu Gly Glu Tyr Tyr Leu Gln Asn Ala Phe Leu
            420                 425                 430
Val Ala Tyr Thr Lys Lys Ala Pro Gln Leu Thr Ser Ser Glu Leu Met
        435                 440                 445
Ala Ile Thr Arg Lys Met Ala Ala Thr Ala Ala Thr Cys Cys Gln Leu
    450                 455                 460
Ser Glu Asp Lys Leu Leu Ala Cys Gly Glu Gly Ala Ala Asp Ile Ile
465                 470                 475                 480
Ile Gly His Leu Cys Ile Arg His Glu Met Thr Pro Val Asn Pro Gly
                485                 490                 495
Val Gly Gln Cys Cys Thr Ser Ser Tyr Ala Asn Arg Arg Pro Cys Phe
            500                 505                 510
Ser Ser Leu Val Val Asp Glu Thr Tyr Val Pro Pro Ala Phe Ser Asp
        515                 520                 525
Asp Lys Phe Ile Phe His Lys Asp Leu Cys Gln Ala Gln Gly Val Ala
    530                 535                 540
Leu Gln Thr Met Lys Gln Glu Phe Leu Ile Asn Leu Val Lys Gln Lys
545                 550                 555                 560
Pro Gln Ile Thr Glu Glu Gln Leu Glu Ala Val Ile Ala Asp Phe Ser
                565                 570                 575
Gly Leu Leu Glu Lys Cys Cys Gln Gly Gln Glu Gln Glu Val Cys Phe
            580                 585                 590
Ala Glu Glu Gly Gln Lys Leu Ile Ser Lys Thr Arg Ala Ala Leu Gly
        595                 600                 605
Val

<210> SEQ ID NO 77
<211> LENGTH: 609
<212> TYPE: PRT
<213> ORGANISM: Homo sapiens

<400> SEQUENCE: 77
```

```
Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
```

```
                   420             425             430
Val Ala Tyr Thr Lys Lys Ala Pro Gln Leu Thr Ser Ser Glu Leu Met
            435                 440                 445

Ala Ile Thr Arg Lys Met Ala Ala Thr Ala Ala Thr Cys Cys Gln Leu
    450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
    515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
    595                 600                 605

Val

<210> SEQ ID NO 78
<211> LENGTH: 493
<212> TYPE: PRT
<213> ORGANISM: Homo sapiens

<400> SEQUENCE: 78

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190
```

```
Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Asn Met
    210                 215                 220

Asp Ser Ser His Ser Ile Thr Leu Gln Pro Thr Ala Asn Pro Asn Thr
225                 230                 235                 240

Gly Leu Val Glu Asp Leu Asp Arg Thr Gly Pro Leu Ser Met Thr Thr
                245                 250                 255

Gln Gln Ser Asn Ser Gln Ser Phe Ser Thr Ser His Glu Gly Leu Glu
                260                 265                 270

Glu Asp Lys Asp His Pro Thr Thr Ser Thr Leu Thr Ser Ser Asn Arg
            275                 280                 285

Asn Asp Val Thr Gly Gly Arg Arg Asp Pro Asn His Ser Glu Gly Ser
            290                 295                 300

Thr Thr Leu Leu Glu Gly Tyr Thr Ser His Tyr Pro His Thr Lys Glu
305                 310                 315                 320

Ser Arg Thr Phe Ile Pro Val Thr Ser Ala Lys Thr Gly Ser Phe Gly
                325                 330                 335

Val Thr Ala Val Thr Val Gly Asp Ser Asn Ser Asn Val Asn Arg Ser
            340                 345                 350

Leu Ser Gly Asp Gln Asp Thr Phe His Pro Ser Gly Gly Ser His Thr
            355                 360                 365

Thr His Gly Ser Glu Ser Asp Gly His Ser His Gly Ser Gln Glu Gly
            370                 375                 380

Gly Ala Asn Thr Thr Ser Gly Pro Ile Arg Thr Pro Gln Ile Pro Glu
385                 390                 395                 400

Trp Leu Ile Ile Leu Ala Ser Leu Leu Ala Leu Ala Leu Ile Leu Ala
                405                 410                 415

Val Cys Ile Ala Val Asn Ser Arg Arg Arg Cys Gly Gln Lys Lys Lys
            420                 425                 430

Leu Val Ile Asn Ser Gly Asn Gly Ala Val Glu Asp Arg Lys Pro Ser
            435                 440                 445

Gly Leu Asn Gly Glu Ala Ser Lys Ser Gln Glu Met Val His Leu Val
    450                 455                 460

Asn Lys Glu Ser Ser Glu Thr Pro Asp Gln Phe Met Thr Ala Asp Glu
465                 470                 475                 480

Thr Arg Asn Leu Gln Asn Val Asp Met Lys Ile Gly Val
                485                 490

<210> SEQ ID NO 79
<211> LENGTH: 493
<212> TYPE: PRT
<213> ORGANISM: Homo sapiens

<400> SEQUENCE: 79

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
                20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80
```

```
Phe Ile Glu Gly His Val Val Ile Pro Arg Ile His Pro Asn Ser Ile
                85                  90                  95
Cys Ala Ala Asn Asn Thr Gly Val Tyr Ile Leu Thr Ser Asn Thr Ser
            100                 105                 110
Gln Tyr Asp Thr Tyr Cys Phe Asn Ala Ser Ala Pro Pro Glu Glu Asp
            115                 120                 125
Cys Thr Ser Val Thr Asp Leu Pro Asn Ala Phe Asp Gly Pro Ile Thr
130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Ser Glu Arg Ser Ser Thr Ser Gly Gly
            180                 185                 190
Tyr Ile Phe Tyr Thr Phe Ser Thr Val His Pro Ile Pro Asp Glu Asp
            195                 200                 205
Ser Pro Trp Ile Thr Asp Ser Thr Asp Arg Ile Pro Ala Thr Asn Met
            210                 215                 220
Asp Ser Ser His Ser Ile Thr Leu Gln Pro Thr Ala Asn Pro Asn Thr
225                 230                 235                 240
Gly Leu Val Glu Asp Leu Asp Arg Thr Gly Pro Leu Ser Met Thr Thr
                245                 250                 255
Gln Gln Ser Asn Ser Gln Ser Phe Ser Thr Ser His Glu Gly Leu Glu
            260                 265                 270
Glu Asp Lys Asp His Pro Thr Thr Ser Thr Leu Thr Ser Ser Asn Arg
            275                 280                 285
Asn Asp Val Thr Gly Gly Arg Arg Asp Pro Asn His Ser Glu Gly Ser
            290                 295                 300
Thr Thr Leu Leu Glu Gly Tyr Thr Ser His Tyr Pro His Thr Lys Glu
305                 310                 315                 320
Ser Arg Thr Phe Ile Pro Val Thr Ser Ala Lys Thr Gly Ser Phe Gly
                325                 330                 335
Val Thr Ala Val Thr Val Gly Asp Ser Asn Ser Asn Val Asn Arg Ser
            340                 345                 350
Leu Ser Gly Asp Gln Asp Thr Phe His Pro Ser Gly Gly Ser His Thr
            355                 360                 365
Thr His Gly Ser Glu Ser Asp Gly His Ser His Gly Ser Gln Glu Gly
            370                 375                 380
Gly Ala Asn Thr Thr Ser Gly Pro Ile Arg Thr Pro Gln Ile Pro Glu
385                 390                 395                 400
Trp Leu Ile Ile Leu Ala Ser Leu Leu Ala Leu Ala Leu Ile Leu Ala
                405                 410                 415
Val Cys Ile Ala Val Asn Ser Arg Arg Arg Cys Gly Gln Lys Lys Lys
            420                 425                 430
Leu Val Ile Asn Ser Gly Asn Gly Ala Val Glu Asp Arg Lys Pro Ser
            435                 440                 445
Gly Leu Asn Gly Glu Ala Ser Lys Ser Gln Glu Met Val His Leu Val
            450                 455                 460
Asn Lys Glu Ser Ser Glu Thr Pro Asp Gln Phe Met Thr Ala Asp Glu
465                 470                 475                 480
Thr Arg Asn Leu Gln Asn Val Asp Met Lys Ile Gly Val
                485                 490
```

-continued

```
<210> SEQ ID NO 80
<211> LENGTH: 17
<212> TYPE: PRT
<213> ORGANISM: Homo sapiens

<400> SEQUENCE: 80

Ser Thr Asp Arg Ile Pro Ala Thr Asn Met Asp Ser Ser His Ser Ile
1               5                   10                  15

Thr

<210> SEQ ID NO 81
<211> LENGTH: 2401
<212> TYPE: DNA
<213> ORGANISM: Artificial Sequence
<220> FEATURE:
<223> OTHER INFORMATION: Immunoconjugate
<220> FEATURE:
<221> NAME/KEY: CDS
<222> LOCATION: (66)..(1595)
<220> FEATURE:
<221> NAME/KEY: CDS
<222> LOCATION: (1673)..(2395)

<400> SEQUENCE: 81
gaattcctgc aggtctatgg aacgataaat gcccatgaaa attctatttc aaggagacag      60 tcata atg aaa tac cta ttg cct acg gca gcc gct gga ttg tta tta ctc     110
      Met Lys Tyr Leu Leu Pro Thr Ala Ala Ala Gly Leu Leu Leu Leu
      1               5                   10                  15 gct gcc caa cca gcg atg gcg cag gtg cag ctg cag gag ttg ggt cca       158
Ala Ala Gln Pro Ala Met Ala Gln Val Gln Leu Gln Glu Leu Gly Pro
                20                  25                  30 agg ctg gtg agg cct tca cag acc ctg atc ctc acc tgc act gtc tct       206
Arg Leu Val Arg Pro Ser Gln Thr Leu Ile Leu Thr Cys Thr Val Ser
        35                  40                  45 gga ggc tcc gtc agc ggc gat gag tat tac tgg agt tgg ctc cgt cag       254
Gly Gly Ser Val Ser Gly Asp Glu Tyr Tyr Trp Ser Trp Leu Arg Gln
    50                  55                  60 acc cca ggg aag ggc ctg gag tgg att ggg tac atg tct tac aga ggg       302
Thr Pro Gly Lys Gly Leu Glu Trp Ile Gly Tyr Met Ser Tyr Arg Gly
65                  70                  75 agc agt tat tac agt ccg tcc ctc cag agt cga gtt acc att gca gtg       350
Ser Ser Tyr Tyr Ser Pro Ser Leu Gln Ser Arg Val Thr Ile Ala Val
80                  85                  90                  95 gac agg tcc aag aac gaa ttt tcc ctg aag ctg acg tct gtg act gcc       398
Asp Arg Ser Lys Asn Glu Phe Ser Leu Lys Leu Thr Ser Val Thr Ala
                100                 105                 110 gca gac gcg gcc gta tat ttc tgt gcc aga aaa tat tgt ggt ggc gat       446
Ala Asp Ala Ala Val Tyr Phe Cys Ala Arg Lys Tyr Cys Gly Gly Asp
            115                 120                 125 tgc agg agt ggt ttt gat atc tgg ggc cga ggg aca atg gtc act gtc       494
Cys Arg Ser Gly Phe Asp Ile Trp Gly Arg Gly Thr Met Val Thr Val
        130                 135                 140 gcc agc gct agc acc aag ggc cca tcg gtc ttc ccc ctg gca ccc tcc       542
Ala Ser Ala Ser Thr Lys Gly Pro Ser Val Phe Pro Leu Ala Pro Ser
    145                 150                 155 tcc aag agc acc tct ggg ggc aca gcg gcc ctg ggc tgc ctg gtc aag       590
Ser Lys Ser Thr Ser Gly Gly Thr Ala Ala Leu Gly Cys Leu Val Lys
160                 165                 170                 175 gac tac ttc ccc gaa ccg gtg acg gtg tcg tgg aac tca ggc gcc ctg       638
Asp Tyr Phe Pro Glu Pro Val Thr Val Ser Trp Asn Ser Gly Ala Leu
                180                 185                 190 acc agc ggc gtg cac acc ttc ccg gct gtc cta cag tcc tca gga ctc       686
Thr Ser Gly Val His Thr Phe Pro Ala Val Leu Gln Ser Ser Gly Leu
```

-continued

```
                195                      200                      205
tac tcc ctc agc agc gtg gtg acc gtg ccc tcc agc agc ttg ggc acc        734
Tyr Ser Leu Ser Ser Val Val Thr Val Pro Ser Ser Ser Leu Gly Thr
            210                      215                      220 cag acc tac atc tgc aac gtg aat cac aag ccc agc aac acc aag gtg        782
Gln Thr Tyr Ile Cys Asn Val Asn His Lys Pro Ser Asn Thr Lys Val
    225                      230                      235 gac aag aaa gtt gag ccc aaa tct tgt acc agg cac agg cag ccc aga        830
Asp Lys Lys Val Glu Pro Lys Ser Cys Thr Arg His Arg Gln Pro Arg
240                      245                      250                      255 ggc tgg gag cag ctc tac aac acc gtg tca ttt aac ctt gga gaa gct        878
Gly Trp Glu Gln Leu Tyr Asn Thr Val Ser Phe Asn Leu Gly Glu Ala
                260                      265                      270 tat gag tac ccc act ttt ata caa gat ttg cgc aat gaa ttg gct aag        926
Tyr Glu Tyr Pro Thr Phe Ile Gln Asp Leu Arg Asn Glu Leu Ala Lys
            275                      280                      285 ggc aca cca gta tgt caa ctt cca gta aca cta caa acc ata gcc gat        974
Gly Thr Pro Val Cys Gln Leu Pro Val Thr Leu Gln Thr Ile Ala Asp
    290                      295                      300 gac aag cga ttt gtt cta gtt gat atc act acg acc tcg aag aaa aca       1022
Asp Lys Arg Phe Val Leu Val Asp Ile Thr Thr Thr Ser Lys Lys Thr
305                      310                      315 gtt aag gtt gct ata gat gtg aca gat gtg tat gtt gtg ggt tat caa       1070
Val Lys Val Ala Ile Asp Val Thr Asp Val Tyr Val Val Gly Tyr Gln
320                      325                      330                      335 gac aaa tgg gat ggc aaa gat cga gct gtt ttc ctt gac aag gtt cct       1118
Asp Lys Trp Asp Gly Lys Asp Arg Ala Val Phe Leu Asp Lys Val Pro
                340                      345                      350 act gtt gca act agt aaa ctt ttc cca ggg gtg act aat cgt gta acg       1166
Thr Val Ala Thr Ser Lys Leu Phe Pro Gly Val Thr Asn Arg Val Thr
            355                      360                      365 tta aca ttt gat ggc agc tat cag aaa ctt gtg aat gct gcc aaa gct       1214
Leu Thr Phe Asp Gly Ser Tyr Gln Lys Leu Val Asn Ala Ala Lys Ala
    370                      375                      380 gat aga aag gct ctc gaa ctg ggg gtt aac aaa ttg gaa ttt tcc att       1262
Asp Arg Lys Ala Leu Glu Leu Gly Val Asn Lys Leu Glu Phe Ser Ile
385                      390                      395 gaa gca atc cat ggt aaa acg ata aat ggt caa gag gca gcc aag ttc       1310
Glu Ala Ile His Gly Lys Thr Ile Asn Gly Gln Glu Ala Ala Lys Phe
400                      405                      410                      415 ttt ctt att gtc atc caa atg gtt tca gag gca gct cgg ttc aaa tat       1358
Phe Leu Ile Val Ile Gln Met Val Ser Glu Ala Ala Arg Phe Lys Tyr
                420                      425                      430 att gag act gag gtg gtt gat aga gga tta tat gga tca ttc aaa cct       1406
Ile Glu Thr Glu Val Val Asp Arg Gly Leu Tyr Gly Ser Phe Lys Pro
            435                      440                      445 aat ttt aaa gta ttg aac ttg gag aac aat tgg ggc gac atc tct gat       1454
Asn Phe Lys Val Leu Asn Leu Glu Asn Asn Trp Gly Asp Ile Ser Asp
    450                      455                      460 gcc att cac aaa tca tcc cca caa tgt acc act att aat ccg gca ctt       1502
Ala Ile His Lys Ser Ser Pro Gln Cys Thr Thr Ile Asn Pro Ala Leu
465                      470                      475 cag ttg ata agc ccc tca aat gac cca tgg gtt gta aat aaa gtg agt       1550
Gln Leu Ile Ser Pro Ser Asn Asp Pro Trp Val Val Asn Lys Val Ser
480                      485                      490                      495 caa att agt ccc gat atg ggt atc ctt aag ttt aaa agc tcc aaa           1595
Gln Ile Ser Pro Asp Met Gly Ile Leu Lys Phe Lys Ser Ser Lys
                500                      505                      510 tagtgatcta gagtcgacct gcaggtctat ggaacgataa atgcccatga aaattctatt    1655
```

| | | | | | | | | | | |
|---|---|---|---|---|---|---|---|---|---|---|
| tcaaggagac | agtcata | atg | aaa | tac | cta | ttg | cct | acg | gca gcc gct gga | 1705 |
| | | Met | Lys | Tyr | Leu | Leu | Pro | Thr | Ala Ala Ala Gly | |
| | | | 515 | | | | | | 520 | |

```
ttg tta tta ctc gcg gcc caa ccg gcc atg gcg cac cat cat cac cat    1753
Leu Leu Leu Leu Ala Ala Gln Pro Ala Met Ala His His His His His
            525                 530                 535 cac tat gag ctg act cag cca ccc tca gtg tcc gtg tcc cca gga cag    1801
His Tyr Glu Leu Thr Gln Pro Pro Ser Val Ser Val Ser Pro Gly Gln
            540                 545                 550 aaa gcc ttc ata acc tgc tct gga gat aac ctg ggg aat aaa tat gtg    1849
Lys Ala Phe Ile Thr Cys Ser Gly Asp Asn Leu Gly Asn Lys Tyr Val
            555                 560                 565 tgc tgg tat caa cag aag cca ggc cag tcc cct gtc ctg gtc atc tat    1897
Cys Trp Tyr Gln Gln Lys Pro Gly Gln Ser Pro Val Leu Val Ile Tyr
570                 575                 580                 585 gaa gat acc aag agg ccc tca ggg atc cct gag cga ttc tct gcc tcc    1945
Glu Asp Thr Lys Arg Pro Ser Gly Ile Pro Glu Arg Phe Ser Ala Ser
                    590                 595                 600 aac tct ggg aat aca gcc act ctg acc atc agc ggg acg cag cct ata    1993
Asn Ser Gly Asn Thr Ala Thr Leu Thr Ile Ser Gly Thr Gln Pro Ile
                605                 610                 615 gat gag gct gac tac tac tgt cag gcg tgg gac agc cgc act gaa atc    2041
Asp Glu Ala Asp Tyr Tyr Cys Gln Ala Trp Asp Ser Arg Thr Glu Ile
            620                 625                 630 ttc gga act ggg acc aag gtc acc gtc cta agt cag ccc aag gcc aac    2089
Phe Gly Thr Gly Thr Lys Val Thr Val Leu Ser Gln Pro Lys Ala Asn
            635                 640                 645 ccc act gtc act ctg ttc ccg ccc tcc tct gag gag ctc caa gcc aac    2137
Pro Thr Val Thr Leu Phe Pro Pro Ser Ser Glu Glu Leu Gln Ala Asn
650                 655                 660                 665 aag gcc aca cta gtg tgt ctg atc agt gac ttc tac ccg gga gct gtg    2185
Lys Ala Thr Leu Val Cys Leu Ile Ser Asp Phe Tyr Pro Gly Ala Val
                    670                 675                 680 aca gtg gcc tgg aag gca gat ggc agc ccc gtc aag gcg gga gtg gag    2233
Thr Val Ala Trp Lys Ala Asp Gly Ser Pro Val Lys Ala Gly Val Glu
                685                 690                 695 acc acc aaa ccc tcc aaa cag agc aac aac aag tac gcg gcc agc agc    2281
Thr Thr Lys Pro Ser Lys Gln Ser Asn Asn Lys Tyr Ala Ala Ser Ser
            700                 705                 710 tac ctg agc ctg acg ccc gag cag tgg aag tcc cac aga agc tac agc    2329
Tyr Leu Ser Leu Thr Pro Glu Gln Trp Lys Ser His Arg Ser Tyr Ser
            715                 720                 725 tgc cag gtc acg cat gaa ggg agc acc gtg gag aag aca gtg gcc cct    2377
Cys Gln Val Thr His Glu Gly Ser Thr Val Glu Lys Thr Val Ala Pro
730                 735                 740                 745 aca gaa tgt tca tag tga ctcgag                                     2401
Thr Glu Cys Ser <210> SEQ ID NO 82
<211> LENGTH: 510
<212> TYPE: PRT
<213> ORGANISM: Artificial Sequence
<220> FEATURE:
<223> OTHER INFORMATION: Immunoconjugate

<400> SEQUENCE: 82

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Leu Gly Pro Arg
            20                  25                  30

Leu Val Arg Pro Ser Gln Thr Leu Ile Leu Thr Cys Thr Val Ser Gly
```

```
            35                  40                  45
Gly Ser Val Ser Gly Asp Glu Tyr Tyr Trp Ser Trp Leu Arg Gln Thr
 50                  55                  60
Pro Gly Lys Gly Leu Glu Trp Ile Gly Tyr Met Ser Tyr Arg Gly Ser
 65                  70                  75                  80
Ser Tyr Tyr Ser Pro Ser Leu Gln Ser Arg Val Thr Ile Ala Val Asp
                     85                  90                  95
Arg Ser Lys Asn Glu Phe Ser Leu Lys Leu Thr Ser Val Thr Ala Ala
                100                 105                 110
Asp Ala Ala Val Tyr Phe Cys Ala Arg Lys Tyr Cys Gly Gly Asp Cys
                115                 120                 125
Arg Ser Gly Phe Asp Ile Trp Gly Arg Gly Thr Met Val Thr Val Ala
                130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
                180                 185                 190
Ser Gly Val His Thr Phe Pro Ala Val Leu Gln Ser Ser Gly Leu Tyr
                195                 200                 205
Ser Leu Ser Ser Val Val Thr Val Pro Ser Ser Ser Leu Gly Thr Gln
                210                 215                 220
Thr Tyr Ile Cys Asn Val Asn His Lys Pro Ser Asn Thr Lys Val Asp
225                 230                 235                 240
Lys Lys Val Glu Pro Lys Ser Cys Thr Arg His Arg Gln Pro Arg Gly
                245                 250                 255
Trp Glu Gln Leu Tyr Asn Thr Val Ser Phe Asn Leu Gly Glu Ala Tyr
                260                 265                 270
Glu Tyr Pro Thr Phe Ile Gln Asp Leu Arg Asn Glu Leu Ala Lys Gly
                275                 280                 285
Thr Pro Val Cys Gln Leu Pro Val Thr Leu Gln Thr Ile Ala Asp Asp
                290                 295                 300
Lys Arg Phe Val Leu Val Asp Ile Thr Thr Thr Ser Lys Lys Thr Val
305                 310                 315                 320
Lys Val Ala Ile Asp Val Thr Asp Val Tyr Val Val Gly Tyr Gln Asp
                325                 330                 335
Lys Trp Asp Gly Lys Asp Arg Ala Val Phe Leu Asp Lys Val Pro Thr
                340                 345                 350
Val Ala Thr Ser Lys Leu Phe Pro Gly Val Thr Asn Arg Val Thr Leu
                355                 360                 365
Thr Phe Asp Gly Ser Tyr Gln Lys Leu Val Asn Ala Ala Lys Ala Asp
                370                 375                 380
Arg Lys Ala Leu Glu Leu Gly Val Asn Lys Leu Glu Phe Ser Ile Glu
385                 390                 395                 400
Ala Ile His Gly Lys Thr Ile Asn Gly Gln Glu Ala Ala Lys Phe Phe
                405                 410                 415
Leu Ile Val Ile Gln Met Val Ser Glu Ala Ala Arg Phe Lys Tyr Ile
                420                 425                 430
Glu Thr Glu Val Val Asp Arg Gly Leu Tyr Gly Ser Phe Lys Pro Asn
                435                 440                 445
Phe Lys Val Leu Asn Leu Glu Asn Asn Trp Gly Asp Ile Ser Asp Ala
450                 455                 460
```

```
Ile His Lys Ser Ser Pro Gln Cys Thr Thr Ile Asn Pro Ala Leu Gln
465                 470                 475                 480

Leu Ile Ser Pro Ser Asn Asp Pro Trp Val Asn Lys Val Ser Gln
                485                 490                 495

Ile Ser Pro Asp Met Gly Ile Leu Lys Phe Lys Ser Ser Lys
            500                 505                 510

<210> SEQ ID NO 83
<211> LENGTH: 239
<212> TYPE: PRT
<213> ORGANISM: Artificial Sequence
<220> FEATURE:
<223> OTHER INFORMATION: Immunoconjugate

<400> SEQUENCE: 83

Met Lys Tyr Leu Leu Pro Thr Ala Ala Ala Gly Leu Leu Leu Leu Ala
1               5                   10                  15

Ala Gln Pro Ala Met Ala His His His His His Tyr Glu Leu Thr
                20                  25                  30

Gln Pro Pro Ser Val Ser Val Ser Pro Gly Gln Lys Ala Phe Ile Thr
            35                  40                  45

Cys Ser Gly Asp Asn Leu Gly Asn Lys Tyr Val Cys Trp Tyr Gln Gln
50                  55                  60

Lys Pro Gly Gln Ser Pro Val Leu Val Ile Tyr Glu Asp Thr Lys Arg
65                  70                  75                  80

Pro Ser Gly Ile Pro Glu Arg Phe Ser Ala Ser Asn Ser Gly Asn Thr
                85                  90                  95

Ala Thr Leu Thr Ile Ser Gly Thr Gln Pro Ile Asp Glu Ala Asp Tyr
            100                 105                 110

Tyr Cys Gln Ala Trp Asp Ser Arg Thr Glu Ile Phe Gly Thr Gly Thr
        115                 120                 125

Lys Val Thr Val Leu Ser Gln Pro Lys Ala Asn Pro Thr Val Thr Leu
130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Gly Ser Pro Val Lys Ala Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Gln Val Thr His
210                 215                 220

Glu Gly Ser Thr Val Glu Lys Thr Val Ala Pro Thr Glu Cys Ser
225                 230                 235

<210> SEQ ID NO 84
<211> LENGTH: 1601
<212> TYPE: DNA
<213> ORGANISM: Artificial Sequence
<220> FEATURE:
<223> OTHER INFORMATION: Immunoconjugate
<220> FEATURE:
<221> NAME/KEY: CDS
<222> LOCATION: (66)..(1595)

<400> SEQUENCE: 84
gaattcctgc aggtctatgg aacgataaat gcccatgaaa attctatttc aaggagacag      60 tcata atg aaa tac cta ttg cct acg gca gcc gct gga ttg tta tta ctc    110
```

```
              Met Lys Tyr Leu Leu Pro Thr Ala Ala Ala Gly Leu Leu Leu Leu
                1               5                  10                  15 gct gcc caa cca gcg atg gcg cag gtg cag ctg cag gag ttg ggt cca          158
Ala Ala Gln Pro Ala Met Ala Gln Val Gln Leu Gln Glu Leu Gly Pro
                     20                  25                  30 agg ctg gtg agg cct tca cag acc ctg atc ctc acc tgc act gtc tct          206
Arg Leu Val Arg Pro Ser Gln Thr Leu Ile Leu Thr Cys Thr Val Ser
                 35                  40                  45 gga ggc tcc gtc agc ggc gat gag tat tac tgg agt tgg ctc cgt cag          254
Gly Gly Ser Val Ser Gly Asp Glu Tyr Tyr Trp Ser Trp Leu Arg Gln
             50                  55                  60 acc cca ggg aag ggc ctg gag tgg att ggg tac atg tct tac aga ggg          302
Thr Pro Gly Lys Gly Leu Glu Trp Ile Gly Tyr Met Ser Tyr Arg Gly
         65                  70                  75 agc agt tat tac agt ccg tcc ctc cag agt cga gtt acc att gca gtg          350
Ser Ser Tyr Tyr Ser Pro Ser Leu Gln Ser Arg Val Thr Ile Ala Val
 80                  85                  90                  95 gac agg tcc aag aac gaa ttt tcc ctg aag ctg acg tct gtg act gcc          398
Asp Arg Ser Lys Asn Glu Phe Ser Leu Lys Leu Thr Ser Val Thr Ala
                    100                 105                 110 gca gac gcg gcc gta tat ttc tgt gcc aga aaa tat tgt ggt ggc gat          446
Ala Asp Ala Ala Val Tyr Phe Cys Ala Arg Lys Tyr Cys Gly Gly Asp
                115                 120                 125 tgc agg agt ggt ttt gat atc tgg ggc cga ggg aca atg gtc act gtc          494
Cys Arg Ser Gly Phe Asp Ile Trp Gly Arg Gly Thr Met Val Thr Val
            130                 135                 140 gcc agc gct agc acc aag ggc cca tcg gtc ttc ccc ctg gca ccc tcc          542
Ala Ser Ala Ser Thr Lys Gly Pro Ser Val Phe Pro Leu Ala Pro Ser
145                 150                 155 tcc aag agc acc tct ggg ggc aca gcg gcc ctg ggc tgc ctg gtc aag          590
Ser Lys Ser Thr Ser Gly Gly Thr Ala Ala Leu Gly Cys Leu Val Lys
160                 165                 170                 175 gac tac ttc ccc gaa ccg gtg acg gtg tcg tgg aac tca ggc gcc ctg          638
Asp Tyr Phe Pro Glu Pro Val Thr Val Ser Trp Asn Ser Gly Ala Leu
                180                 185                 190 acc agc ggc gtg cac acc ttc ccg gct gtc cta cag tcc tca gga ctc          686
Thr Ser Gly Val His Thr Phe Pro Ala Val Leu Gln Ser Ser Gly Leu
            195                 200                 205 tac tcc ctc agc agc gtg gtg acc gtg ccc tcc agc agc ttg ggc acc          734
Tyr Ser Leu Ser Ser Val Val Thr Val Pro Ser Ser Ser Leu Gly Thr
        210                 215                 220 cag acc tac atc tgc aac gtg aat cac aag ccc agc aac acc aag gtg          782
Gln Thr Tyr Ile Cys Asn Val Asn His Lys Pro Ser Asn Thr Lys Val
    225                 230                 235 gac aag aaa gtt gag ccc aaa tct tgt acc agg cac agg cag ccc aga          830
Asp Lys Lys Val Glu Pro Lys Ser Cys Thr Arg His Arg Gln Pro Arg
240                 245                 250                 255 ggc tgg gag cag ctc tac aac acc gtg tca ttt aac ctt gga gaa gct          878
Gly Trp Glu Gln Leu Tyr Asn Thr Val Ser Phe Asn Leu Gly Glu Ala
                260                 265                 270 tat gag tac ccc act ttt ata caa gat ttg cgc aat gaa ttg gct aag          926
Tyr Glu Tyr Pro Thr Phe Ile Gln Asp Leu Arg Asn Glu Leu Ala Lys
            275                 280                 285 ggc aca cca gta tgt caa ctt cca gtg aca cta caa acc ata gcc gat          974
Gly Thr Pro Val Cys Gln Leu Pro Val Thr Leu Gln Thr Ile Ala Asp
        290                 295                 300 gac aag cga ttt gtt cta gtt gat atc act acg acc tcg aag aaa aca         1022
Asp Lys Arg Phe Val Leu Val Asp Ile Thr Thr Thr Ser Lys Lys Thr
    305                 310                 315 gtt aag gtt gct ata gat gtg aca gat gtg tat gtt gtg ggt tat caa         1070
```

```
Val Lys Val Ala Ile Asp Val Thr Asp Val Tyr Val Val Gly Tyr Gln
320             325                 330                 335 gac aaa tgg gat ggc aaa gat cga gct gtt ttc ctt gac aag gtt cct       1118
Asp Lys Trp Asp Gly Lys Asp Arg Ala Val Phe Leu Asp Lys Val Pro
        340                 345                 350 act gtt gca act agt aaa ctt ttc cca ggg gtg act aat cgt gta acg       1166
Thr Val Ala Thr Ser Lys Leu Phe Pro Gly Val Thr Asn Arg Val Thr
            355                 360                 365 tta aca ttt gat ggc agc tat cag aaa ctt gtg aat gct gcc aaa gct       1214
Leu Thr Phe Asp Gly Ser Tyr Gln Lys Leu Val Asn Ala Ala Lys Ala
        370                 375                 380 gat aga aag gct ctc gaa ctg ggg gtt aac aaa ttg gaa ttt tcc att       1262
Asp Arg Lys Ala Leu Glu Leu Gly Val Asn Lys Leu Glu Phe Ser Ile
385                 390                 395 gaa gca atc cat ggt aaa acg ata aat ggt caa gag gca gcc aag ttc       1310
Glu Ala Ile His Gly Lys Thr Ile Asn Gly Gln Glu Ala Ala Lys Phe
400                 405                 410                 415 ttt ctt att gtc atc caa atg gtt tca gag gca gct cgg ttc aaa tat       1358
Phe Leu Ile Val Ile Gln Met Val Ser Glu Ala Ala Arg Phe Lys Tyr
                420                 425                 430 att gag act gag gtg gtt gat aga gga tta tat gga tca ttc aaa cct       1406
Ile Glu Thr Glu Val Val Asp Arg Gly Leu Tyr Gly Ser Phe Lys Pro
            435                 440                 445 aat ttt aaa gta ttg aac ttg gag aac aat tgg ggc gac atc tct gat       1454
Asn Phe Lys Val Leu Asn Leu Glu Asn Asn Trp Gly Asp Ile Ser Asp
        450                 455                 460 gcc att cac aaa tca tcc cca caa tgt acc act att aat ccg gca ctt       1502
Ala Ile His Lys Ser Ser Pro Gln Cys Thr Thr Ile Asn Pro Ala Leu
465                 470                 475 cag ttg ata agc ccc tca aat gac cca tgg gtt gta aat aaa gtg agt       1550
Gln Leu Ile Ser Pro Ser Asn Asp Pro Trp Val Val Asn Lys Val Ser
480                 485                 490                 495 caa att agt ccc gat atg ggt atc ctt aag ttt aaa agc tcc aaa           1595
Gln Ile Ser Pro Asp Met Gly Ile Leu Lys Phe Lys Ser Ser Lys
                500                 505                 510 tagtga                                                                1601

<210> SEQ ID NO 85
<211> LENGTH: 510
<212> TYPE: PRT
<213> ORGANISM: Artificial Sequence
<220> FEATURE:
<223> OTHER INFORMATION: Immunoconjugate

<400> SEQUENCE: 85

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Leu Gly Pro Arg
            20                  25                  30

Leu Val Arg Pro Ser Gln Thr Leu Ile Leu Thr Cys Thr Val Ser Gly
        35                  40                  45

Gly Ser Val Ser Gly Asp Glu Tyr Tyr Trp Ser Trp Leu Arg Gln Thr
    50                  55                  60

Pro Gly Lys Gly Leu Glu Trp Ile Gly Tyr Met Ser Tyr Arg Gly Ser
65                  70                  75                  80

Ser Tyr Tyr Ser Pro Ser Leu Gln Ser Arg Val Thr Ile Ala Val Asp
                85                  90                  95

Arg Ser Lys Asn Glu Phe Ser Leu Lys Leu Thr Ser Val Thr Ala Ala
            100                 105                 110
```

Asp Ala Ala Val Tyr Phe Cys Ala Arg Lys Tyr Cys Gly Asp Cys
            115                 120                 125

Arg Ser Gly Phe Asp Ile Trp Gly Arg Gly Thr Met Val Thr Val Ala
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Thr Arg His Arg Gln Pro Arg Gly
            245                 250                 255

Trp Glu Gln Leu Tyr Asn Thr Val Ser Phe Asn Leu Gly Glu Ala Tyr
            260                 265                 270

Glu Tyr Pro Thr Phe Ile Gln Asp Leu Arg Asn Glu Leu Ala Lys Gly
            275                 280                 285

Thr Pro Val Cys Gln Leu Pro Val Thr Leu Gln Thr Ile Ala Asp Asp
290                 295                 300

Lys Arg Phe Val Leu Val Asp Ile Thr Thr Thr Ser Lys Lys Thr Val
305                 310                 315                 320

Lys Val Ala Ile Asp Val Thr Asp Val Tyr Val Val Gly Tyr Gln Asp
            325                 330                 335

Lys Trp Asp Gly Lys Asp Arg Ala Val Phe Leu Asp Lys Val Pro Thr
            340                 345                 350

Val Ala Thr Ser Lys Leu Phe Pro Gly Val Thr Asn Arg Val Thr Leu
            355                 360                 365

Thr Phe Asp Gly Ser Tyr Gln Lys Leu Val Asn Ala Ala Lys Ala Asp
370                 375                 380

Arg Lys Ala Leu Glu Leu Gly Val Asn Lys Leu Glu Phe Ser Ile Glu
385                 390                 395                 400

Ala Ile His Gly Lys Thr Ile Asn Gly Gln Glu Ala Ala Lys Phe Phe
            405                 410                 415

Leu Ile Val Ile Gln Met Val Ser Glu Ala Ala Arg Phe Lys Tyr Ile
            420                 425                 430

Glu Thr Glu Val Val Asp Arg Gly Leu Tyr Gly Ser Phe Lys Pro Asn
            435                 440                 445

Phe Lys Val Leu Asn Leu Glu Asn Asn Trp Gly Asp Ile Ser Asp Ala
450                 455                 460

Ile His Lys Ser Ser Pro Gln Cys Thr Thr Ile Asn Pro Ala Leu Gln
465                 470                 475                 480

Leu Ile Ser Pro Ser Asn Asp Pro Trp Val Val Asn Lys Val Ser Gln
            485                 490                 495

Ile Ser Pro Asp Met Gly Ile Leu Lys Phe Lys Ser Ser Lys
            500                 505                 510

<210> SEQ ID NO 86
<211> LENGTH: 799
<212> TYPE: DNA
<213> ORGANISM: Artificial Sequence

```
<220> FEATURE:
<223> OTHER INFORMATION: Immunoconjugate
<220> FEATURE:
<221> NAME/KEY: CDS
<222> LOCATION: (71)..(790)

<400> SEQUENCE: 86
ctagagtcga cctgcaggtc tatggaacga taaatgccca tgaaaattct atttcaagga        60
gacagtcata atg aaa tac cta ttg cct acg gca gcc gct gga ttg tta         109
              Met Lys Tyr Leu Leu Pro Thr Ala Ala Ala Gly Leu Leu
                1               5                  10 tta ctc gcg gcc caa ccg gcc atg gcg cac cat cat cac cat cac tat        157
Leu Leu Ala Ala Gln Pro Ala Met Ala His His His His His His Tyr
         15                  20                  25 gag ctg act cag cca ccc tca gtg tcc gtg tcc cca gga cag aaa gcc        205
Glu Leu Thr Gln Pro Pro Ser Val Ser Val Ser Pro Gly Gln Lys Ala
 30                  35                  40                  45 ttc ata acc tgc tct gga gat aac ctg ggg aat aaa tat gtg tgc tgg        253
Phe Ile Thr Cys Ser Gly Asp Asn Leu Gly Asn Lys Tyr Val Cys Trp
                 50                  55                  60 tat caa cag aag cca ggc cag tcc cct gtc ctg gtc atc tat gaa gat        301
Tyr Gln Gln Lys Pro Gly Gln Ser Pro Val Leu Val Ile Tyr Glu Asp
             65                  70                  75 acc aag agg ccc tca ggg atc cct gag cga ttc tct gcc tcc aac tct        349
Thr Lys Arg Pro Ser Gly Ile Pro Glu Arg Phe Ser Ala Ser Asn Ser
         80                  85                  90 ggg aat aca gcc act ctg acc atc agc ggg acg cag cct ata gat gag        397
Gly Asn Thr Ala Thr Leu Thr Ile Ser Gly Thr Gln Pro Ile Asp Glu
 95                  100                 105 gct gac tac tac tgt cag gcg tgg gac agc cgc act gaa atc ttc gga        445
Ala Asp Tyr Tyr Cys Gln Ala Trp Asp Ser Arg Thr Glu Ile Phe Gly
110                 115                 120                 125 act ggg acc aag gtc acc gtc cta agt cag ccc aag gcc aac ccc act        493
Thr Gly Thr Lys Val Thr Val Leu Ser Gln Pro Lys Ala Asn Pro Thr
                 130                 135                 140 gtc act ctg ttc ccg ccc tcc tct gag gag ctc caa gcc aac aag gcc        541
Val Thr Leu Phe Pro Pro Ser Ser Glu Glu Leu Gln Ala Asn Lys Ala
             145                 150                 155 aca cta gtg tgt ctg atc agt gac ttc tac ccg gga gct gtg aca gtg        589
Thr Leu Val Cys Leu Ile Ser Asp Phe Tyr Pro Gly Ala Val Thr Val
         160                 165                 170 gcc tgg aag gca gat ggc agc ccc gtc aag gcg gga gtg gag acc acc        637
Ala Trp Lys Ala Asp Gly Ser Pro Val Lys Ala Gly Val Glu Thr Thr
175                 180                 185 aaa ccc tcc aaa cag agc aac aac aag tac gcg gcc agc agc tac ctg        685
Lys Pro Ser Lys Gln Ser Asn Asn Lys Tyr Ala Ala Ser Ser Tyr Leu
190                 195                 200                 205 agc ctg acg ccc gag cag tgg aag tcc cac aga agc tac agc tgc cag        733
Ser Leu Thr Pro Glu Gln Trp Lys Ser His Arg Ser Tyr Ser Cys Gln
                 210                 215                 220 gtc acg cat gaa ggg agc acc gtg gag aag aca gtg gcc cct aca gaa        781
Val Thr His Glu Gly Ser Thr Val Glu Lys Thr Val Ala Pro Thr Glu
             225                 230                 235 tgt tca tag tgactcgag                                                   799
Cys Ser <210> SEQ ID NO 87
<211> LENGTH: 239
<212> TYPE: PRT
<213> ORGANISM: Artificial Sequence
<220> FEATURE:
<223> OTHER INFORMATION: Immunoconjugate
```

```
<400> SEQUENCE: 87

Met Lys Tyr Leu Leu Pro Thr Ala Ala Ala Gly Leu Leu Leu Leu Ala
1               5                   10                  15

Ala Gln Pro Ala Met Ala His His His His His His Tyr Glu Leu Thr
            20                  25                  30

Gln Pro Pro Ser Val Ser Val Ser Pro Gly Gln Lys Ala Phe Ile Thr
        35                  40                  45

Cys Ser Gly Asp Asn Leu Gly Asn Lys Tyr Val Cys Trp Tyr Gln Gln
    50                  55                  60

Lys Pro Gly Gln Ser Pro Val Leu Val Ile Tyr Glu Asp Thr Lys Arg
65                  70                  75                  80

Pro Ser Gly Ile Pro Glu Arg Phe Ser Ala Ser Asn Ser Gly Asn Thr
                85                  90                  95

Ala Thr Leu Thr Ile Ser Gly Thr Gln Pro Ile Asp Glu Ala Asp Tyr
            100                 105                 110

Tyr Cys Gln Ala Trp Asp Ser Arg Thr Glu Ile Phe Gly Thr Gly Thr
        115                 120                 125

Lys Val Thr Val Leu Ser Gln Pro Lys Ala Asn Pro Thr Val Thr Leu
    130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Gly Ser Pro Val Lys Ala Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Gln Val Thr His
    210                 215                 220

Glu Gly Ser Thr Val Glu Lys Thr Val Ala Pro Thr Glu Cys Ser
225                 230                 235
```

We claim:

1. An isolated antibody comprising: a light chain complementarity determining region 1 (CDR1) comprising the amino acid sequence of SEQ ID NO:1; a light chain complementarity determining region 2 (CDR2) comprising the amino acid sequence SEQ ID NO:2; a light chain complementarity determining region 3 (CDR3) comprising the amino acid sequence SEQ ID NO:3; a heavy chain complementarity determining region 1 (CDR1) comprising the amino acid sequence SEQ ID NO:4; a heavy chain complementarity determining region 2 (CDR2) comprising the amino acid sequence SEQ ID NO:5; and a heavy chain complementarity determining region 3 (CDR3) comprising the amino acid sequence SEQ ID NO:6.

2. The isolated antibody of claim 1, wherein the antibody is an antigen-binding antibody fragment.

3. The isolated antibody of claim 2, wherein the antibody fragment is a Fab, Fab', F(ab')$_2$, scFv, dsFv, ds-scFv, dimers, minibodies, diabodies, and multimers thereof or bispecific antibody fragments.

4. The isolated antibody of claim 1, wherein the antibody binds to a protein selected from the group consisting of: 5-v8 interface of CD44E; a v8 exon of CD44; CD44E; a protein comprising amino acid sequence ATNMDSSHSIT; alpha-fetoprotein; a protein comprising amino acid sequence of SEQ ID NOS: 38, 39, 40, 41, 42, 43, 44, and/or 45; a protein having a molecular weight of between 48-54 kDa and an isoelectric point between 5.1-5.5; a protein comprising amino acid sequence of SEQ ID NOS: 46, 47, 48, 49, 50, 51, 52, 53, 54, 55, 56, 57, 58, 59, 60, 61, 62, 63, 64, 65, 66, 67, 68, 69, 70, 71, 72, 73, 74 and/or 75; a protein comprising amino acid sequence of SEQ ID NO: 14; a protein comprising amino acid sequence of SEQ ID NO: 15; and a protein comprising amino acid sequence of SEQ ID NO: 16.

5. A composition comprising the isolated antibody of claim 1 with a pharmaceutically acceptable excipient, carrier, buffer or stabilizer.

6. A kit for diagnosing cancer comprising the isolated antibody of claim 1 and instructions for the use thereof to diagnose cancer.

7. The kit according to claim 6 for diagnosing breast cancer.

8. A diagnostic agent comprising (1) the isolated antibody according to claim 1 and (2) a label that produces a detectable signal, directly or indirectly.

9. The diagnostic agent of claim 8, wherein the label is a radioisotope, a fluorescent compound, a chemiluminescent compound, an enzyme, an imaging agent or a metal ion.

10. A kit comprising the diagnostic agent of claim 8 and instructions for the use thereof.

11. An immunoconjugate comprising:
(1) an isolated antibody that binds to an antigen on or in a cancer cell wherein the isolated antibody comprises: a light chain complementarity determining region 1 (CDR1) comprising the amino acid sequence of SEQ ID NO:1; a light chain complementarity determining region 2 (CDR2) comprising the amino acid sequence SEQ ID NO:2; a light chain complementarity determining region 3 (CDR3) comprising the amino acid sequence SEQ ID NO:3; a heavy chain complementarity determining region 1 (CDR1) comprising the amino acid sequence SEQ ID NO:4; a heavy chain complementarity determining region 2 (CDR2) comprising the amino acid sequence SEQ ID NO:5; and a heavy chain complementarity determining region 3 (CDR3) comprising the amino acid sequence SEQ ID NO:6 and
(2) a cancer therapeutic that is cytotoxic or cytostatic.

12. The immunoconjugate of claim 11, wherein the antigen is selected from the group consisting of: a protein comprising 5-v8 interface of CD44E; a v8 exon of CD44; CD44E; a protein comprising amino acid sequence ATNMDSSHSIT; alpha-fetoprotein; a protein comprising amino acid sequence of SEQ ID NOS: 38, 39, 40, 41, 42, 43, 44, and/or 45; a protein having a molecular weight of between 48-54 kDa and an isoelectric point between 5.1-5.5; a protein comprising amino acid sequence of SEQ ID NOS: 46, 47, 48, 49, 50, 51, 52, 53, 54, 55, 56, 57, 58, 59, 60, 61, 62, 63, 64, 65, 66, 67, 68, 69, 70, 71, 72, 73, 74 and/or 75; a protein comprising amino acid sequence of SEQ ID NO: 14; a protein comprising amino acid sequence of SEQ ID NO: 15; and a protein comprising amino acid sequence of SEQ ID NO: 16.

13. The immunoconjugate of claim 11, wherein the cancer therapeutic is a toxin.

14. The immunoconjugate of claim 13, wherein the toxin is a ribosome-inactivating polypeptide.

15. The immunoconjugate of claim 14, wherein the toxin is selected from the group consisting of gelonin, bouganin, saporin, ricin, ricin A chain, bryodin, diphtheria, restrictocin and *Pseudomonas* exotoxin A.

16. The immunoconjugate of claim 14, wherein the toxin is modified bouganin.

17. The immunoconjugate of claim 14, wherein the toxin is a truncated for of *Pseudomonas* exotoxin A that consists of amino acids 252-608.

18. The immunoconjugate of claim 11 comprising a protein encoded by the nucleotide sequence of SEQ ID NO: 11.

19. The immunoconjugate of claim 11 comprising the amino acid sequence of SEQ ID NO: 12 and 13.

20. The immunoconjugate of claim 11 wherein the immunotoxin is internalized by the cancer cell.

21. A composition comprising the immunoconjugate of claim 11 with a pharmaceutically acceptable excipient, carrier, buffer or stabilizer.

* * * * *

UNITED STATES PATENT AND TRADEMARK OFFICE
CERTIFICATE OF CORRECTION

PATENT NO. : 8,383,117 B2  
APPLICATION NO. : 11/570198  
DATED : February 26, 2013  
INVENTOR(S) : Nicholas Ronald Glover et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this
Sixth Day of January, 2015

Michelle K. Lee
*Deputy Director of the United States Patent and Trademark Office*